(12) United States Patent
Whittacre et al.

(10) Patent No.: US 8,145,502 B2
(45) Date of Patent: *Mar. 27, 2012

(54) ALGORITHM AND PROGRAM FOR THE HANDLING AND ADMINISTRATION OF RADIOACTIVE PHARMACEUTICALS

(75) Inventors: Bretten H. Whittacre, Henderson, NV (US); Troy V. Curnutt, Pocatello, ID (US); Jared Johnson, Henderson, NV (US)

(73) Assignee: Biodose, LLC, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/632,723

(22) Filed: Dec. 7, 2009

(65) Prior Publication Data

US 2010/0153136 A1    Jun. 17, 2010

Related U.S. Application Data

(63) Continuation of application No. 10/283,480, filed on Oct. 29, 2002, now Pat. No. 7,630,907.

(60) Provisional application No. 60/335,088, filed on Oct. 30, 2001.

(51) Int. Cl.
  *G06Q 10/00* (2006.01)
  *G06Q 50/00* (2006.01)
(52) U.S. Cl. .............................................. 705/2; 705/3
(58) Field of Classification Search ................... 705/2–3
  See application file for complete search history.

(56) References Cited

U.S. PATENT DOCUMENTS

| | | | |
|---|---|---|---|
| 5,479,969 A | | 1/1996 | Hardie et al. |
| 5,664,112 A | | 9/1997 | Sturgeon et al. |
| 5,803,906 A | * | 9/1998 | Pratt et al. ..................... 600/300 |
| 5,842,976 A | * | 12/1998 | Williamson .................. 600/300 |
| 5,883,370 A | * | 3/1999 | Walker et al. ................. 235/375 |
| 5,995,936 A | | 11/1999 | Brais et al. |
| 6,157,036 A | | 12/2000 | Whiting et al. |
| 6,425,174 B1 | | 7/2002 | Reich |
| 2001/0044755 A1 | | 11/2001 | Sakamoto |
| 2001/0047281 A1 | | 11/2001 | Keresman, III et al. |
| 2002/0010595 A1 | | 1/2002 | Kapp |
| 2002/0017005 A1 | | 2/2002 | Kim et al. |
| 2002/0093189 A1 | * | 7/2002 | Krupa ............................ 283/81 |

(Continued)

OTHER PUBLICATIONS

Neil A. Petry. NRC and FDA Regulations Affecting Nuclear Pharmacy Practice. Journal of Pharmacy Practice; 2(5), pp. 306-313.*

(Continued)

*Primary Examiner* — Sheetal R Rangrej

(74) *Attorney, Agent, or Firm* — Pillsbury Winthrop Shaw Pittman LLP

(57) ABSTRACT

An algorithm and associated program for performing method steps in the maintaining of records and generating of reports used in the processing of radioactive pharmaceuticals. The algorithm is used as the basis of a program which can accomplish this method automatically. The method involves the determination of dose, the acquisition of the materials, scheduling for the issuance of doses and for future doses, the actual monitoring and control of material and equipment disposal. The algorithm and method are also adapted for the generation of reports on a periodic basis. In short, the method performed by the algorithm allows for an automation through a computer system and this, in turn, allows for the automatic processing of the steps performed and the controls involved in the dispensing of radioactive pharmaceuticals and automatically allows for the generation of governmental and other reports therefor.

2 Claims, 77 Drawing Sheets

U.S. PATENT DOCUMENTS

| | | |
|---|---|---|
| 2002/0155064 A1 | 10/2002 | Reubi |
| 2002/0169636 A1 | 11/2002 | Eggers et al. |
| 2003/0018495 A1 | 1/2003 | Sussman |
| 2003/0033317 A1 | 2/2003 | Ziglin |
| 2003/0105555 A1 | 6/2003 | Lunak et al. |
| 2003/0131011 A1 | 7/2003 | Haunschild et al. |
| 2003/0204602 A1 | 10/2003 | Hudson et al. |
| 2004/0078231 A1* | 4/2004 | Wilkes et al. .................... 705/2 |

OTHER PUBLICATIONS

Code of Federal Regulations. Nuclear Regulatory Commission. (Parts 20 and 35) pp. 1-25. <http://www.access.gpo.gov/cgi-bin/cfrassemble.cgi?title=200010>.

Nuclear Pharmacy Compounding Practice Committee, et al. Nuclear Pharmacy Guidelines for the compounding of Radiopharmaceuticals. Jul. 17, 2001, pp. 1-31.

James a. Ponto and Joseph c. Hung. Nuclear Pharmacy, Part II: Nuclear Pharmacy Practice Today. Journal of Nuclear Medicine Technology; Jun. 2000; 29(2), pp. 76-84.

Code of Federal Regulations. Nuclear Regulatory Commission (Parts 20 and 35) 26 pages. http://www.access.gpo.gov/cgi_bin/cfrassemble.cgi?title=200010.

Code of Federal Regulations. Nuclear Regulatory Commission (Parts 20 and 71), http://www.access.gpo.gov/cgi_bin/cfrassemble.cgi?title=200010, 51 pages.

Code of Federal Regulations. Nuclear Regulatory Commission (Parts 20, 32, 36, 39 and 60) 38 pages. http://www.access.gpo.gov/cgi_bin/cfrassemble.cgi?title=200010.

* cited by examiner

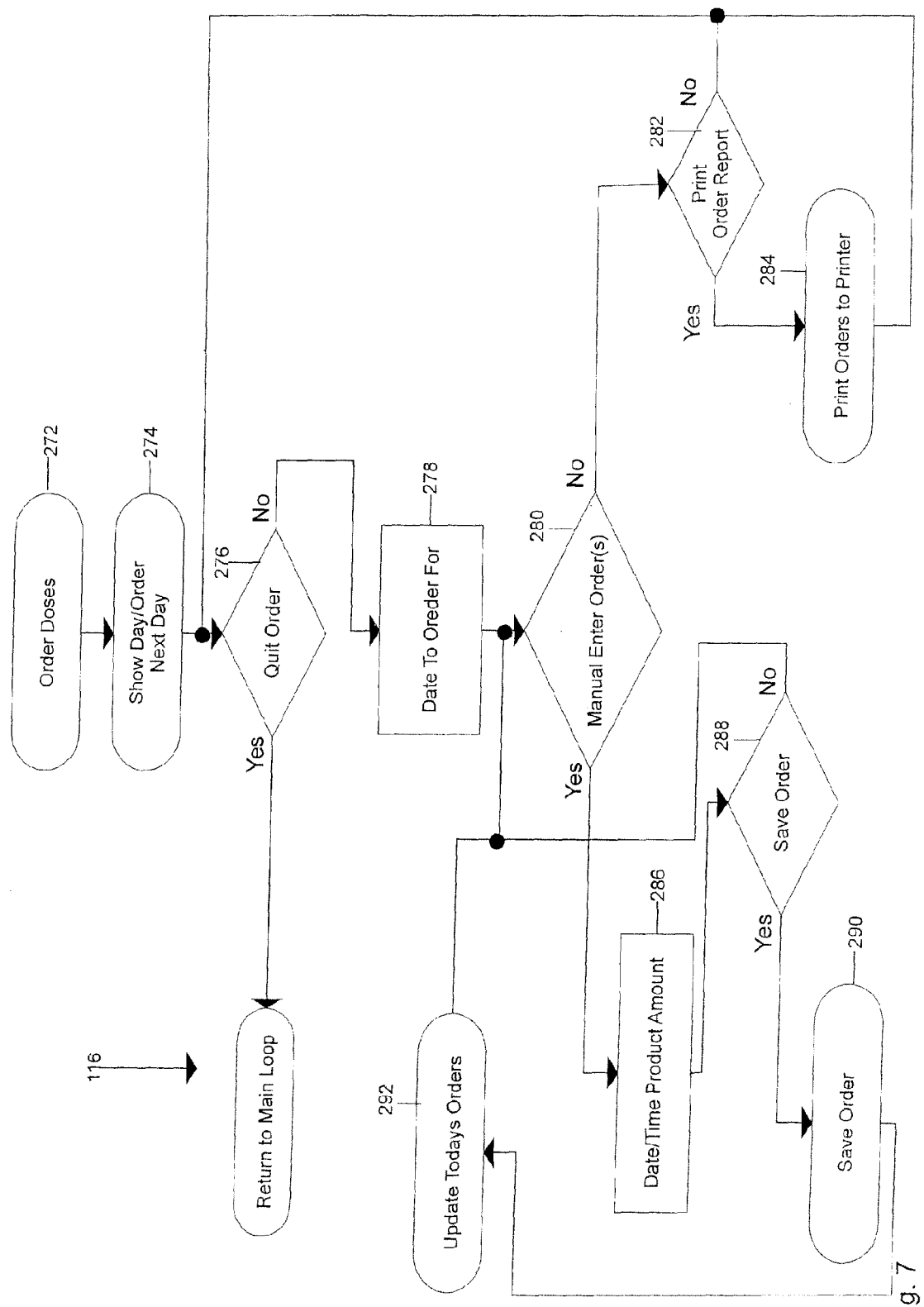

| Product | |
|---|---|
| Code # | Product |
| 001 | Myoview |
| 002 | Myoview |
| | |
| | |
| | |
| | |

| Inventory | |
|---|---|
| Code # | Amount |
| 001 | 50 ml |
| 002 | |
| 003 | |
| 004 | |
| 005 | 78 ml |

| Scheduler | |
|---|---|
| Code # | Name |
| | Smith |
| | |
| | |
| | |
| | |
| | |

| Injection Dose | |
|---|---|
| Code # | Amount |
| 013 | 10 ml |
| | |
| | |
| | |
| | |
| | |

| Patient | |
|---|---|
| Code # | Name |
| 022 | Jones |
| | |
| | |
| | |
| | |
| | |

| Accumulate Data | | | | | |
|---|---|---|---|---|---|
| Code # | Product | Inventory Amount | Scheduler | Injection Dose | Patient |
| 002 | Myoview | | | | |
| 001 | | 50 ml | | | |
| 010 | | | Smith | | |
| 013 | | | | 10 ml | |
| 022 | | | | | Jones |
| | | | | | |
| | | | | | |

Fig. 71

ALGORITHM AND PROGRAM FOR THE HANDLING AND ADMINISTRATION OF RADIOACTIVE PHARMACEUTICALS

RELATED APPLICATION

This application is a continuation of application Ser. No. 10/283,480, filed Oct. 29, 2002, now U.S. Pat. No. 7,630,907, which is based on and claims the benefit of priority of our provisional U.S. patent application Ser. No. 60/335,088, filed Oct. 30, 2001, for Method Enabling Algorithm and Program for the Handling and Administration of Radioactive Pharmaceuticals.

This application is related to application Ser. No. 10/447,726, filed May 28, 2003, entitled "Integrated distribution and communication process and algorithm for providing, handling, distributing or generating reports regarding radioactive pharmaceuticals," which is a continuation-in-part of application serial No. 10/283,480, filed Oct. 29, 2002.

This application is related to application Ser. No. 10/447,727, filed May 28, 2003, entitled "Pharmacy based method and algorithm for handling of radioactive pharmaceuticals and generating of reports therefore," which is continuation-in-part of application Ser. No. 10/283,480, filed Oct. 29, 2002.

BACKGROUND OF THE INVENTION

1. Field of the Invention

This invention relates in general to certain new and useful improvements in algorithm and methods for enabling the handling and administration of radioactive pharmaceuticals, and more particularly, to an algorithm, a program used therein, and an associated method which allows for the control of radioactive pharmaceuticals and the areas in which they are used and for a system and method for maintaining records and generating reports, and handling the dispensing of radioactive pharmaceuticals.

2. Brief Description of Related Art

In recent years, the field of nuclear medicine has relied more heavily upon the use of radioactive pharmaceuticals, primarily for diagnostic purposes, but for other treatment purposes as well. Generally, radioactive pharmaceuticals were introduced into a patient's blood stream, and allowed to be carried to one or more organs of the body which are to be investigated. In this way, it was possible to specifically locate tumors or other dysfunction causing conditions.

Also, in the recent past, it has been found that certain tumors, and other dysfunction causing conditions, will not become visually apparent from presently available diagnosing techniques, such as magnetic resonance imaging and computer tomography. However, it has been found that these conditions will become visually apparent when radioactive dies are lodged or introduced into the tumors and other tissue in which observation may be necessary. Due to the greater widespread use of radioactive pharmaceuticals, and the potential for radioactive hazard, both in the handling and in the disposition of waste materials, there has been a need for careful control over the use of such materials. In fact, in the United States, both the federal government and the various state governments have levied numerous regulations controlling the use and disposition of these radioactive materials.

The pharmaceutical houses which dispense these radioactive materials, are required to account for complete use of the radioactive material, including the handling of the waste resulting therefrom, and generate reports to those government agencies which are involved in the regulation thereof. The same holds true for the end users of these radioactive pharmaceuticals, as for example, the hospitals and the physicians and medical centers which are involved in the administration of these radioactive pharmaceuticals. These end users are typically involved in the business of providing medical care and administering for radioactive pharmaceuticals, and generating governmental reports becomes a very time consuming and, indeed, an expensive task.

This increasing widespread use of radioactive pharmaceutical materials has given rise to a number of radioactive pharmaceutical supply facilities which supply the end users, e.g., medical institutions, hospitals and physicians with these radioactive materials. These supply houses are frequently referred to as "pharmacies" and "radioactive drug pharmacies". Some of the end users, such as hospitals, etc., were originally quite lax in control of the radioactive materials, and in the maintenance of data for generation of reports. Consequently, the U.S. federal government and the various state governments, at least in the United States, have enacted, and even tightened, regulations which require very accurate reporting on a periodic basis.

The federal government as well as several state governments, call for the reporting of the use of each aliquoted portion of radioactive material, including the use of handling materials such as gloves, storage tubes, scales, and the like. Thus, more specifically, reports must be made on the type of material used for each particular patient, the amounts used, the dates of use, and even how any remnant portions of the material were discarded. Moreover, reports must be made on the handling equipment which may have come into contact with radioactive materials, such as test tubes, beakers, and the like.

It may be appreciated that there are numerous details involving the complete handling of all radioactive material, and the equipment used in the handling of that material, and hence, reporting requirements are extensive and render the preparation of reports to be time consuming and hence, costly. In fact, depending upon the amount of radioactive material dispensed, the number of patients receiving these materials, and like factors, personnel are frequently exclusively devoted to gathering of information and preparation of such reports.

There have been attempts to use data processing techniques for storage of information. However, and heretofore, these data processing techniques generally rely upon the pure storage of information, without much attention being given to segregation of data for report preparation and auditing, and even for informational purpose by the user thereof.

There has been, at least, one attempt to provide a software program for gathering of data and generating reports for the handling and dispensing of radioactive materials. However, this attempt involves only the specific use of the materials offered by a single pharmaceutical facility. It is not capable of universal use with a variety of pharmaceutical materials and a variety of conditions not otherwise existing with this particular source of pharmaceutical materials. Moreover, the program is severely lacking, and still requires a substantial amount of personnel time in gathering of information and generating the necessary governmental reports.

One of the primary problems with the prior art software programs which have been generated for handling and dispensing of radioactive materials, is the fact that they were not particularly user-friendly. The operator of the system had to be fairly well experienced in dealing with computers in general, and in switching back and forth between subroutines in complex algorithms. As a simple example, if there were a menu page presented on the screen of a monitor, the operator would have to track the particular page involved, in order to examine details of a routine on that menu page. In many cases, the operator even had to go to additional menu screens in order to find the routine which was needed. Moreover, when the operator finished with one routine, the algorithm did not allow the operator to immediately return to the main screen, with a mere click of a pushbutton switch.

Another one of the problems inherent in the prior art system is that they were not readily adaptable to changing requirements. Thus, if a governmental agency required a new type of report or an altered report to be generated, this almost necessitated the need for a skilled programmer to input that instruction base necessary for an operator to use. Consequently, the prior art programs were severely lacking in many respects.

It can also be recognized that each medical institution has different operating procedures than others. Moreover, certain of the medical facilities have larger staffs than others, and hence, a greater capability of record keeping. Consequently, and inasmuch as the medical facilities would prefer to avoid substantial record keeping and the details associated with administering of these radioactive pharmaceuticals, each facility may prefer a somewhat different algorithm to track the use of radioactive pharmaceuticals. Therefore, there is a clear need for an algorithm and a program which operates a method for administering the radioactive pharmaceuticals, and for also generating the required governmental reports therefor.

There has therefore been a need for a system which will allow for the automatic retention of data, segregation of data according to specific functions and materials, and which will also generate reports based on the collected data, all on an automated basis. There has also been a need for a system of this type which could be universally applicable to the collection and segregation of data and generation of reports, based on the particular materials used and the functions which are necessary by a user of such system.

In addition to the foregoing, there has been a need for these end users, as well as the radioactive pharmaceutical companies, to maintain internal controls over the use and dispensing of radioactive pharmaceuticals, in order to insure for the health and the safety of those parties dealing directly with these pharmaceuticals. This need for control over the radioactive pharmaceuticals also involves an intended need for careful control and monitoring of the areas in which the pharmaceuticals are used, inasmuch as the latter can also become contaminated from the radioactive pharmaceuticals.

Furthermore, there has also been a need for an orderly and regulated manner in which an end users and a radioactive pharmaceutical company could maintain appropriate record keeping in order to insure the ordering of radioactive pharmaceuticals on a needed basis. It may be appreciated that in many cases, the pharmaceutical activity of a radioactive pharmaceutical can decrease rapidly, depending upon the half life of the radioactive material. Consequently, careful control over the ordering of the radioactive materials and dispensing must also be maintained.

There has been a further need for some method to allow for internal control over the use of radioactive pharmaceuticals, and also some method which allows for the control and ordering of radioactive pharmaceuticals and related materials timely in response to demand therefor.

OBJECTS OF THE INVENTION

It is, therefore, one of the primary objects of the present invention to provide an algorithm and a program capable of performing method steps used in a process for gathering data on radioactive materials, and generating reports therefrom.

It is another object of the present invention to provide an algorithm and program of the type stated, which can be universally adapted to a variety of situations and a variety of radioactive materials which may be used.

It is a further object of the present invention to provide an algorithm and a program which will automatically gather data, segregate the data according to specific materials and equipments used and the parties receiving such materials, as well as disposal thereof.

It is an additional object of the present invention to provide an algorithm and a program of the type stated, which can be fully automated and where reports can be generated with very little manual attention on a periodic basis, and containing that information precisely categorized and specified as required by various governmental agencies.

It is another salient object of the present invention to provide a method for gathering data regarding the use of radioactive materials, and segregating that data according to report categories and allowing for generation of reports on a fully automated basis.

It is still another object of the present invention to provide a method of using an algorithm and a program to efficiently, and with a minimal amount of manual intervention, permit the gathering of data arising from the use of pharmaceutical materials.

It is also an object of the present invention to provide a method and algorithm which will use data generated regarding the use and disposal of radioactive materials, and which will allow for generation of reports specific to the needs of various governmental agencies, and which reporting requirements can be altered in response to changing regulations of the various governmental agencies therefor.

With the above and other objects in view, our invention resides in the novel features of form, construction, arrangement and combination of steps involved in the algorithm and program as well as the method accomplished thereby in accordance with the present invention.

BRIEF SUMMARY OF THE INVENTION

The present invention primarily relates to an algorithm and a method which provides for the administration of radioactive pharmaceuticals. The algorithm and method of the invention primarily is used by the so-called "pharmacy", as opposed to the physician or hospital. The pharmacy typically deals exclusively with radioactive materials, and primarily the radioactive pharmaceuticals.

The present invention also relies upon the algorithm and a software program based thereon, for operating a method used in the handling of and administration of, as well as maintenance of records and generating reports for processing and using of the radioactive pharmaceuticals. More specifically, a wide variety of steps are required, usually by governmental control, in the handling and distribution of radioactive pharmaceuticals. The algorithm of the present invention is used as a basis for a program which automates the handling and distribution of these pharmaceuticals. Specifically, the algorithm allows for quality control of the various pharmaceutical products which are to be distributed.

Thereafter, the algorithm includes inputs for the actual dosing of each individual patient, who has been entered into the program. These patients will change on a periodic basis. After a patient has been dosed, that is, administered with the radioactive pharmaceutical, a schedule for the next visit is maintained. In this way, the hospital or medical facility is able to order and have available on time the next dosage to be administered to each particular patient. Moreover, the timing must be fairly well controlled inasmuch as these radioactive pharmaceuticals have a relatively short half-life and the individual dosages could rapidly degrade or deteriorate if not used promptly and on the appropriate time.

In many cases, kits of the dosages of a particular radioactive pharmaceutical product may be required in larger amounts which are then broken into individual doses. These doses are introduced into syringes in certain cases. Thus, the pharmaceutical laboratory involved will take the larger quantity of the radioactive pharmaceutical and divide that large quantity into the individual doses which are introduced into syringes.

After all handling of the radioactive pharmaceutical product, the area in which doses were handled must be monitored. In effect, a determination is made as to whether or not there is any remnant radioactive material on counters or the like. All such radioactive material must be accounted for and reported, typically to governmental institutions involved in use of same.

After the monitoring, the various syringes and other components and items used in handling the dosages must be collected. These syringes and other items will still contain remnant amounts of the radioactive material and are themselves radioactive. Consequently, they must be disposed of appropriately. The term "disposal" does not mean that these instrumentalities, that is, the various syringes and items used in the handling of the dosages or other items which come into contact with the dosages, are being discarded in the waste. Rather, the radioactive pharmaceutical laboratory or pharmacy typically does not have facilities for such waste. Consequently, they are taken to a location where radioactive waste can be disposed.

In connection with the delivery of the various instrumentalities which were used in handling of the radioactive pharmaceuticals, it is, of course, necessary to keep careful track and monitoring of these instrumentalities, such as the syringes and the like. This is to insure that these radioactive materials do not become available to parties who might use the radioactivity for illegal or undesirable purposes. Moreover, governmental agencies typically require complete reporting on the disposal of all such instrumentalities.

Finally, periodic reports are generated. In particular, these reports are usually made on a daily basis in order to conform to governmental requirements. In this way, all reports are automatically prepared in accordance with the algorithm and the method steps performed thereby.

One of the important aspects of the present invention is that the algorithm causes the operation of a method for performing all of the foregoing activities, as well as other types of activities, including monitoring activities. Moreover, all of the information can be introduced and used on an automated basis. Thus, with a large number of patients, for example, and each receiving different doses of different radioactive pharmaceuticals, the medical facility is required to maintain a large amount of data. The algorithm of the invention will allow for the organization of this data, so as to advise the pharmacy of those patients which are next due for radioactive pharmaceutical administration. The algorithm will also allow for automatic advisement to a party at the medical facility monitoring this information, such that the party knows when to order the various radioactive materials.

The algorithm is designed to receive input data about each of the particular patients, and organize that data. In this way, the electronic data processing system which uses the algorithm not only advises of the doses which must be administered, but also advises of sources for those particular radioactive pharmaceuticals, and the like. In this way, the medical facility can then prepare, on a timely basis, the necessary doses.

As indicated previously, many of these pharmaceuticals have a relatively short half life. Consequently, it is of some importance to insure that the doses are ordered from a source of the radioactive pharmaceutical, or otherwise, that the doses are prepared directly, either at the radioactive pharmacy or at the medical facility, with the proper amount of radiation.

In addition to the foregoing, the algorithm allows for setting the dates and times, and continuously updates the date and time, relative to the information which has been stored.

The algorithm of the invention also allows for necessary attendant operations, such as billing for preparation and providing of the radioactive pharmaceutical, the maintaining of insurance information, and the like. The input data will include input data regarding the physician, the type of pharmaceutical which has been prescribed, and like information.

One of the important aspects of the present invention is that personnel are not required to operate calculators in order to make determinations. In effect, all computations which are necessary in connection with the administration and the record keeping, are performed internally with the algorithm and programs. As a simple example, by introducing the weight of a patient, the amount of the radioactive pharmaceutical to be administered to that patient can be determined.

In substance, it is not necessary for the user to engage in the need for locating a calculator, looking up a formula to enable calculation, and thereafter, performing the necessary calculation. This alone not only functions as a time conservation, but it also eliminates the possibility of error in performing the calculation function. In addition, the algorithm of the present invention will also provide for ranges to inform the user as to whether or not a particular calculation was high or low. As a simple example, if a user is performing a daily constancy determination, that is, e.g., meters operating in accordance with the recommended ranges, the algorithm will give the previous ranges, both high and low, so that the user can automatically determine right at that point in time if the meters are within the corrected range or not within the corrected range.

Heretofore, any prior art system required a determination, typically at the end of the month, and at which point, if a meter was not within the required range, tests may have to be re-conducted. Moreover, tests may have previously been made with a faulty meter which requires re-calibration. The prior art systems were simply not effective to provide that information immediately.

The algorithm and the program derived therefrom can also be customized to the needs of a particular user. This is due to the fact that the algorithm is arranged to maintain data in various data groups, and combine that data to produce information which must be presented to a user of the system. Moreover, by virtue of the fact that the computer itself can be connected to the World Wide Web, or other Global Communication Network, it is possible to update and download and upload information on an on-line basis.

One of the important aspects of the present invention is the fact that the algorithm and the method allow for the automatic assignment of internal numbers to various segments of data. As a simple example, if the radioactivity pharmaceutical Myoview is to be administered to a patient by the name of Smith, and in an amount of 50 ml., each of those pieces of information are assigned an internal computer number. Thereafter, each of the pieces of information are stored in a separate file. In this way, it is not necessary to introduce redundant data for another patient who is to receive Myoview, in the same or different amounts. The algorithm thereupon allows for the assumption of data through the internal computer numbers, as requested by the operator. Indeed, it is not even necessary for the operator to know of these internal numbers. Rather, the internal numbers represent an internal file accessing scheme for the gathering of data and associating the data.

Another one of the important aspects of the present invention relies in the fact that the algorithm has been designed so that it is essentially "fool proof", in that an operator who may be relatively unskilled in computer operations can, nevertheless, perform all of the necessary method steps with the method generating algorithm of the present invention. The algorithm is designed to generate one or more main displays in the form of flow diagrams on the screen of a computer monitor. Each of the routines forming part of that algorithm are laid out in a manner in which they must be sequentially performed.

In view of the fact that there is a complex amount of information and a complex number of tasks to address, the menus are designed so that each of the routines are not only in their proper sequential location on the screen in which they are to be performed, but the operator can immediately address any particular routine merely by the click of a return pushbutton switch on the keyboard pad of the computer. Moreover, after the operator has performed all of the tasks necessary in a particular routine, another mere actuation of the return switch, or other selected switch, will cause the program to return to the main screen so that the operator immediately knows the next routine which is to be performed.

Even when a routine is performed, the operator can automatically and easily address subroutines by simple actuation of another keyboard switch. In this way, the algorithm effectively carries the operator through all of the routines which must be performed, thereby avoiding problems of faulty memory or problems which involve a lack of computer skills on the part of the user. When the operator has finished with a subroutine, the click of the same switch will automatically bring the operator back to the routine, and another click of the return switch will automatically bring the operator to the main menu. In this way, the algorithm is so designed so that there is little chance for error.

The various routines are also organized so that the operation is relatively simplified. As a simple example, the scheduling of a patient is contained in one routine, the review of a drug for a patient in another routine, selection of a drug for a patient in a third routine, selection of the particular patient to receive that drug in a fourth routine, etc. The routine even provides for introduction of the initials of the operator so that one can track the efficiency of use of the operator.

The algorithm and the method accomplished thereby, is hereinafter described in more detail in the following detailed description. However, certain individual activities are not necessarily included therein. For example, a selection of a desired word processor which may be incorporated in the program is not necessarily described, and the type of forms which may be stored and selected are not necessarily described. In addition, activities such as backup recording, help files, and the like, may be included with the algorithm, but since these activities are not critical to the operation of the method, they are neither illustrated nor described herein.

This present invention thereby provides a unique and novel algorithm and associated program and the method steps taken through the use of the algorithm and program for fulfilling steps in the handling and administration of radioactive pharmaceuticals, which thereby fulfills all of the above-identified objects and other objects which will become more fully apparent from the consideration of the forms in which it may be embodied. One of these forms is more fully illustrated in the accompanying drawings and described in the following detailed description of the invention. However, it should be understood that the accompanying drawings and this detailed description are set forth only for purposes of illustrating the general principles of the invention.

BRIEF DESCRIPTION OF THE DRAWINGS

Figure 1:
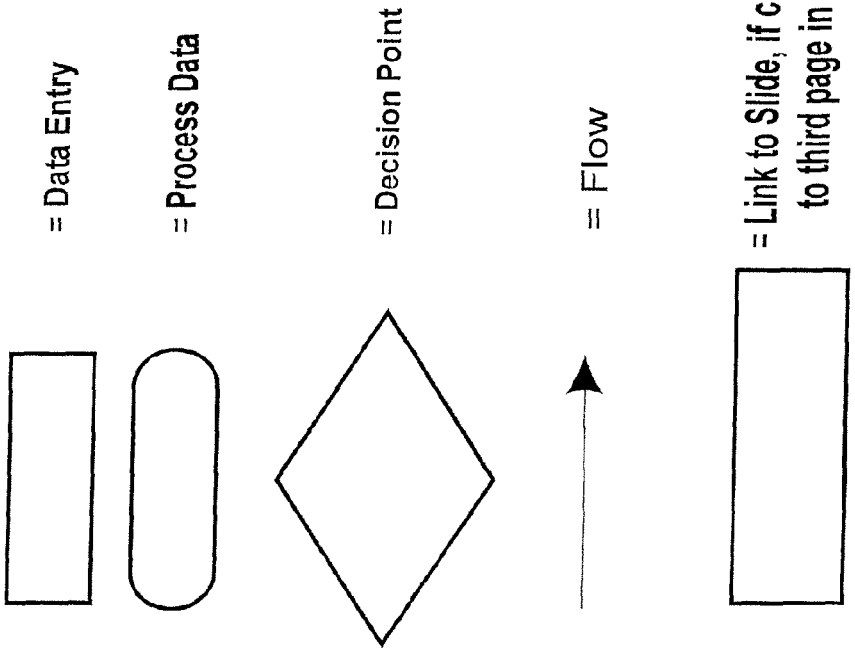
Figure 2:
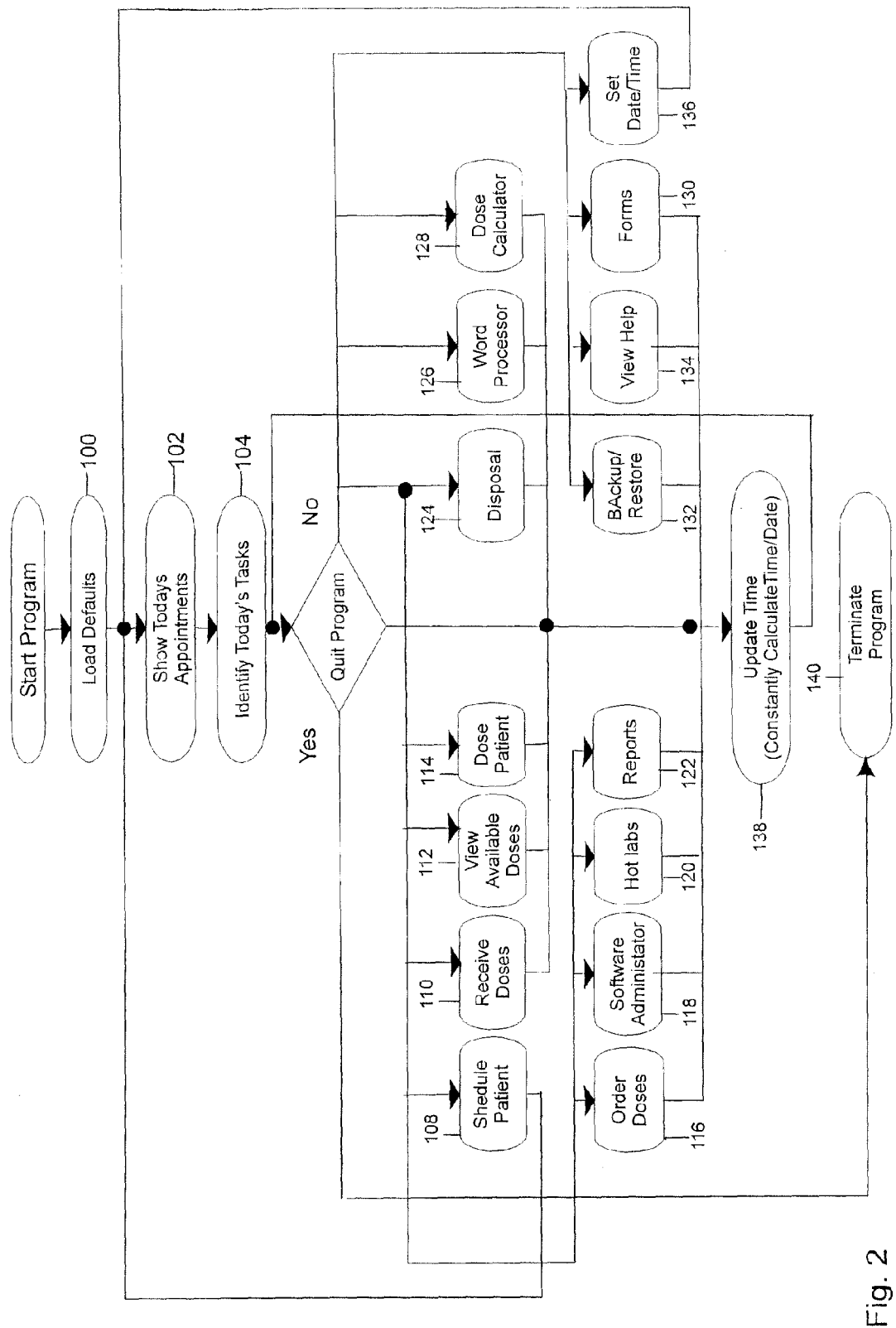
Figure 3:
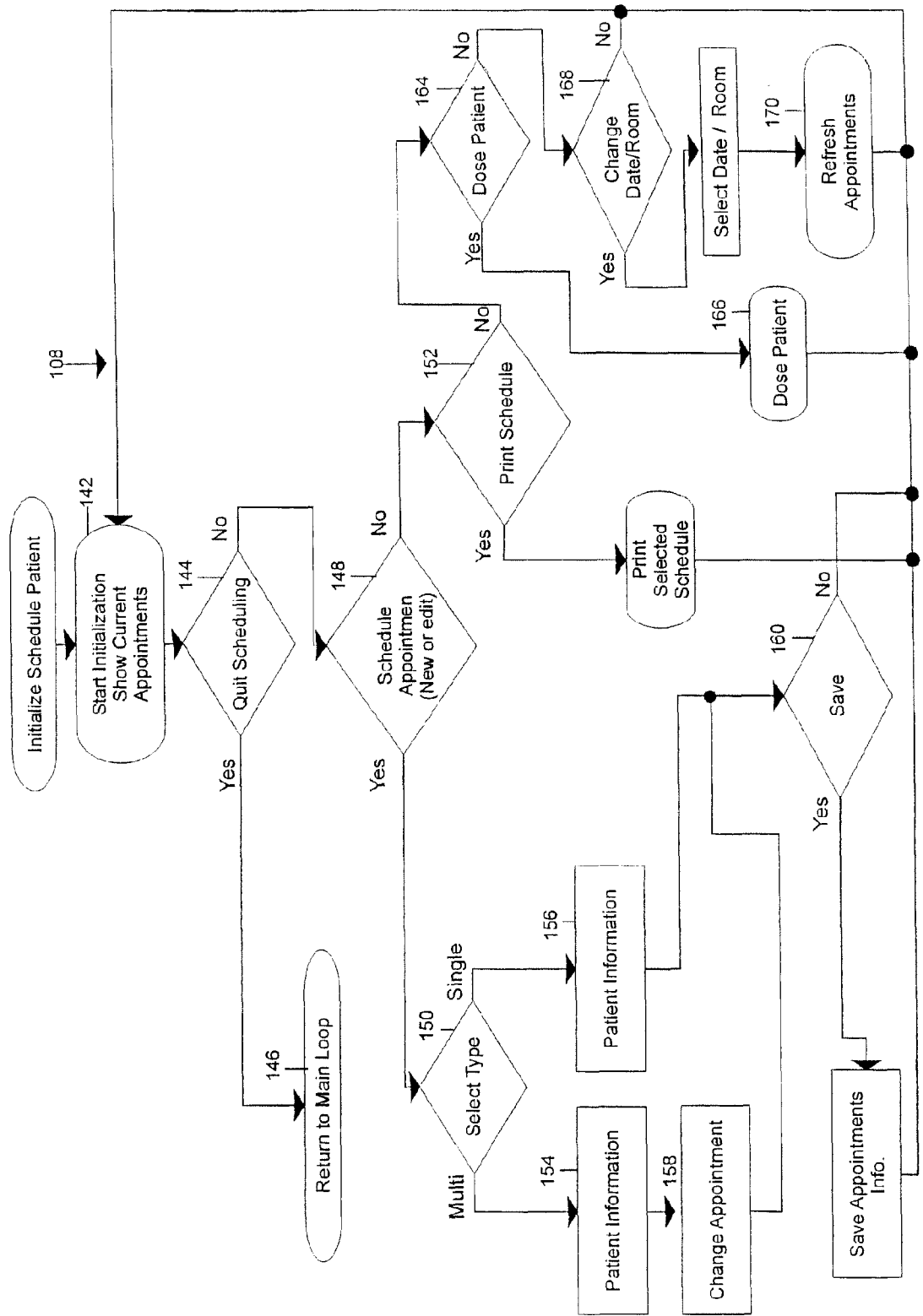
Figure 4A:
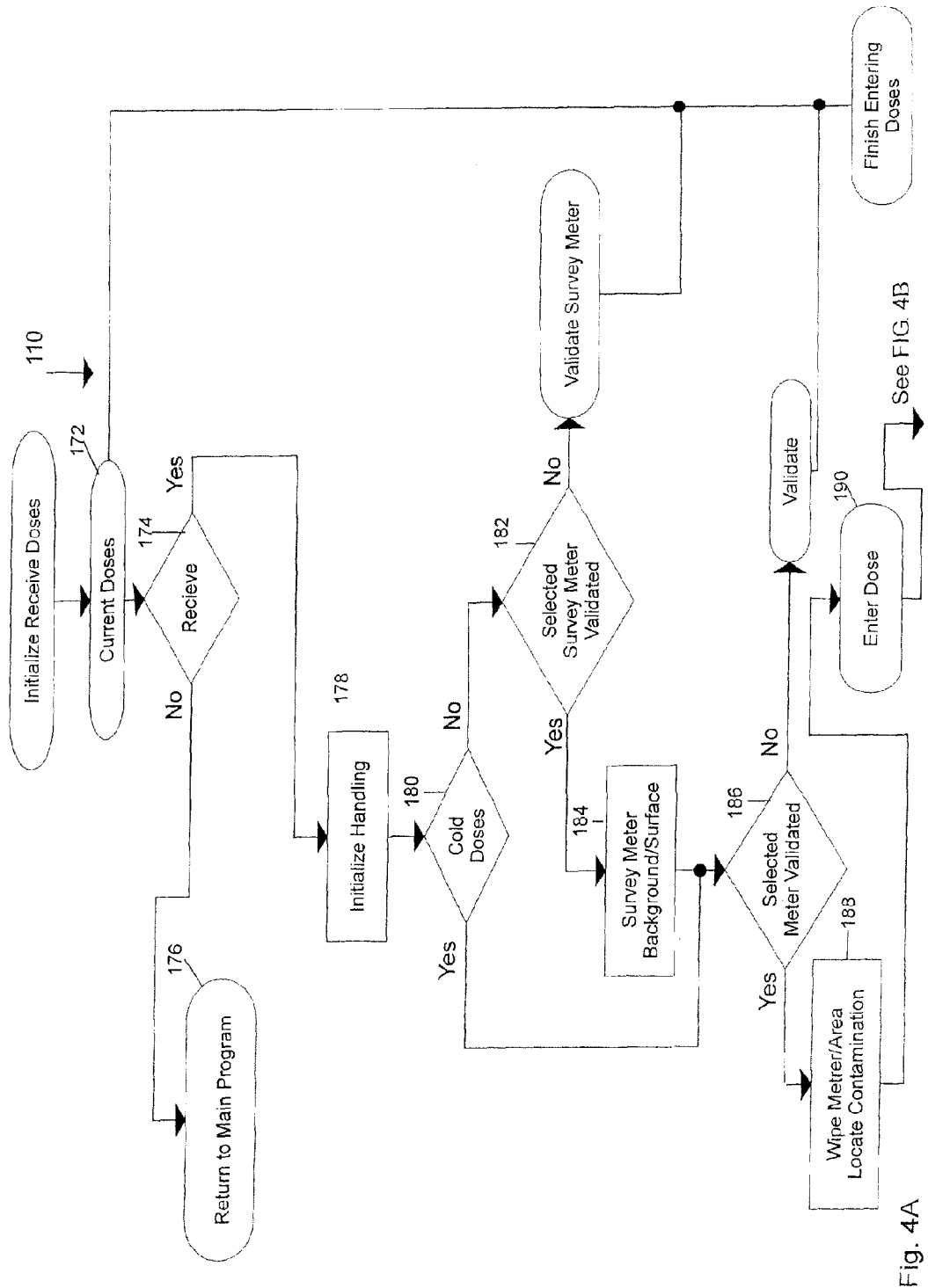
Figure 4B:
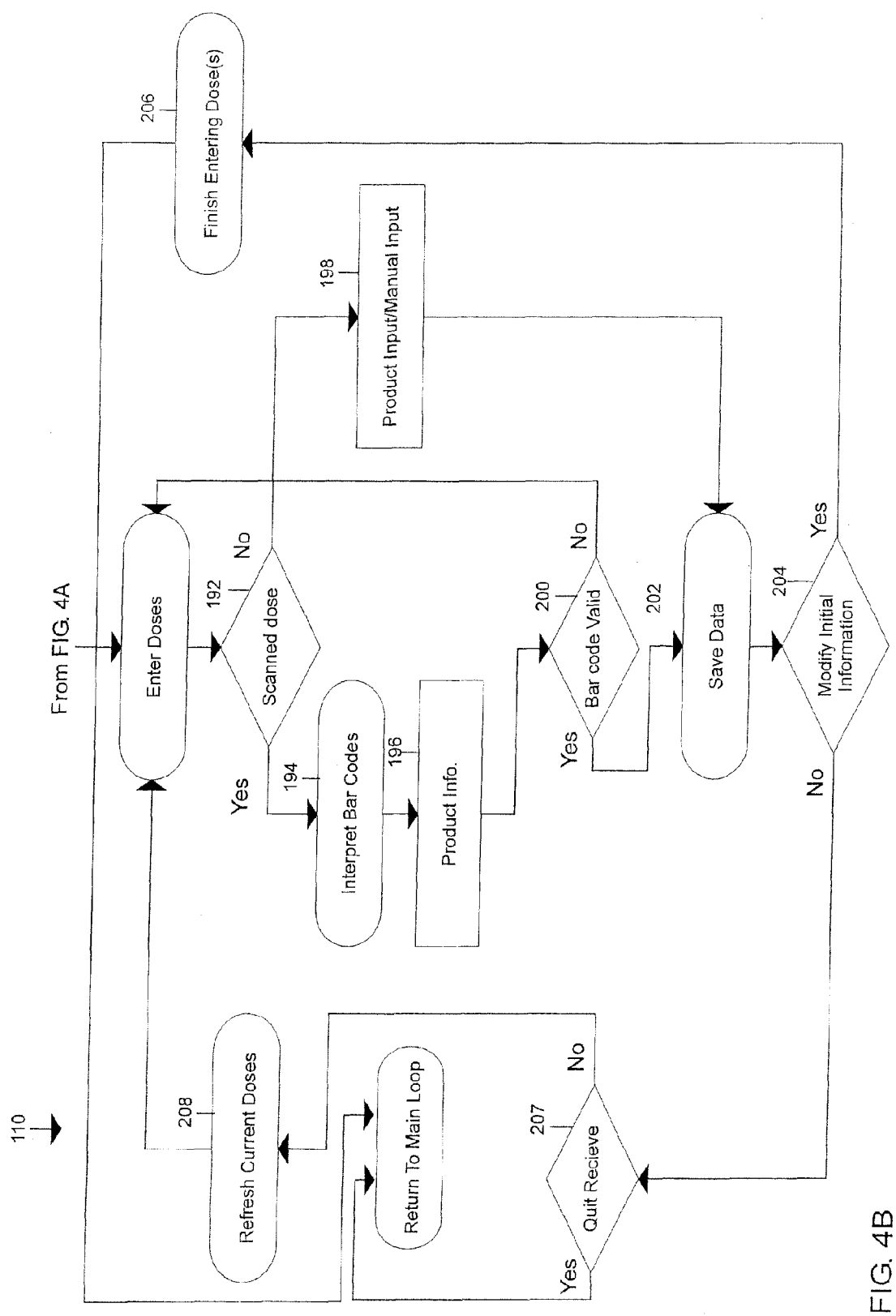
Figure 5:
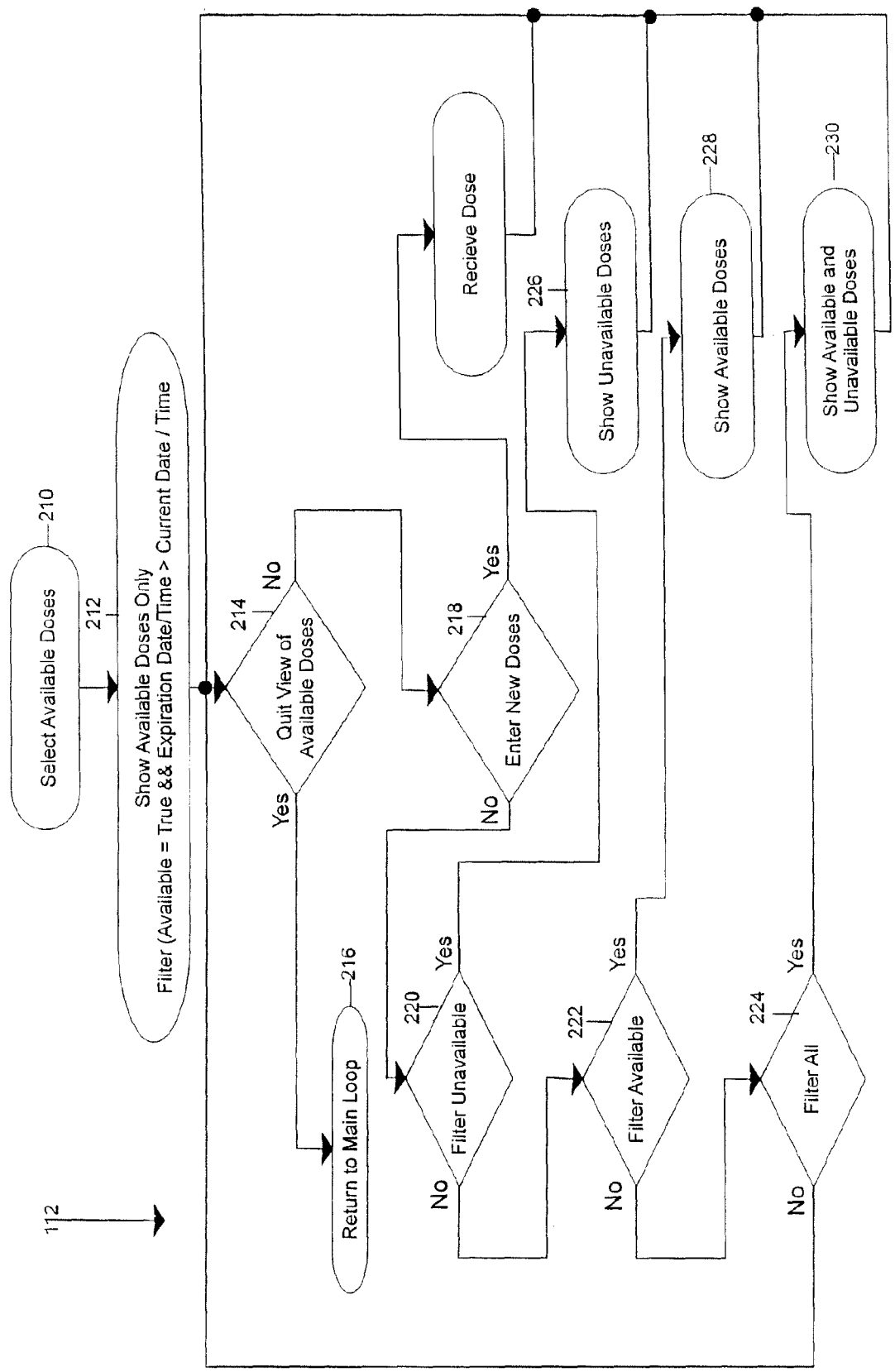
Figure 6A:
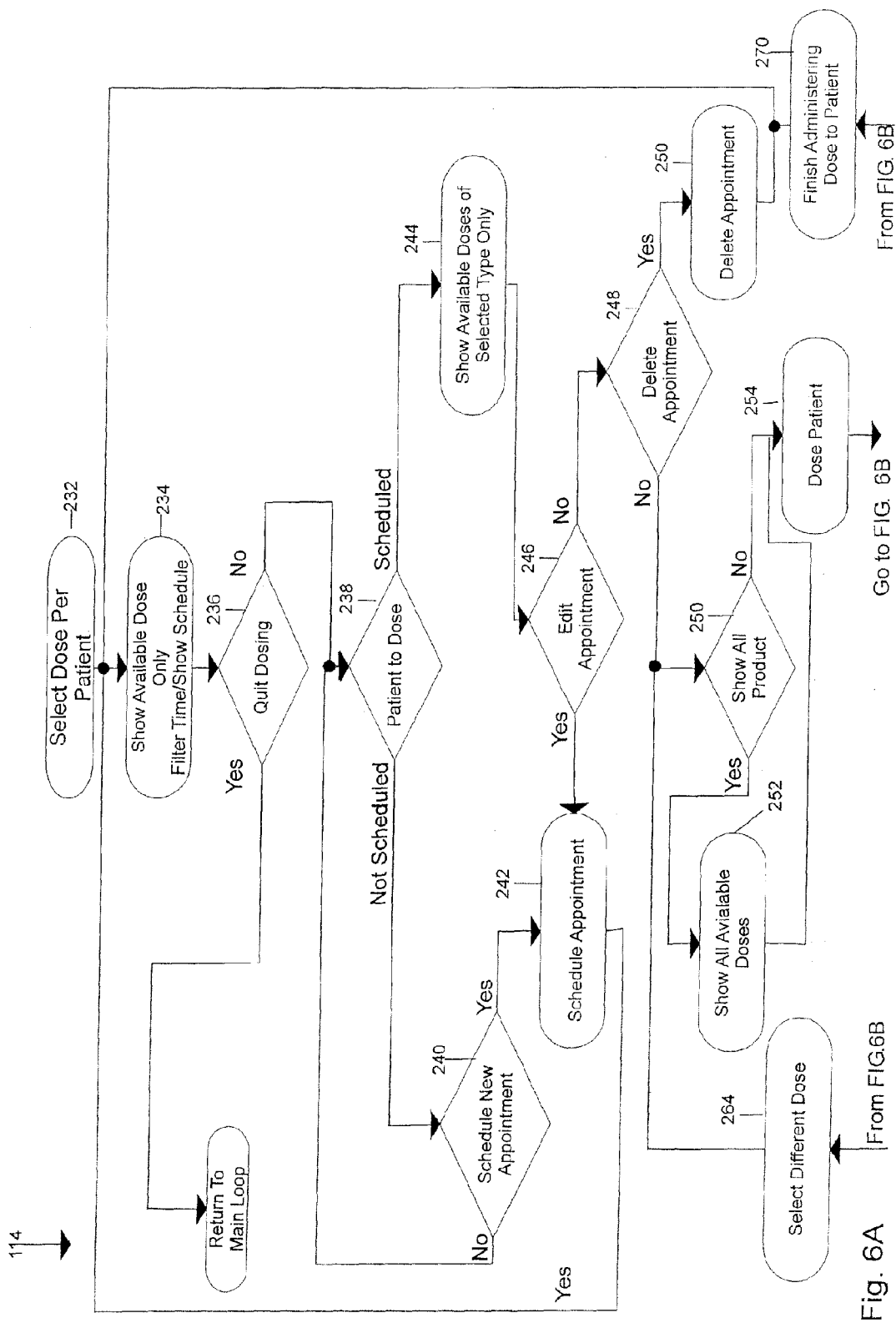
Figure 6B:
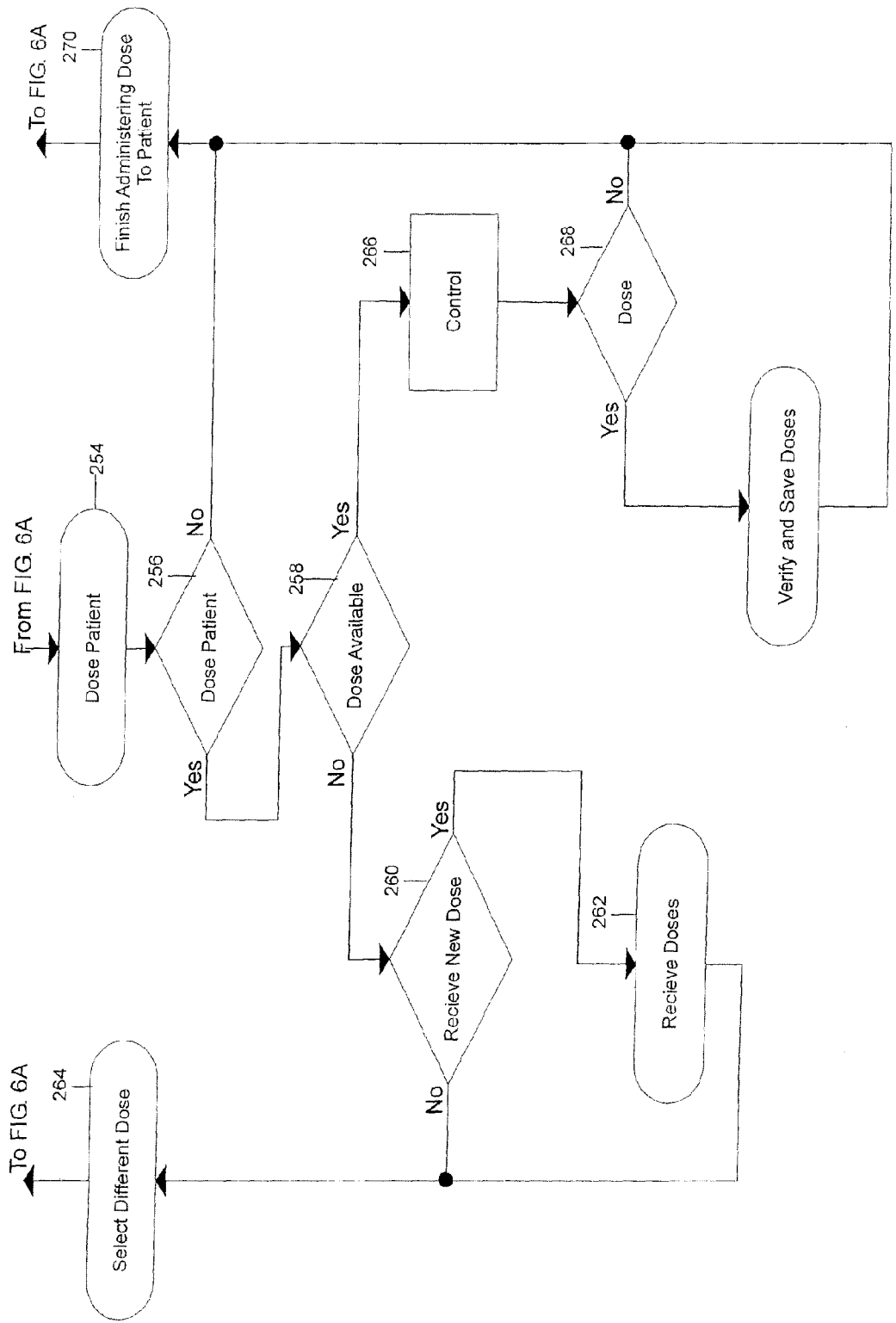
Figure 8A:
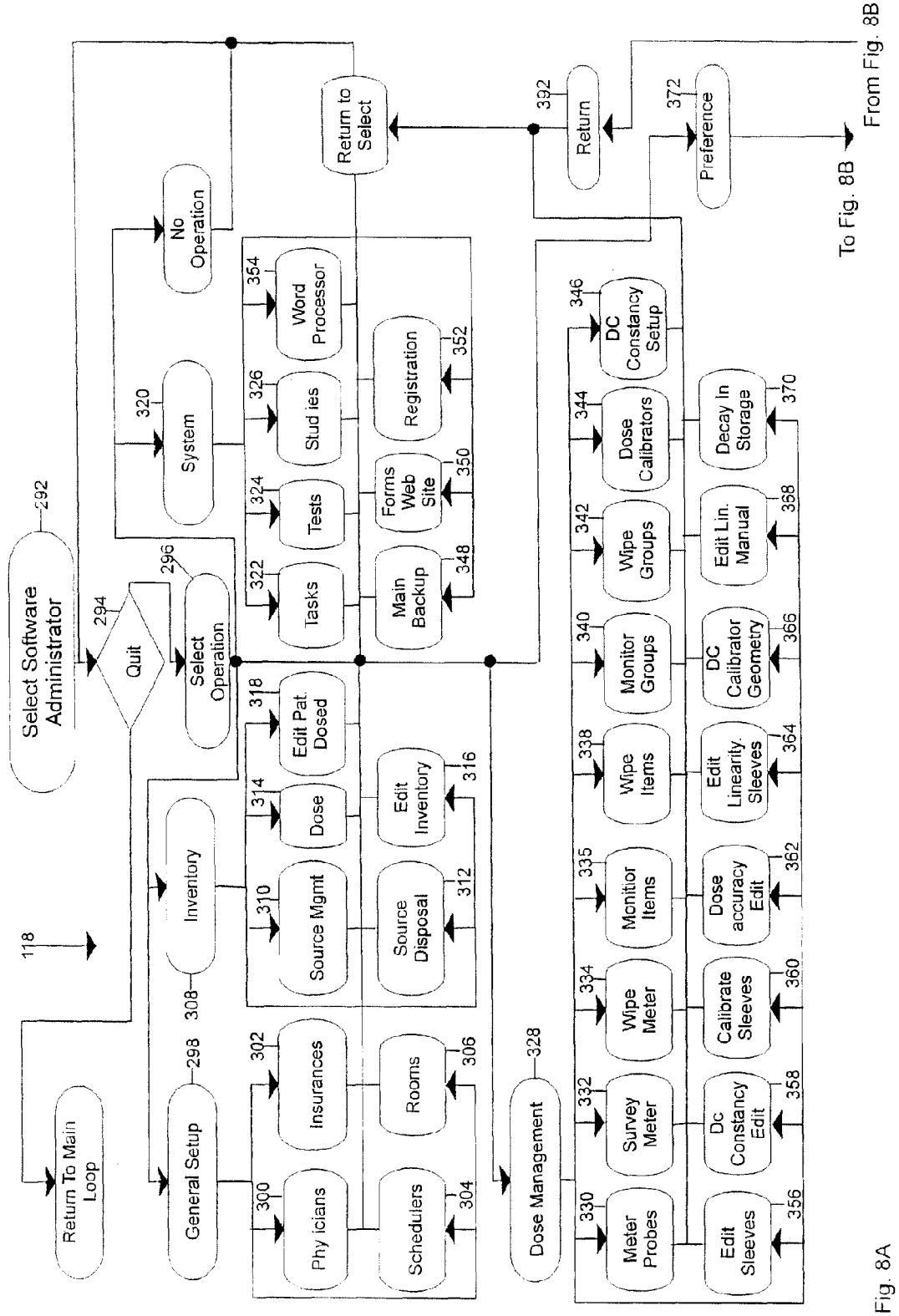
Figure 8B:
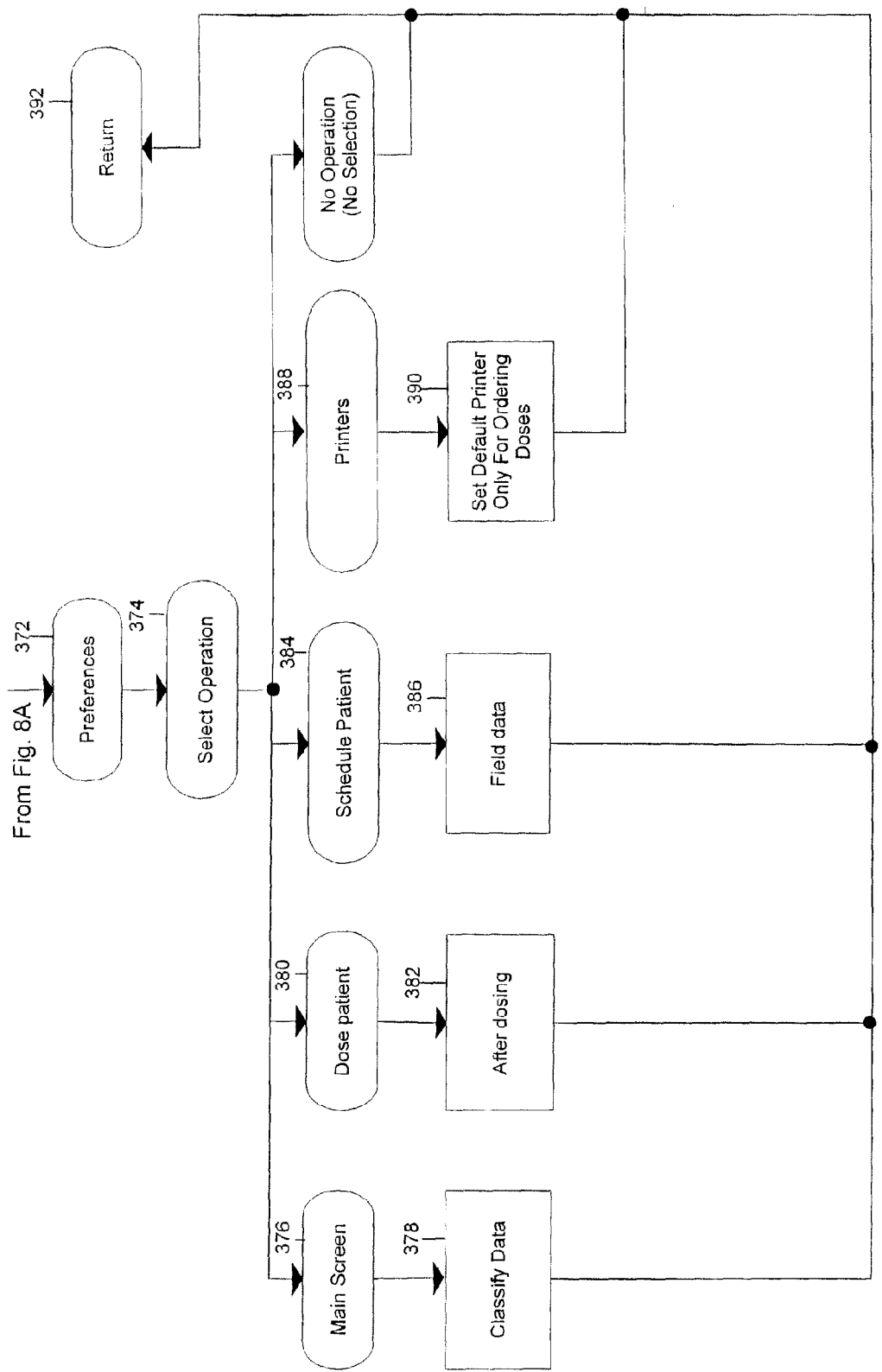
Figure 9:
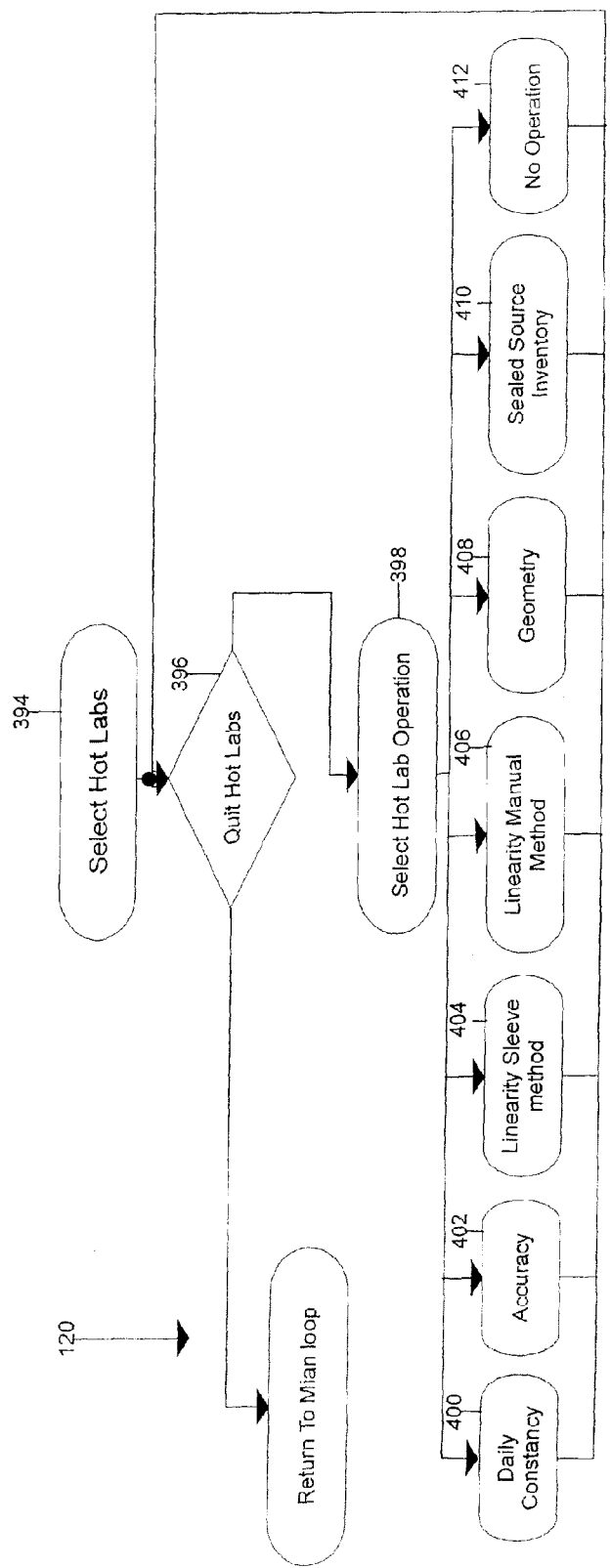
Figure 10:
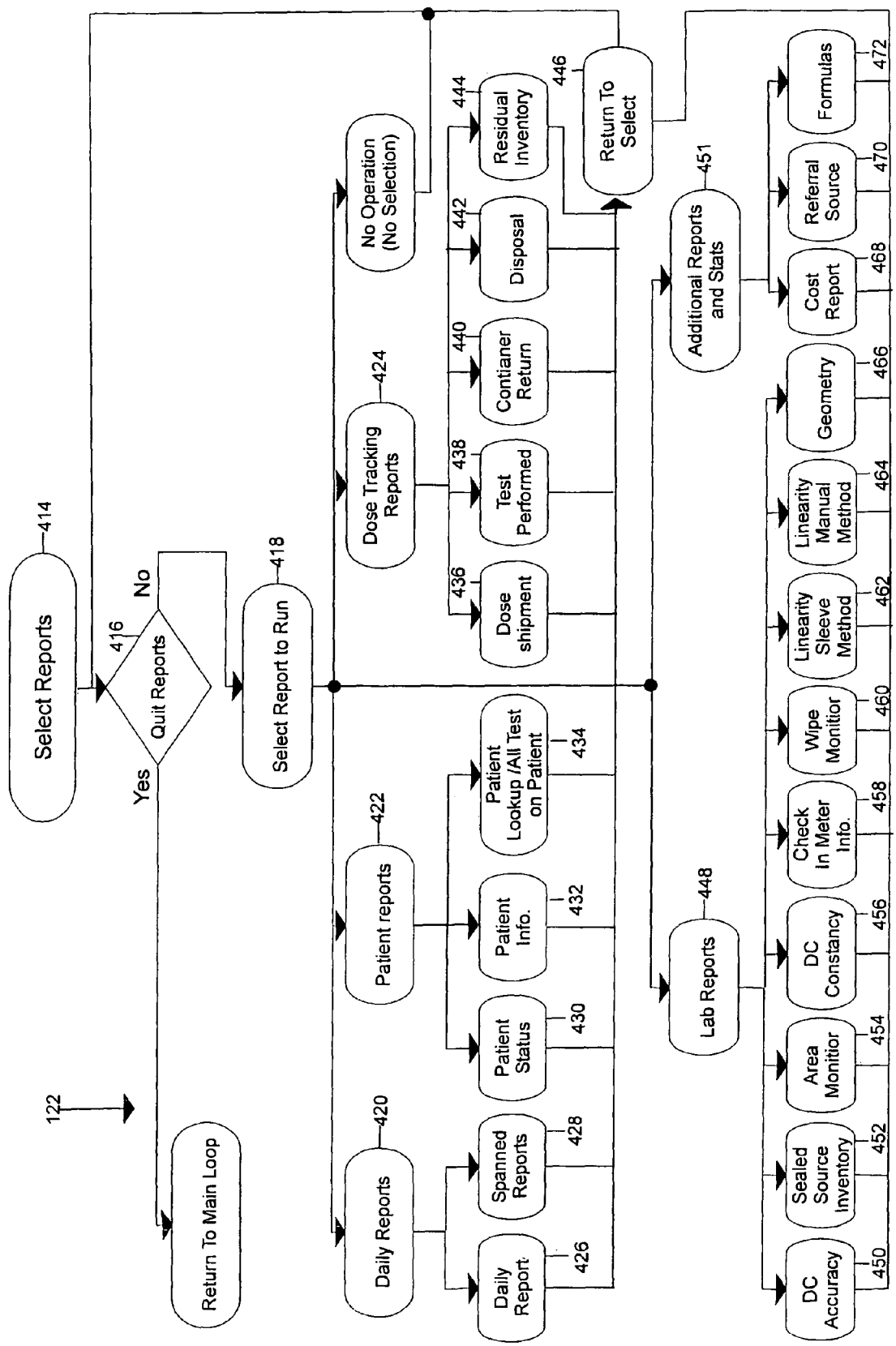
Figure 11:
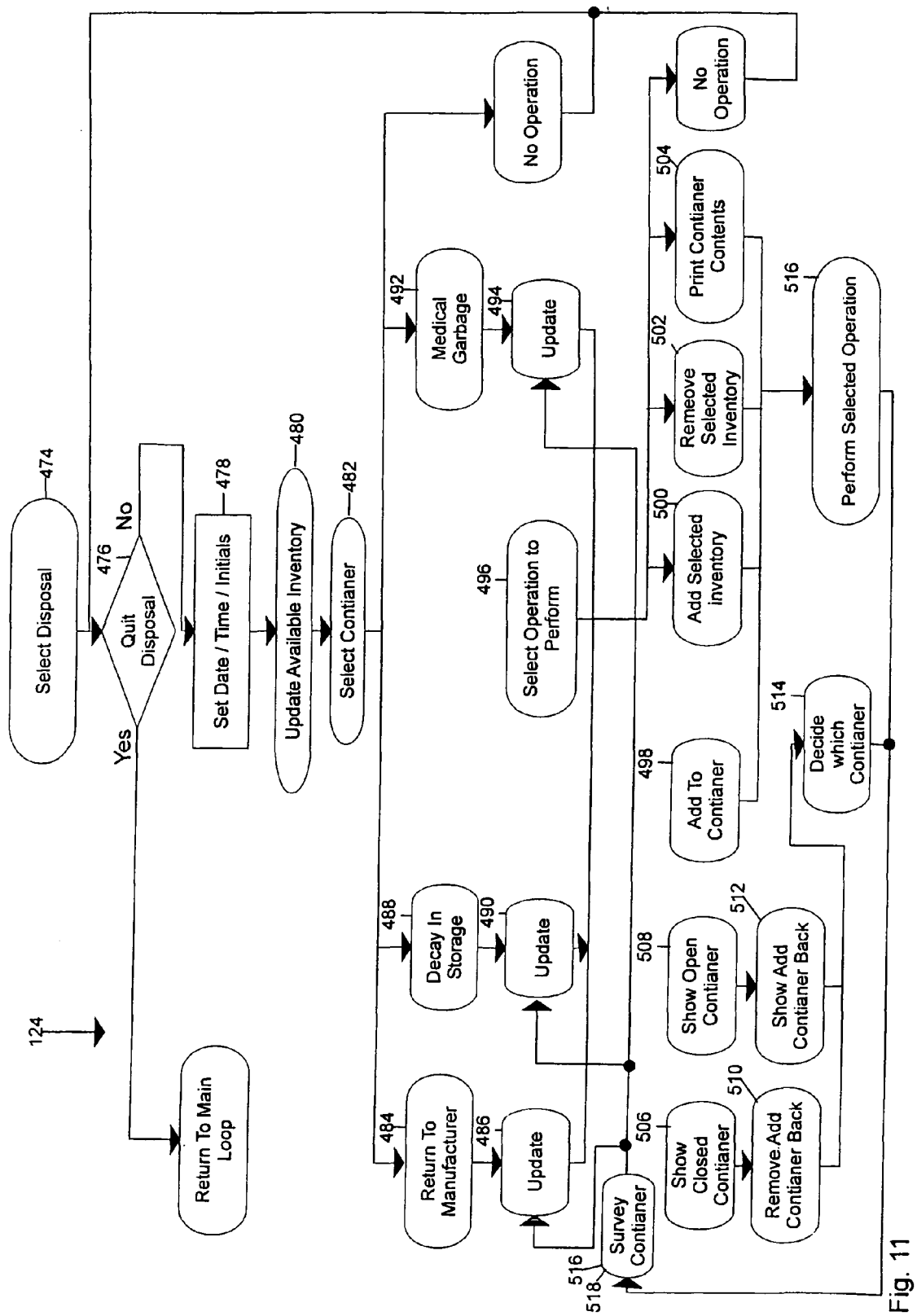
Figure 12:
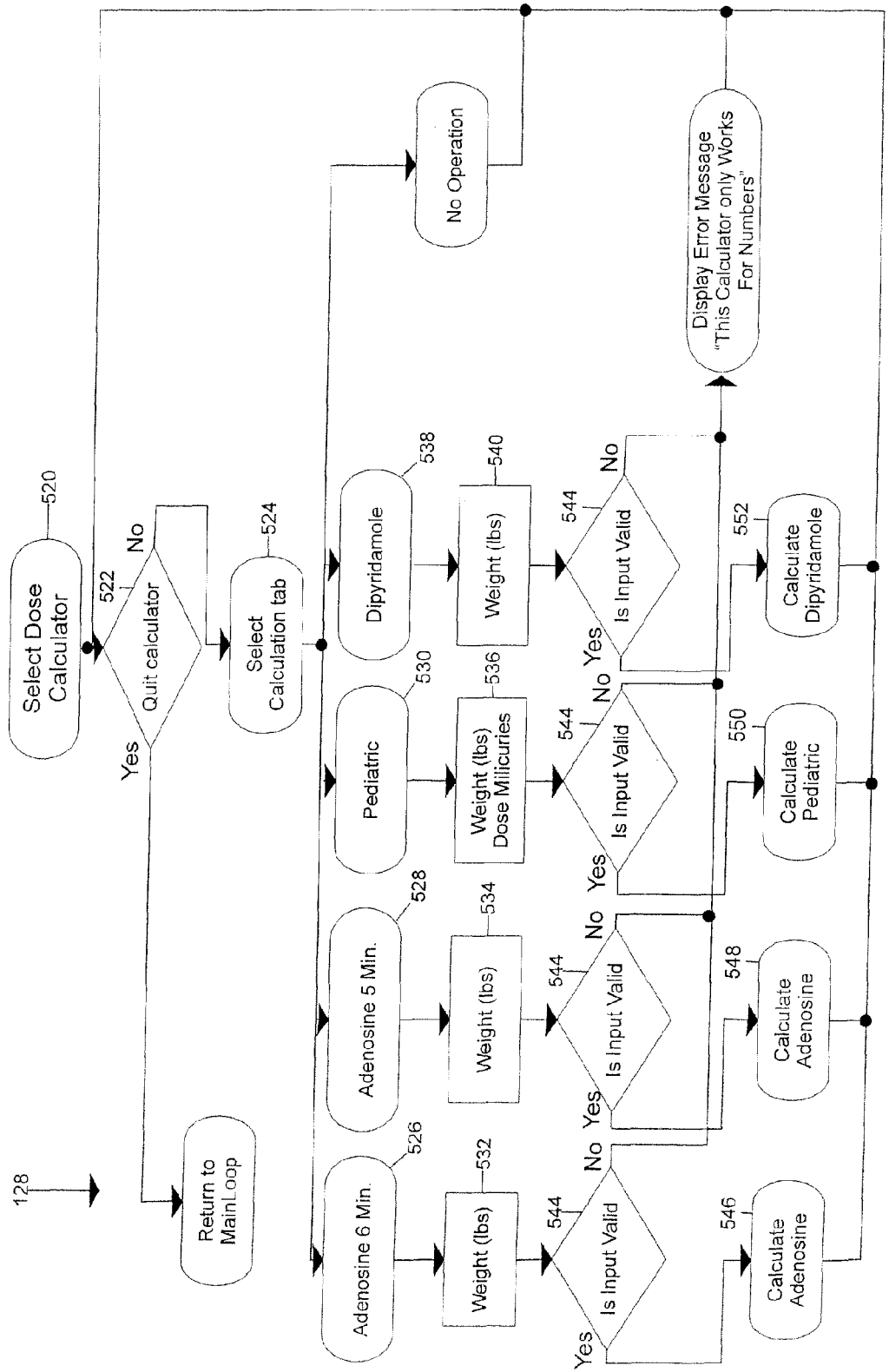
Figure 13:
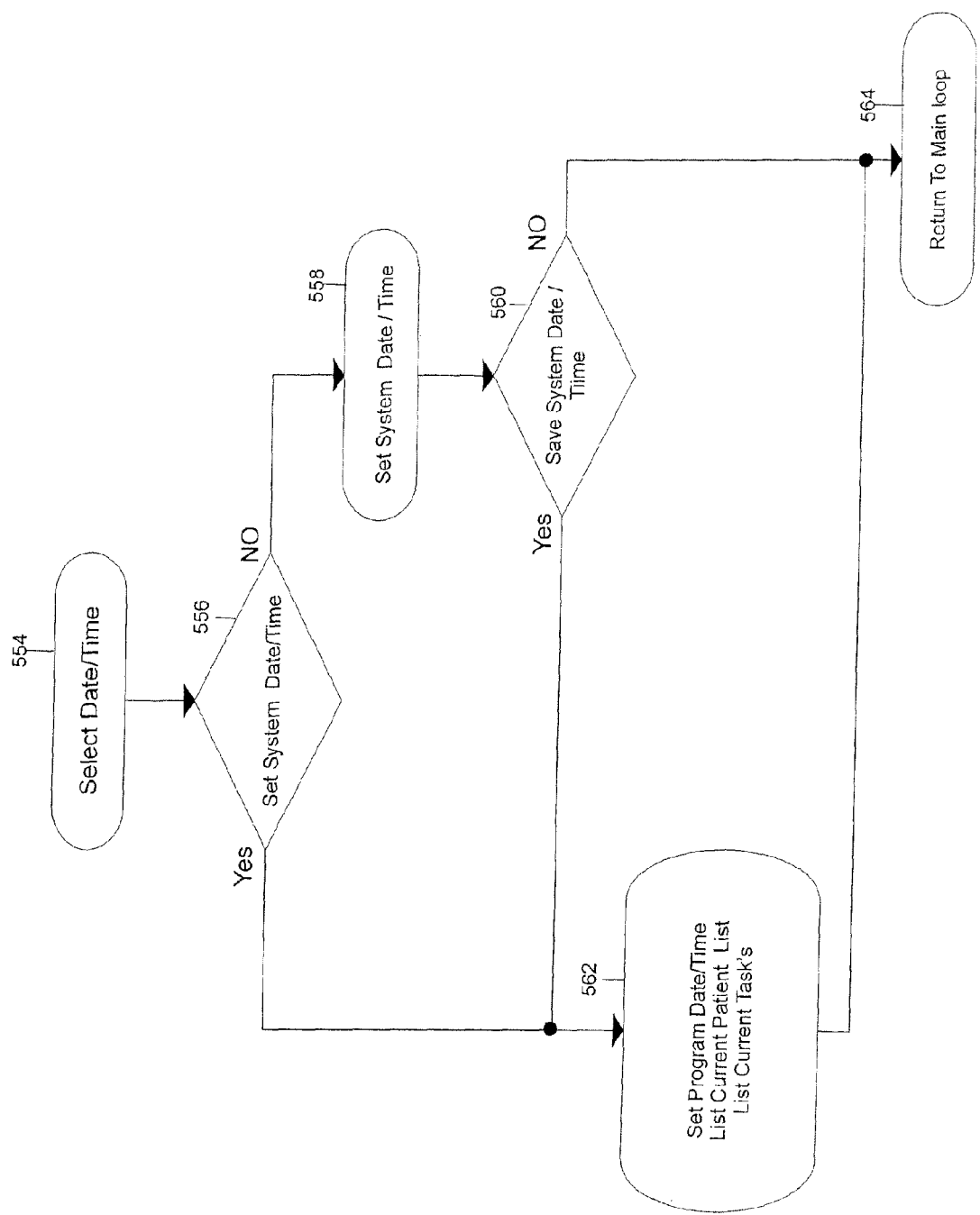
Figure 14:
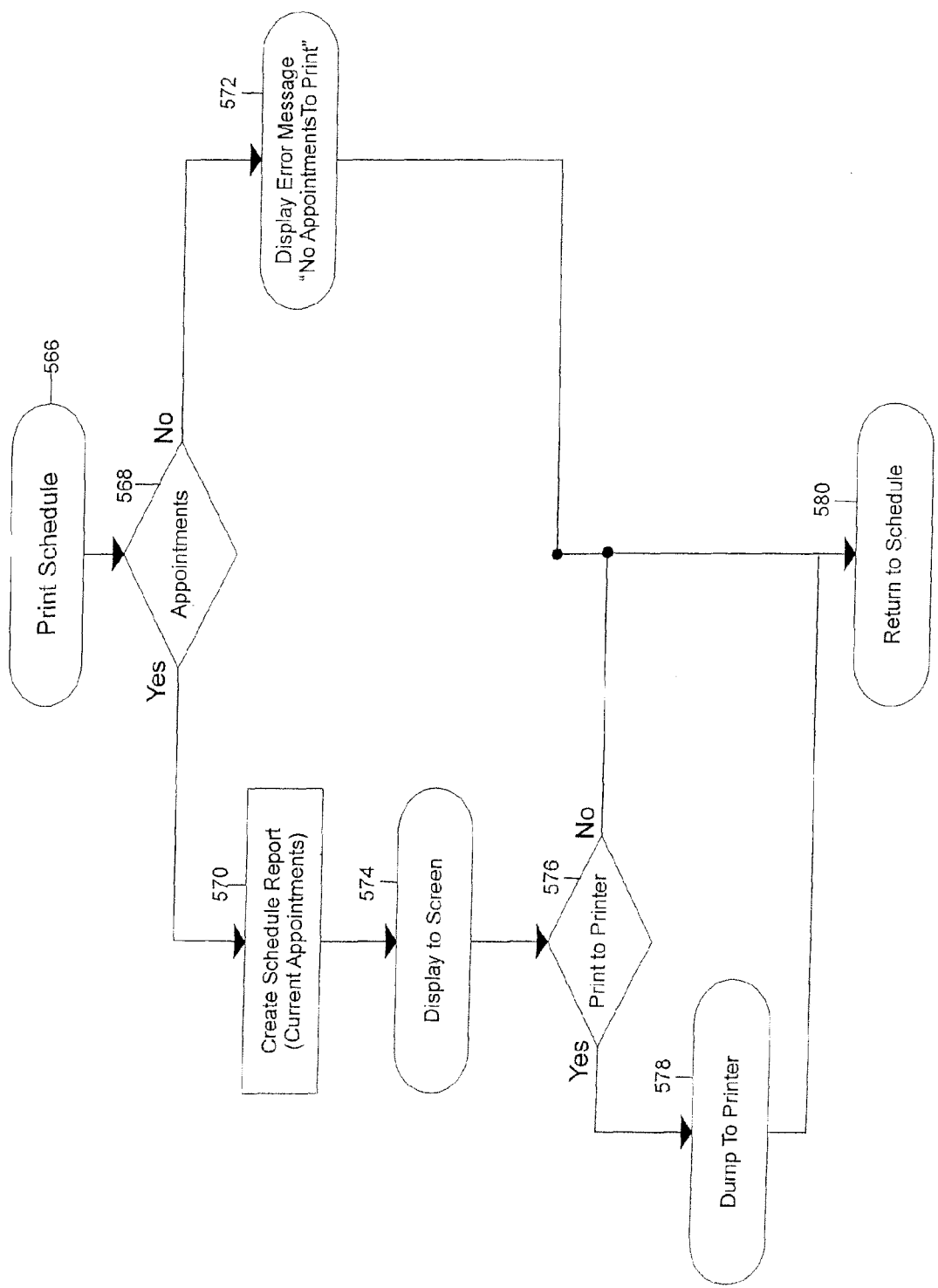
Figure 15A:
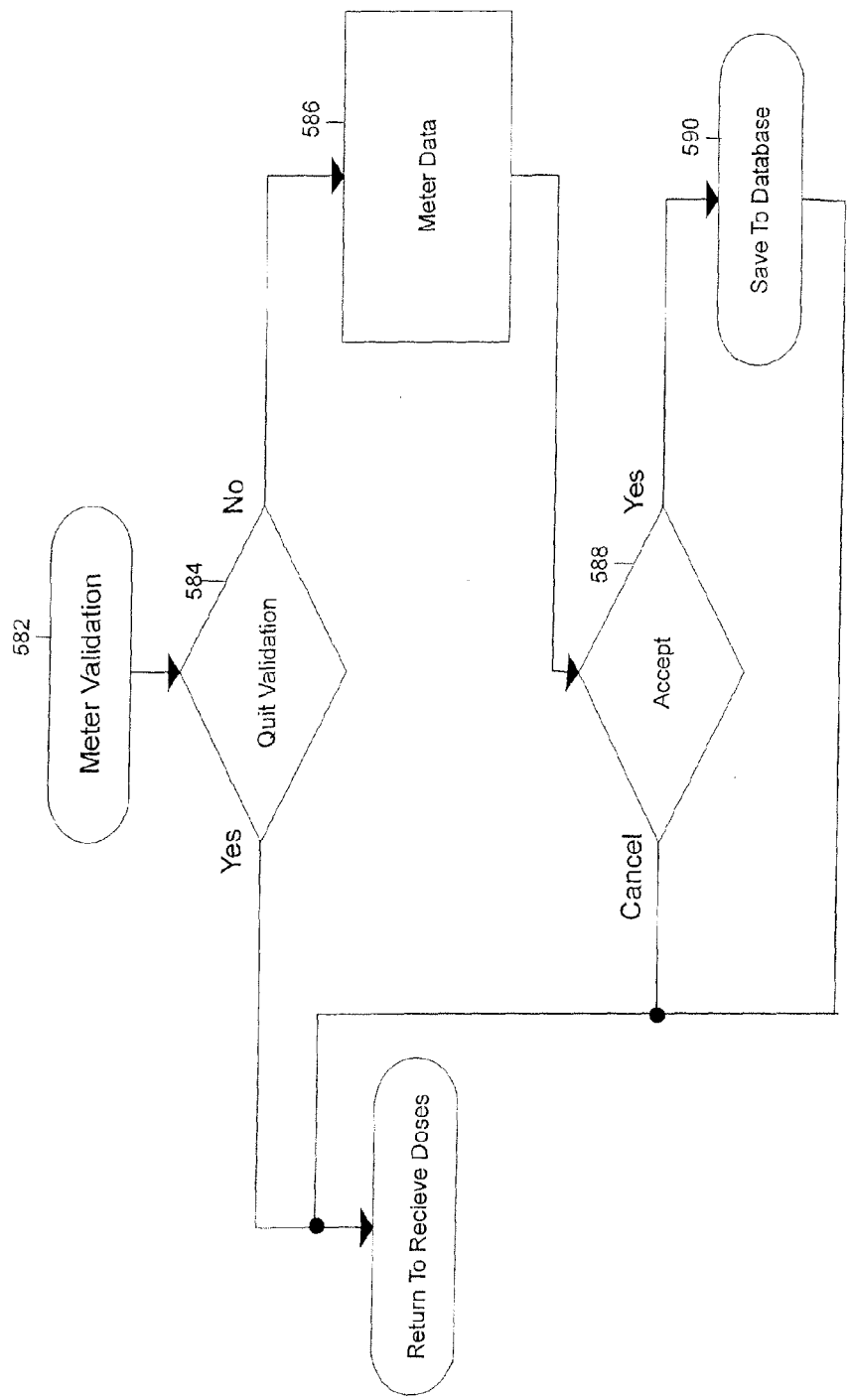
Figure 15B:
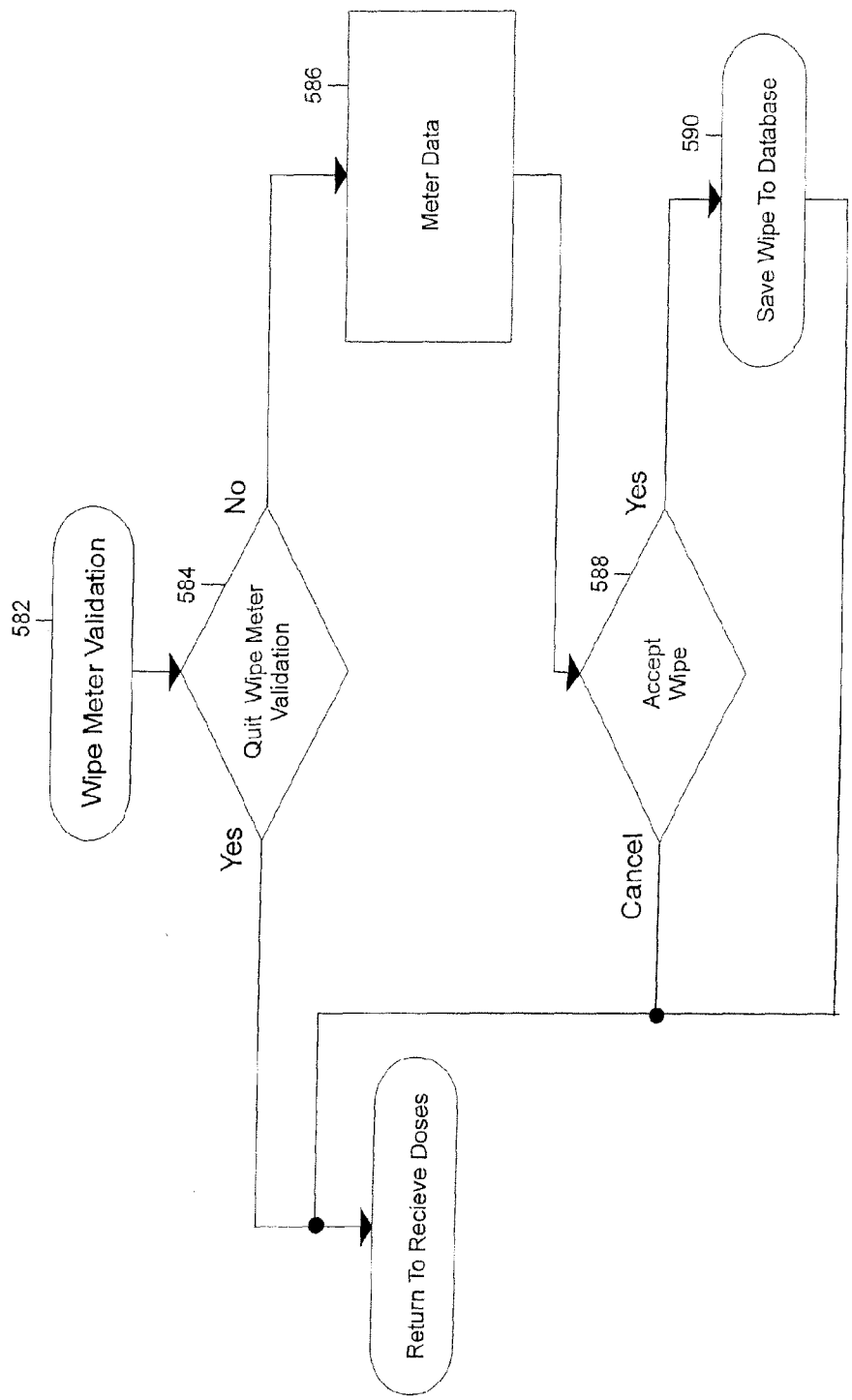
Figure 16:
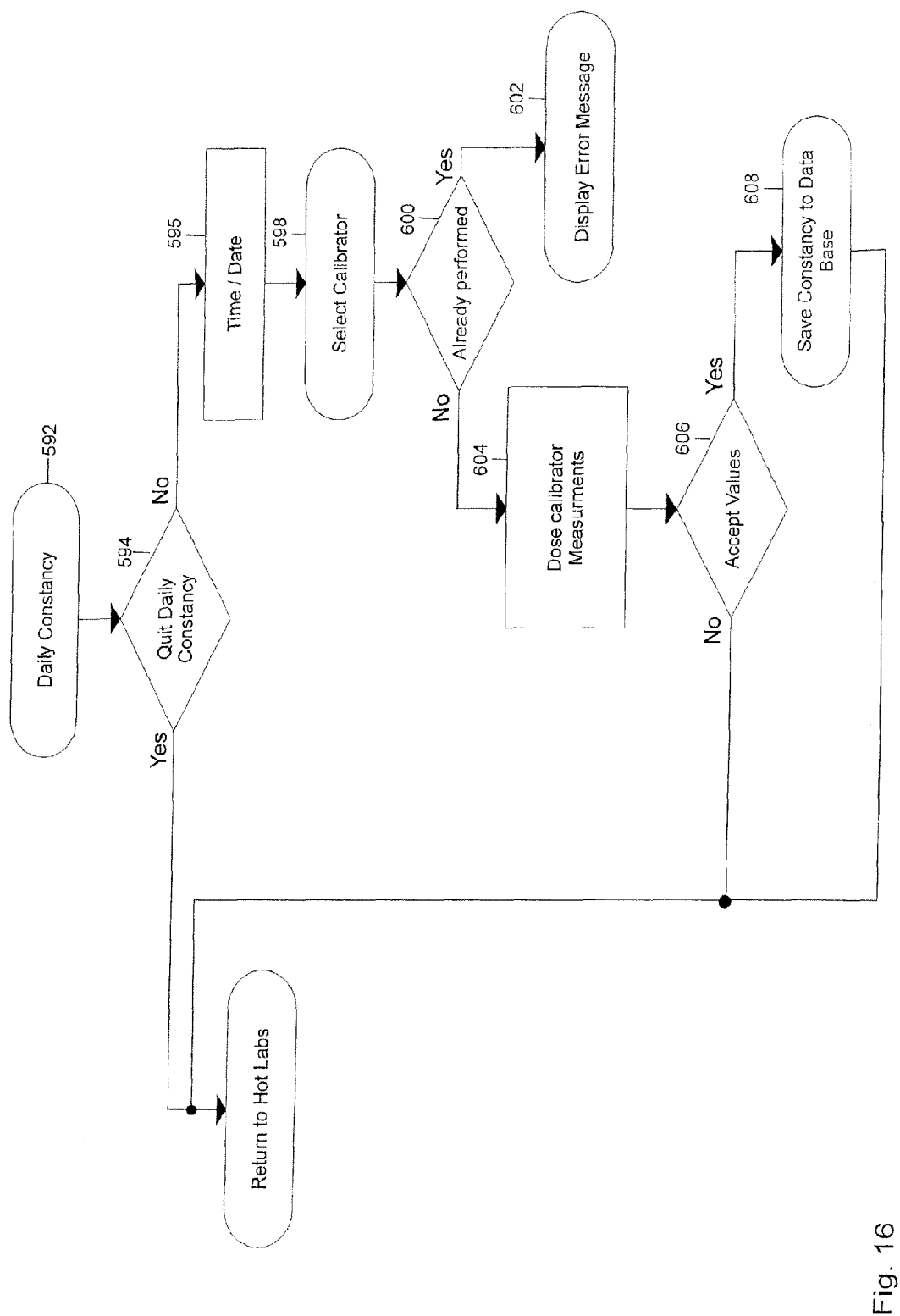
Figure 17:
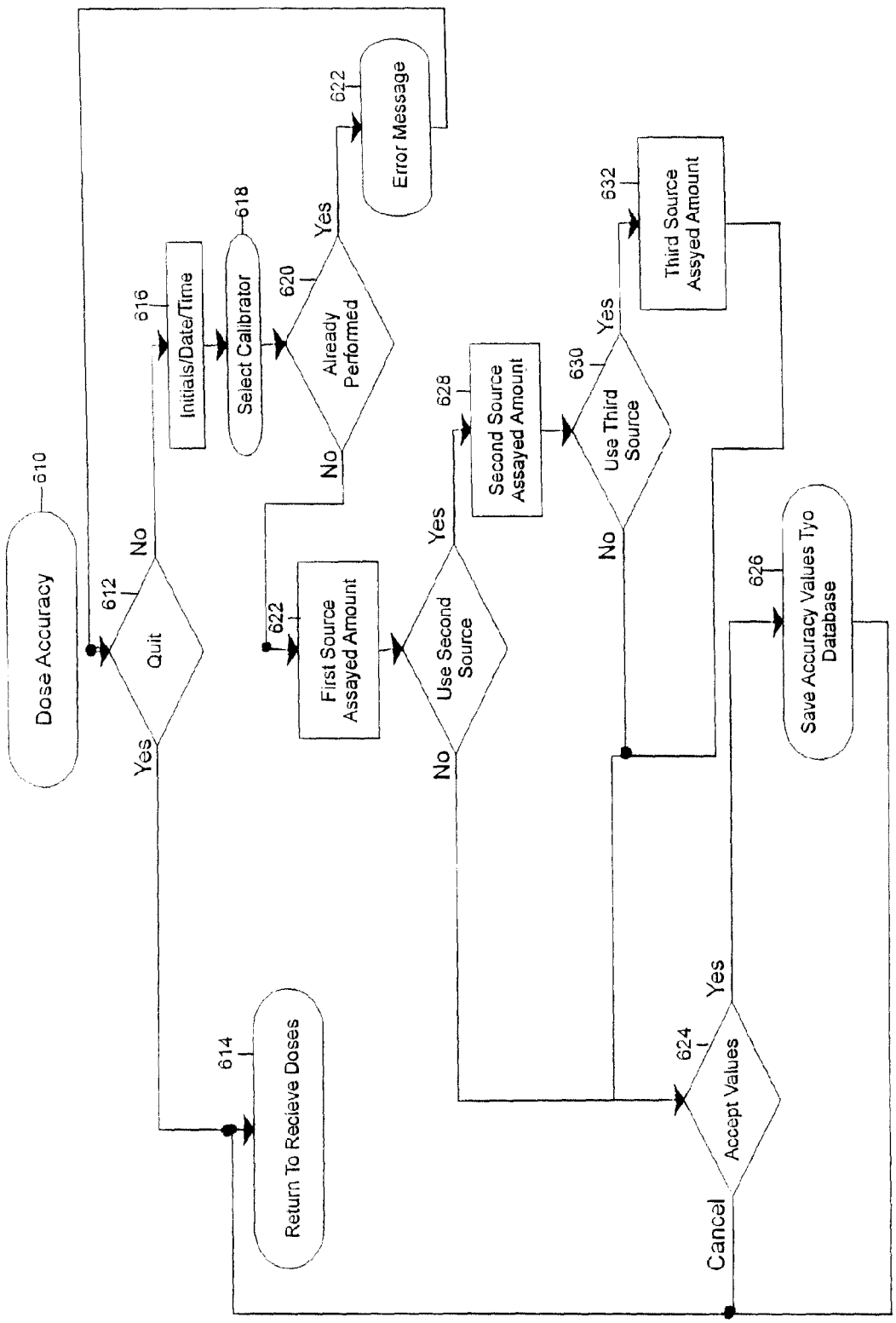
Figure 18:
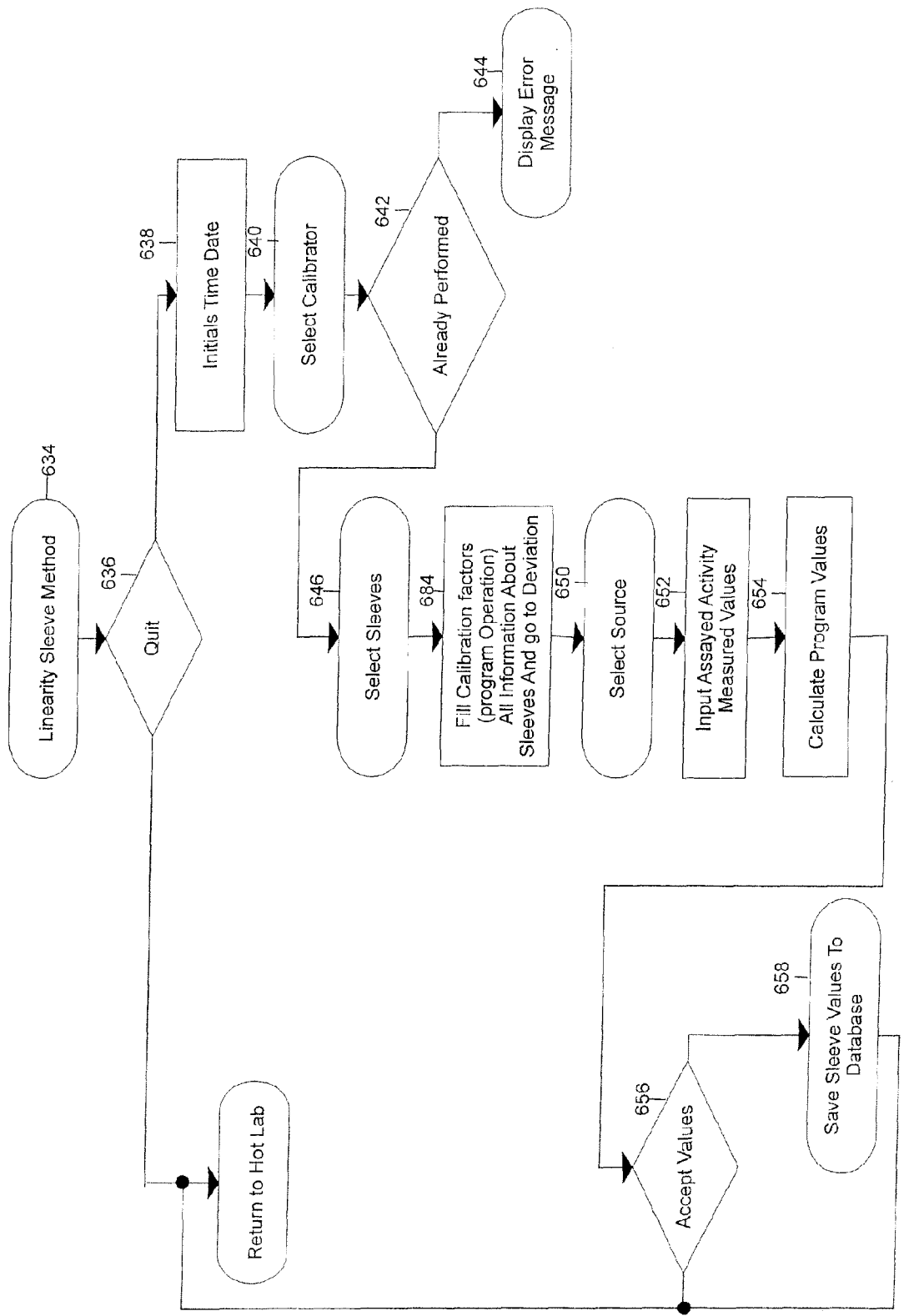
Figure 19:
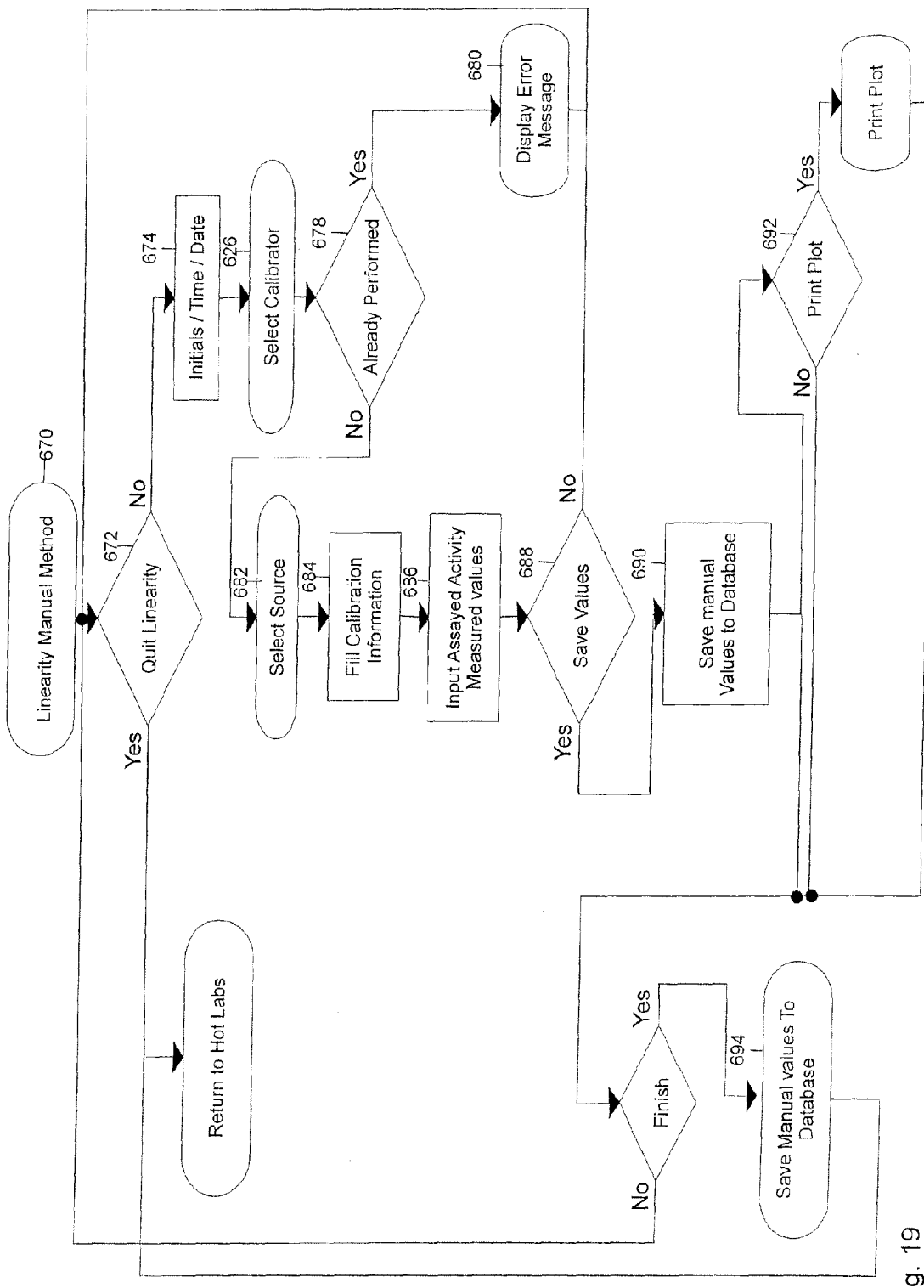
Figure 20:
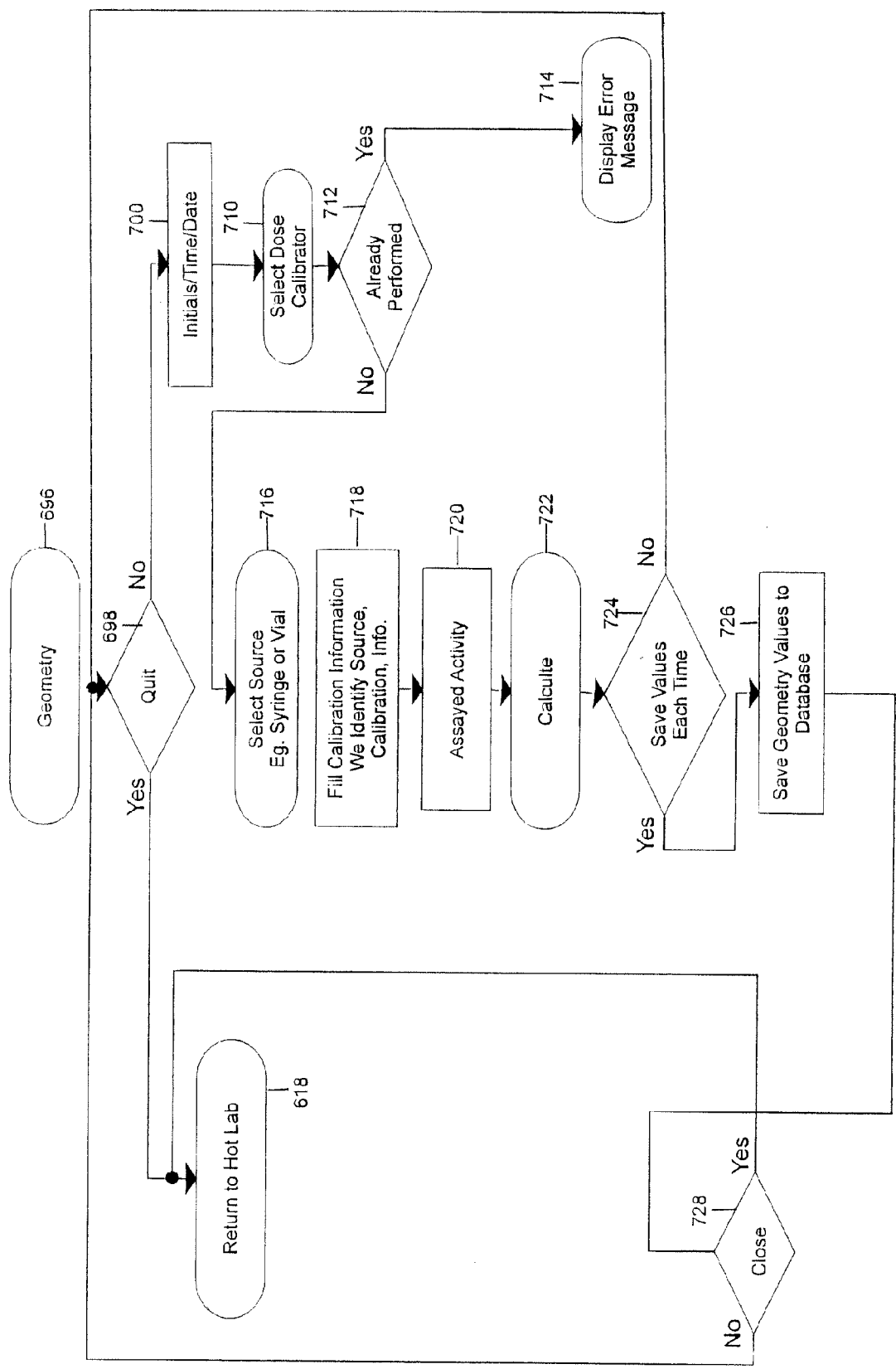
Figure 21:
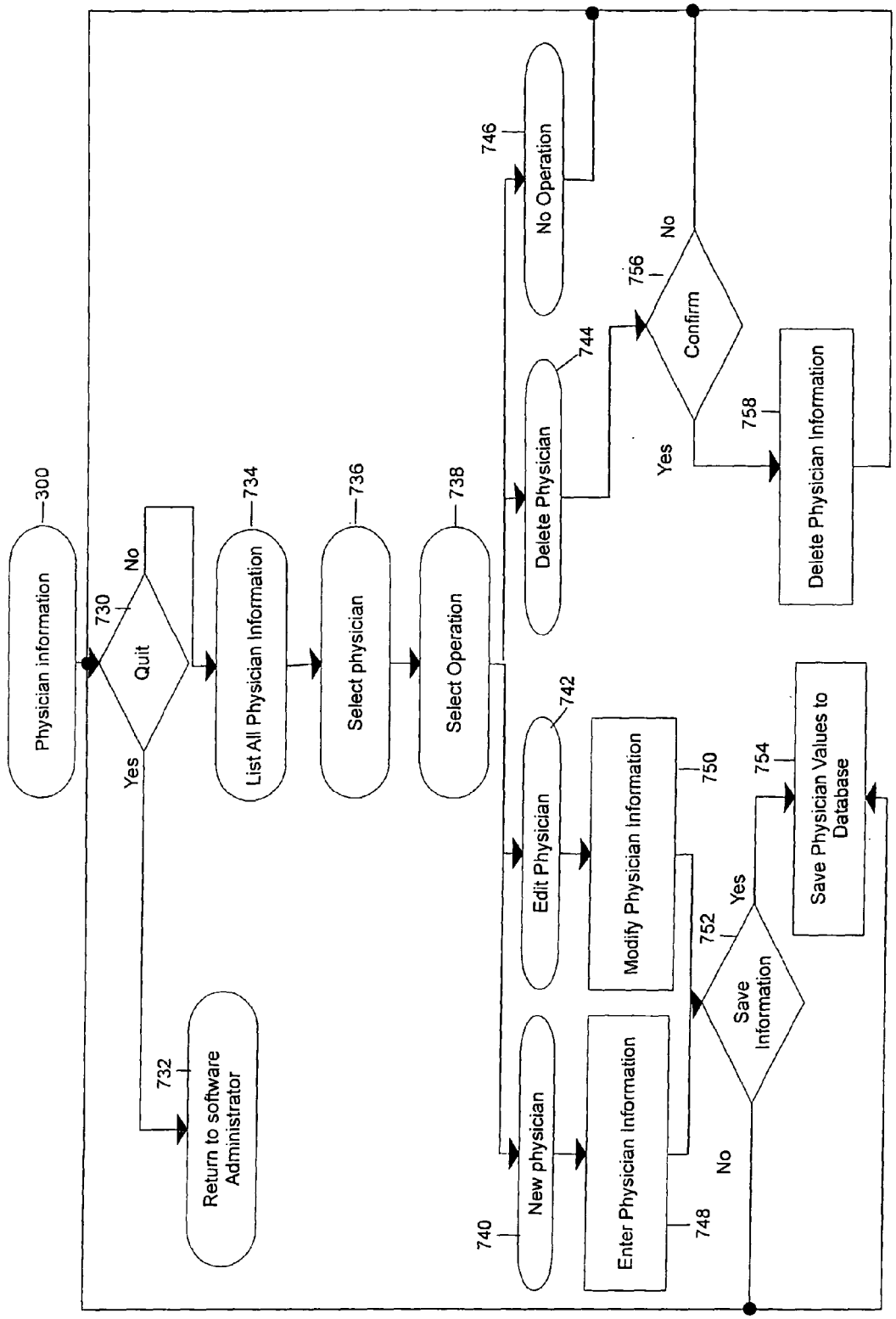
Figure 22:
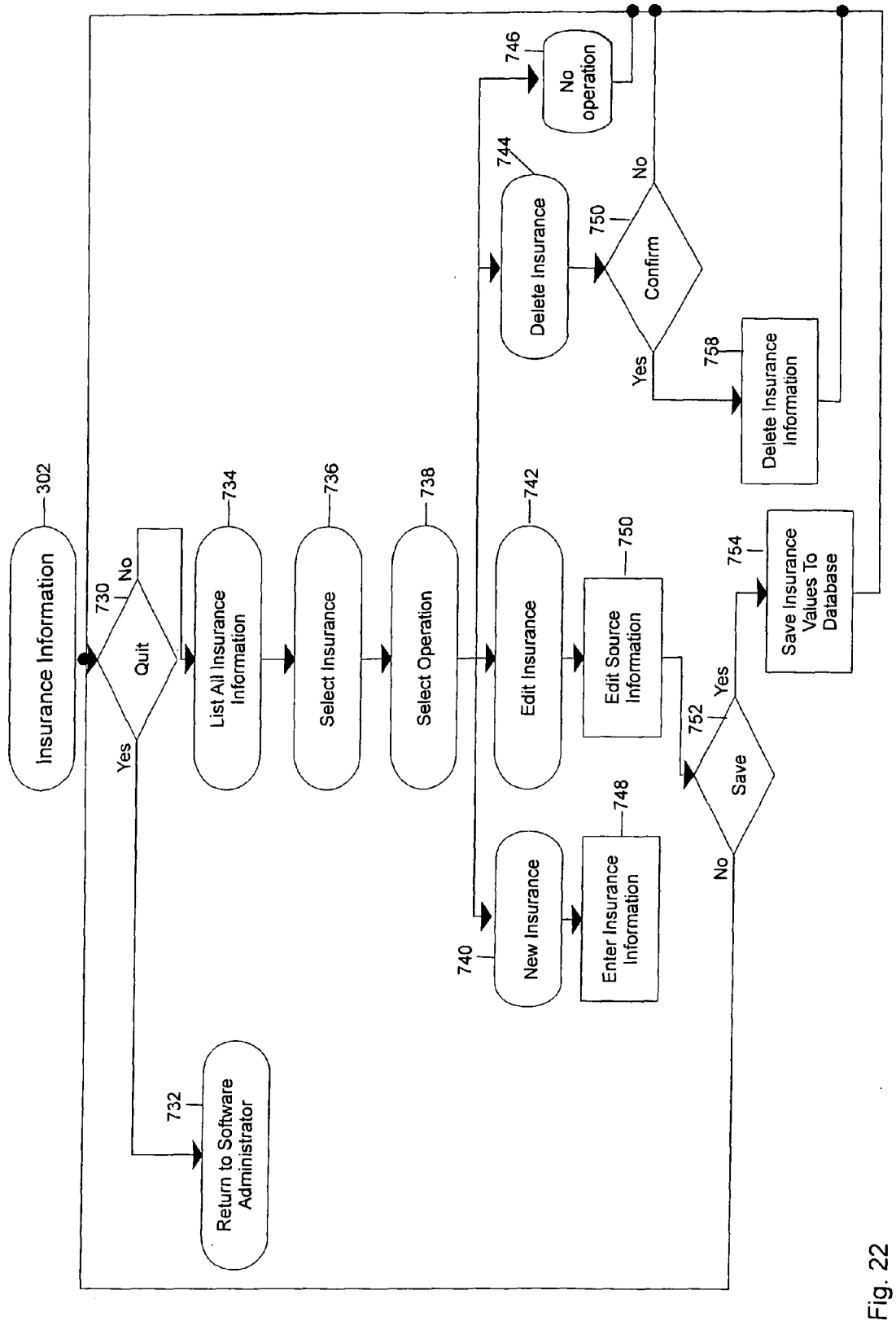
Figure 23:
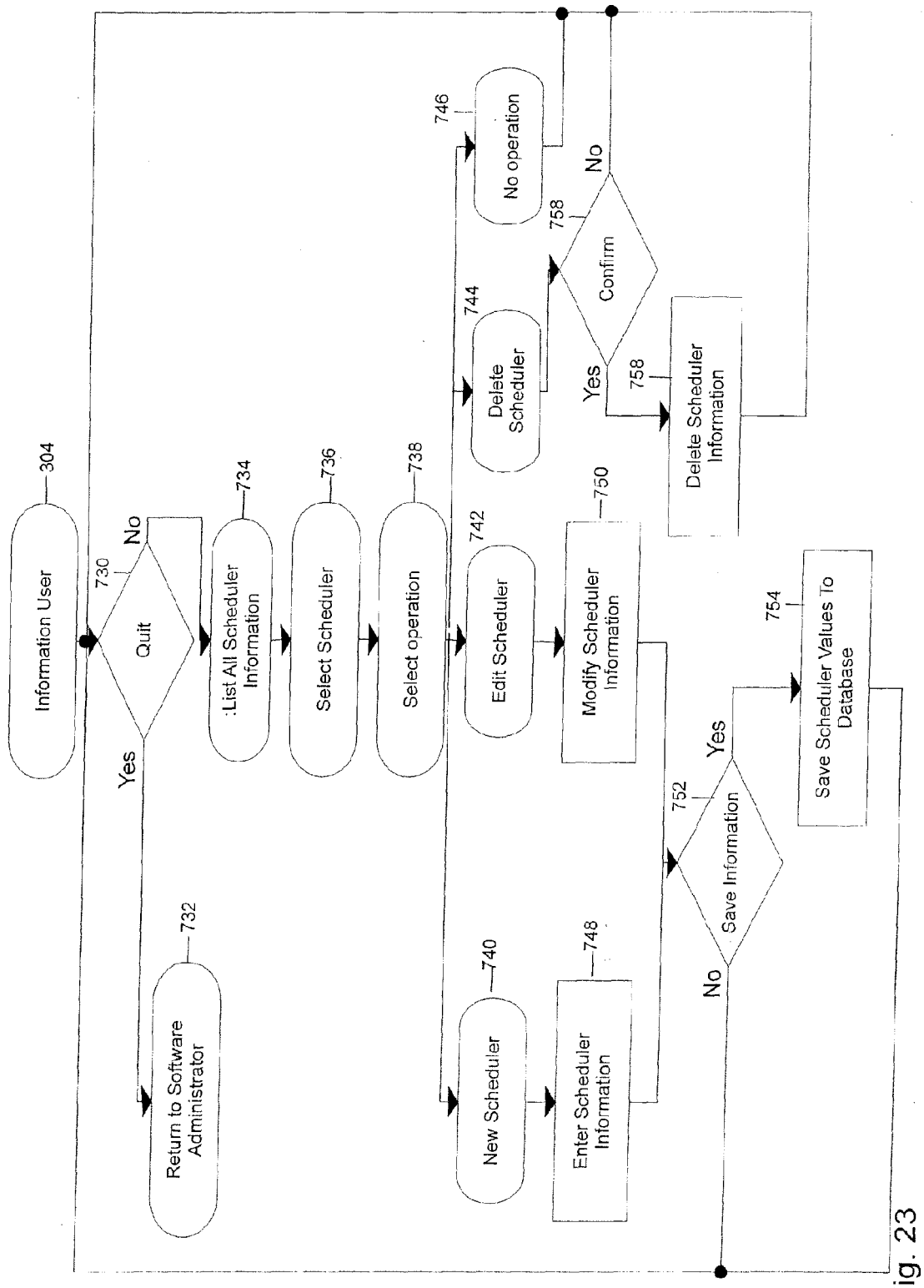
Figure 24:
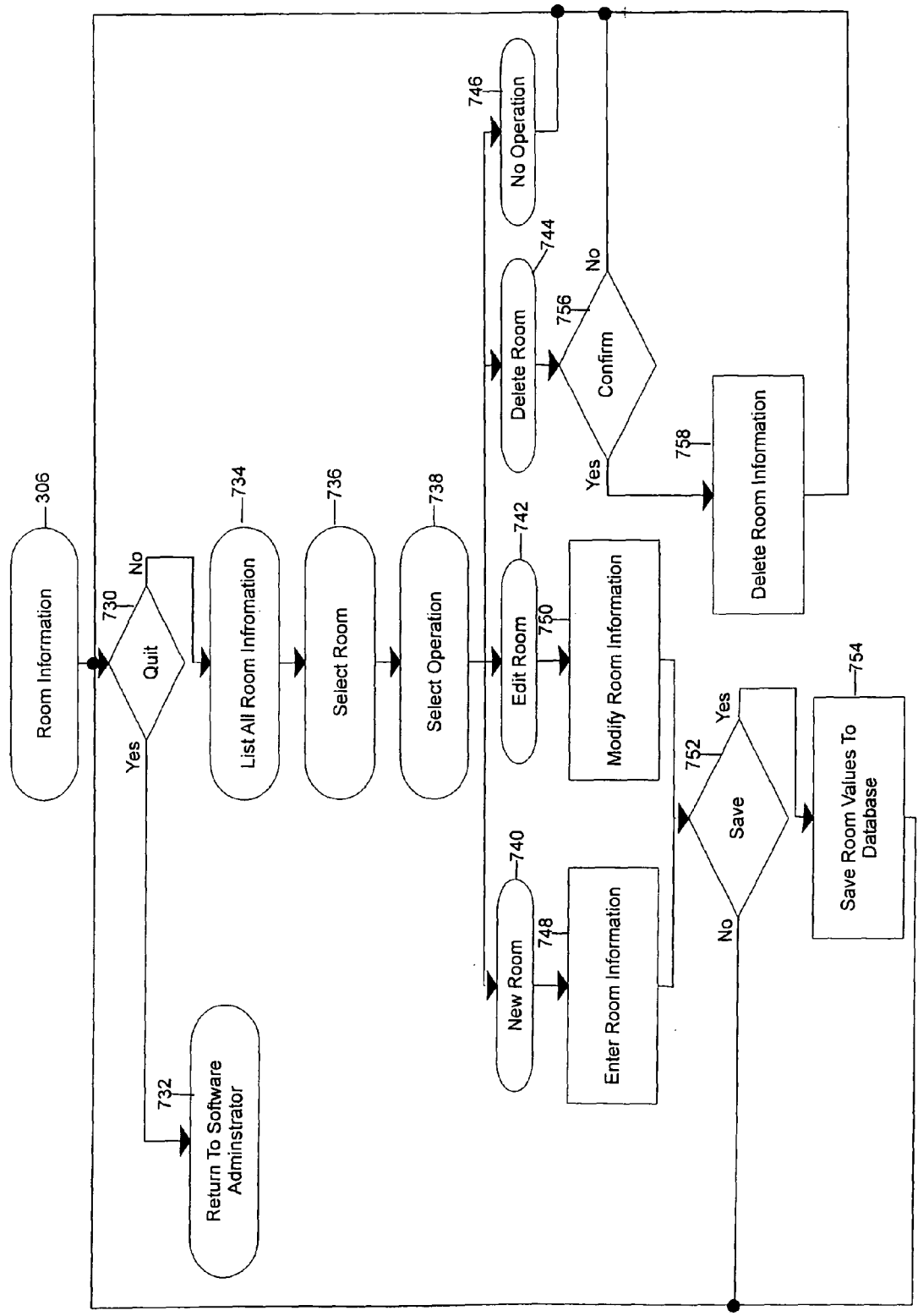
Figure 25:
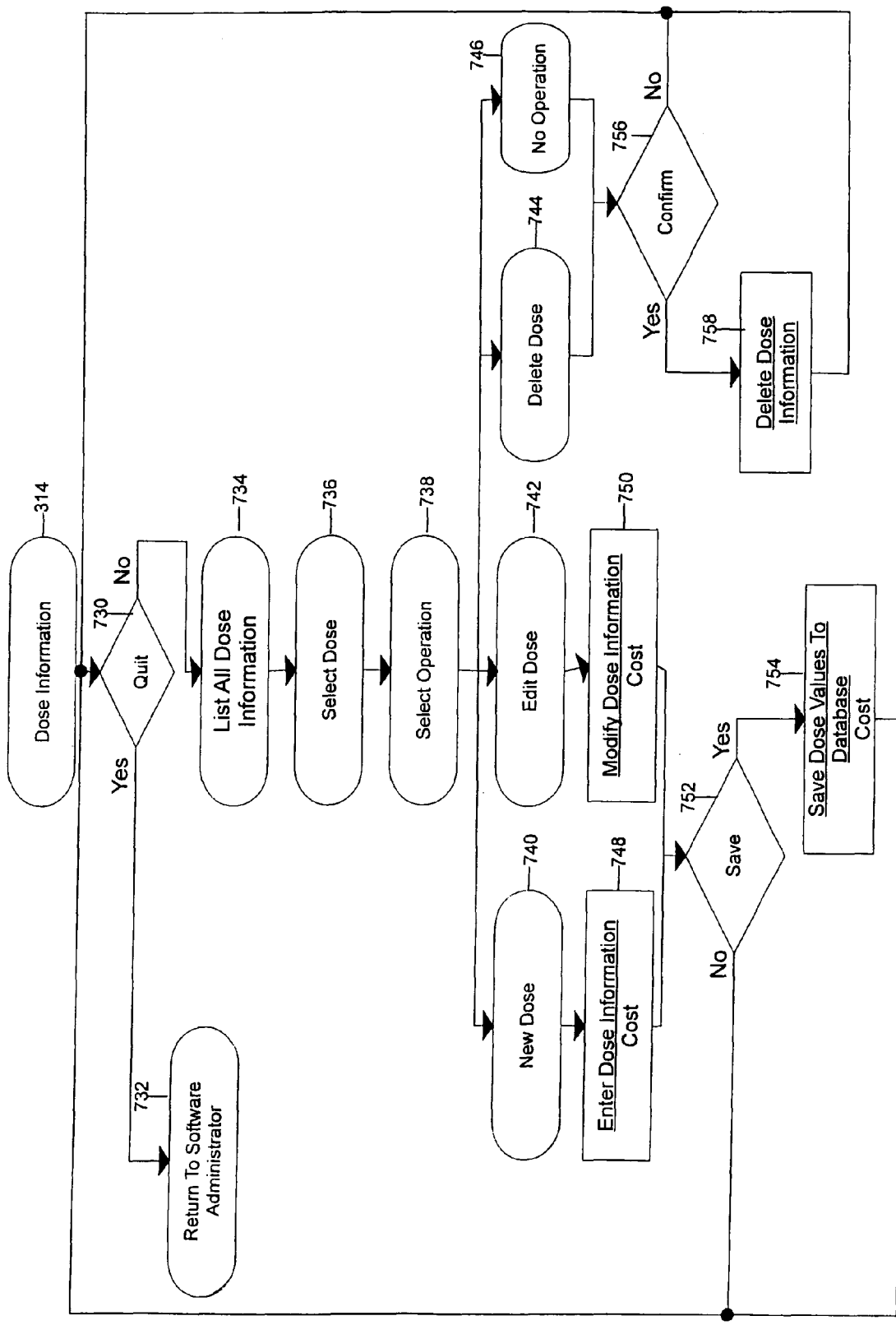
Figure 26:
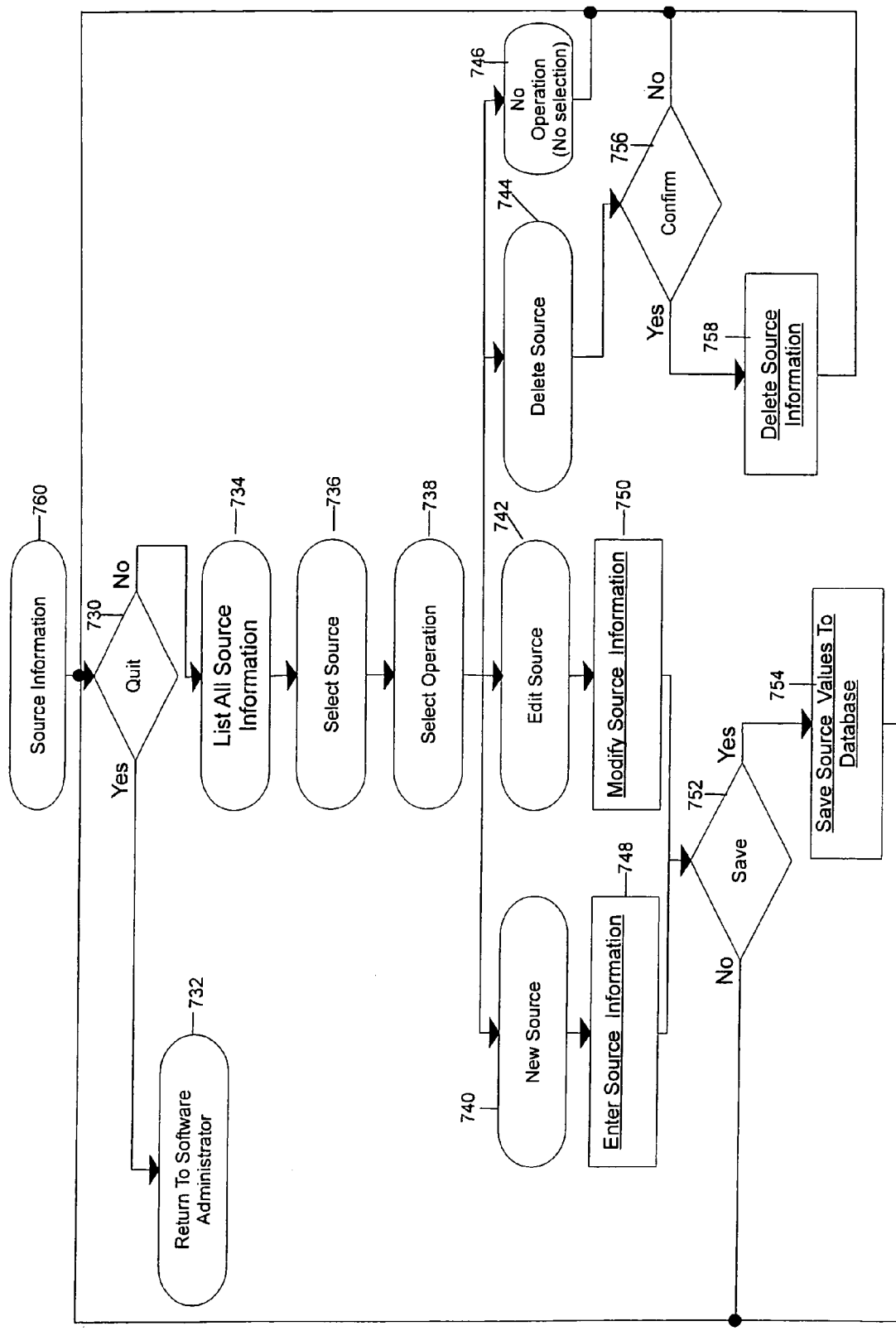
Figure 27:
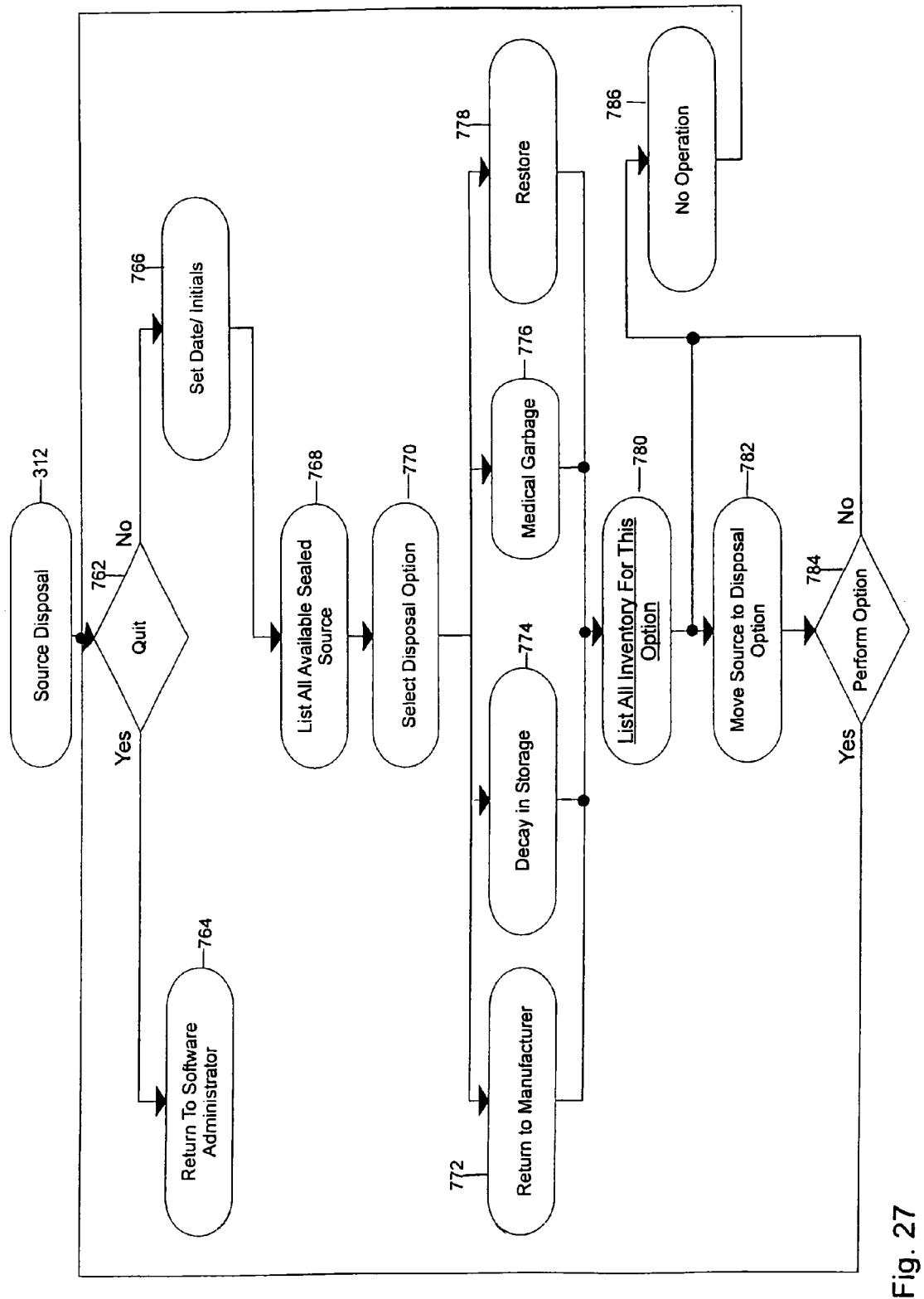
Figure 28:
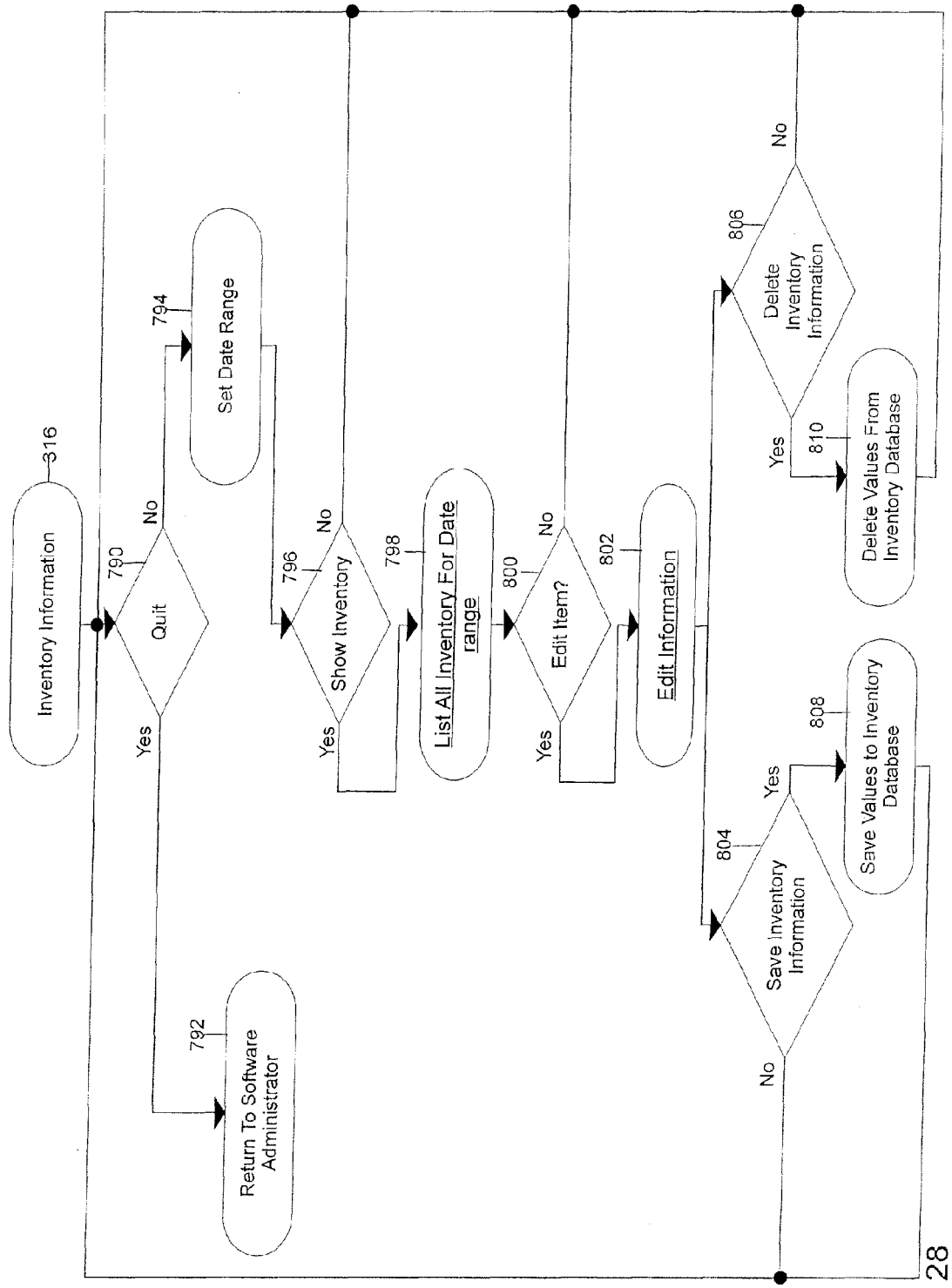
Figure 29:
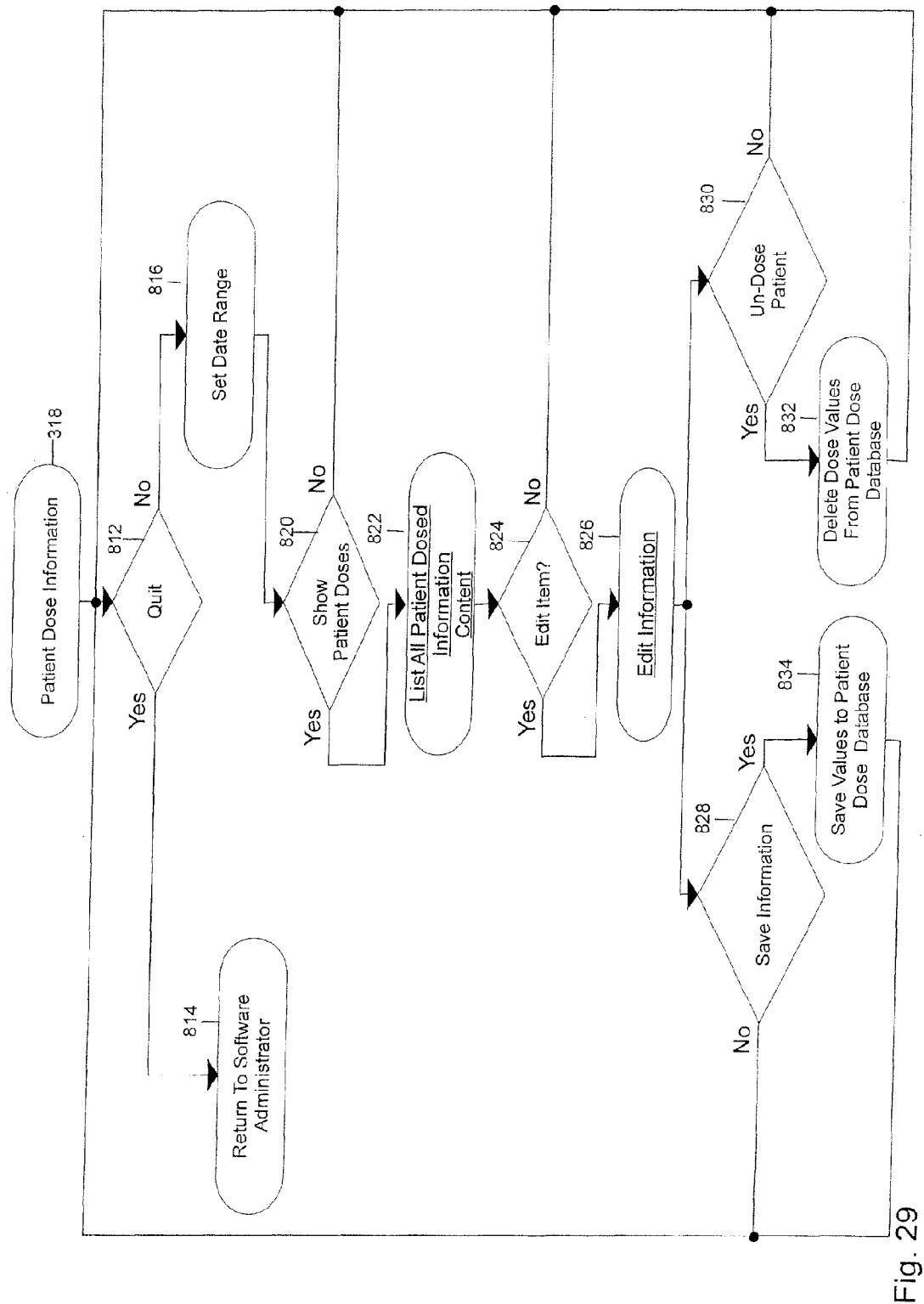
Figure 30:
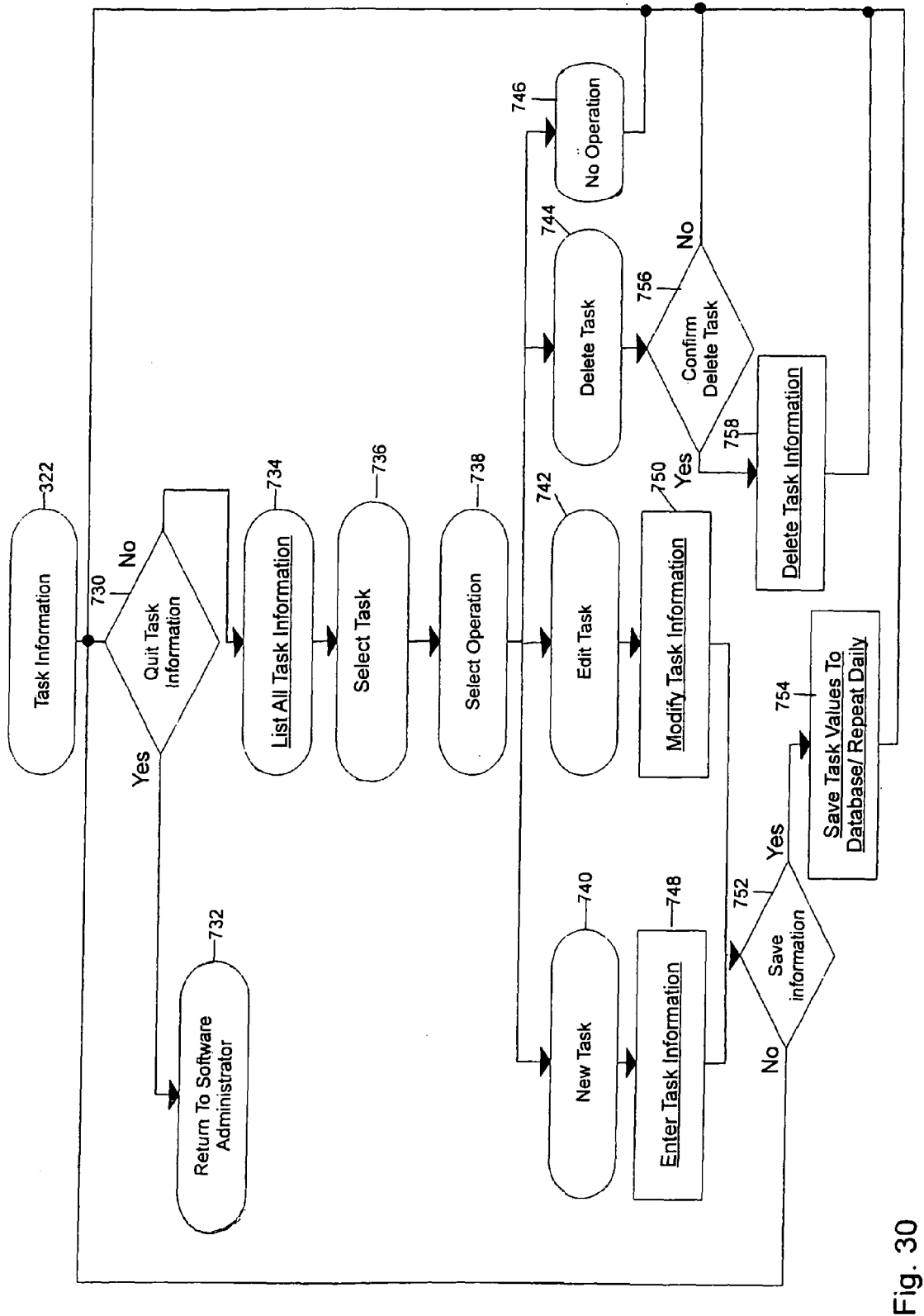
Figure 31:
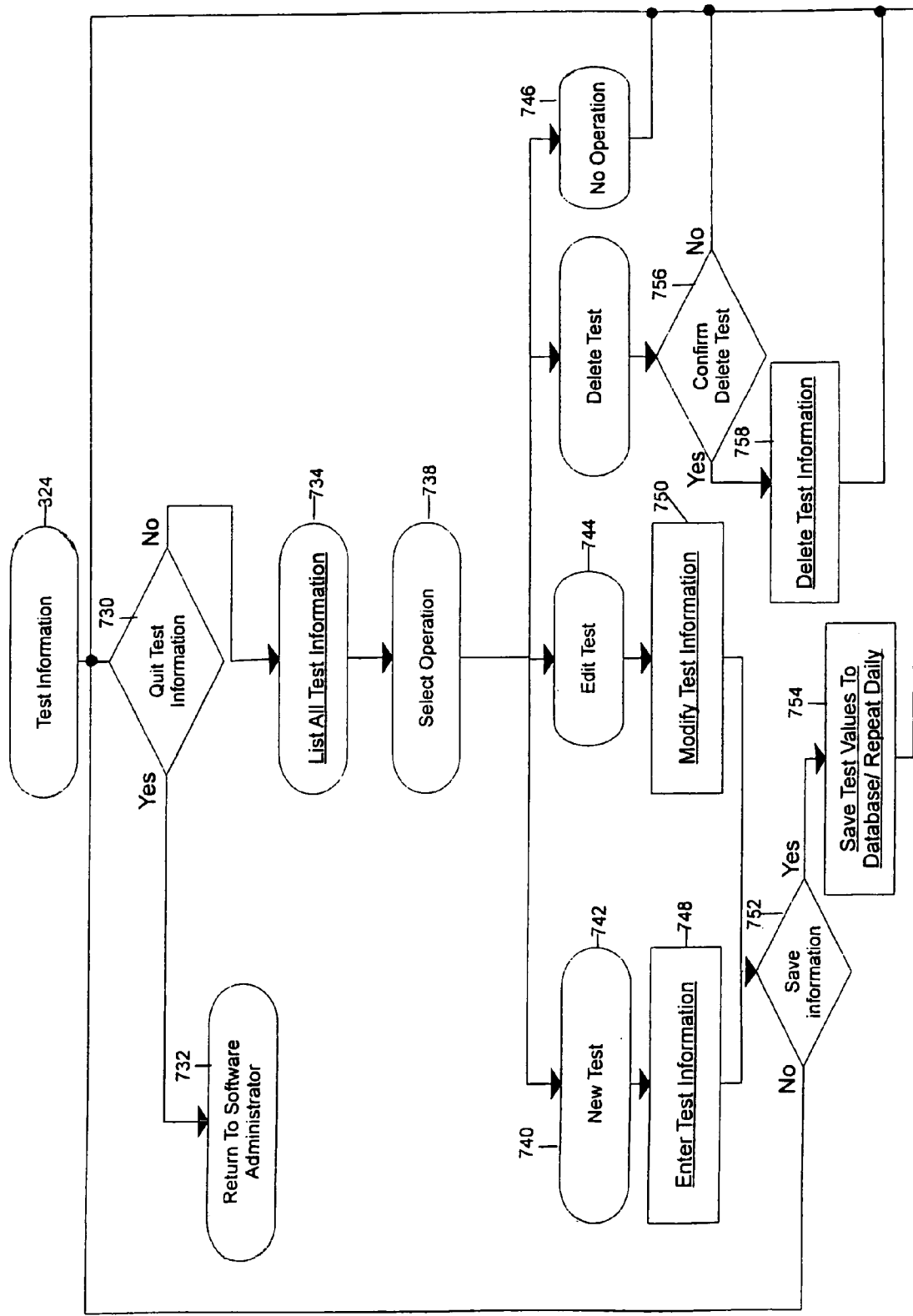
Figure 32:
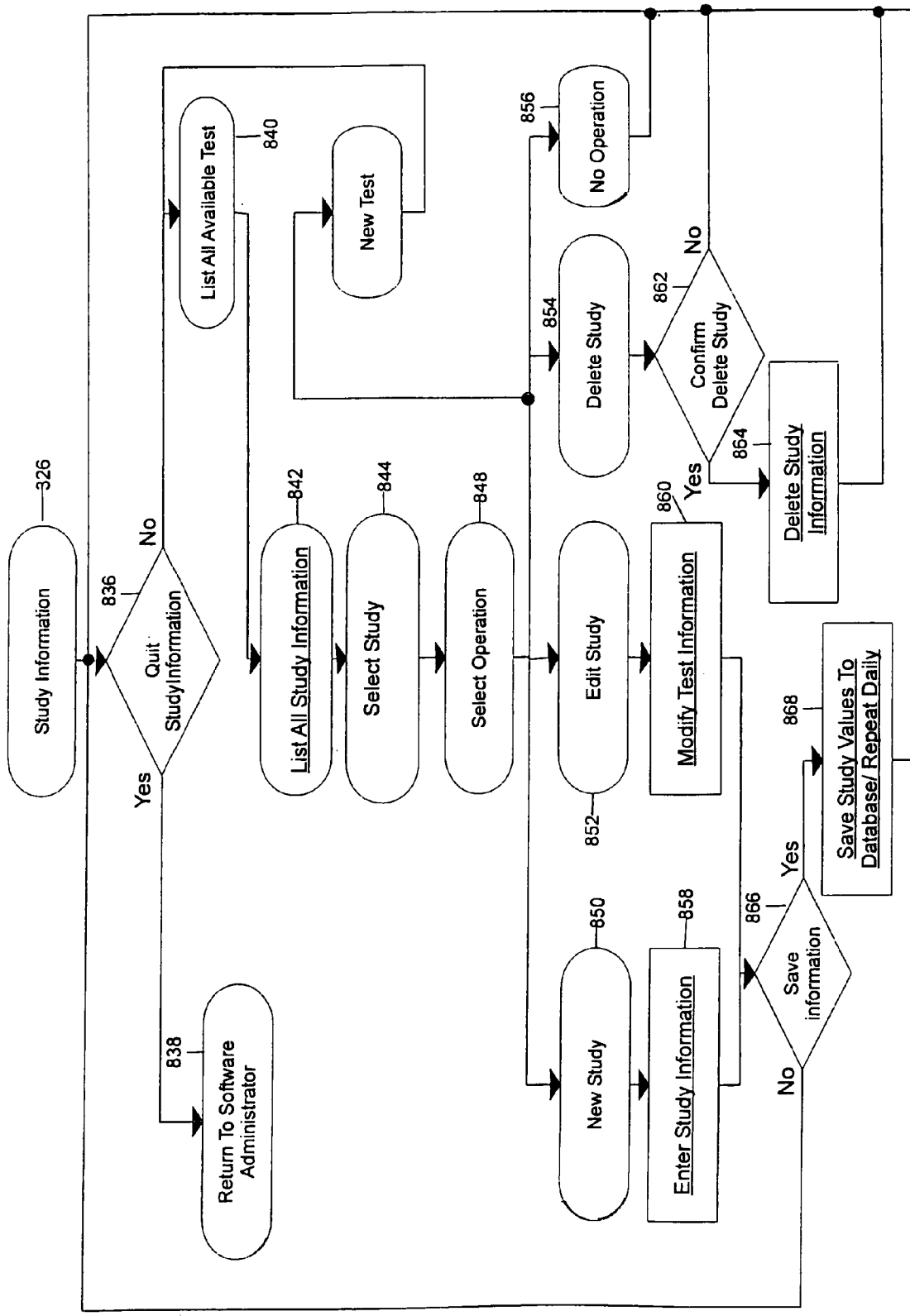
Figure 33:
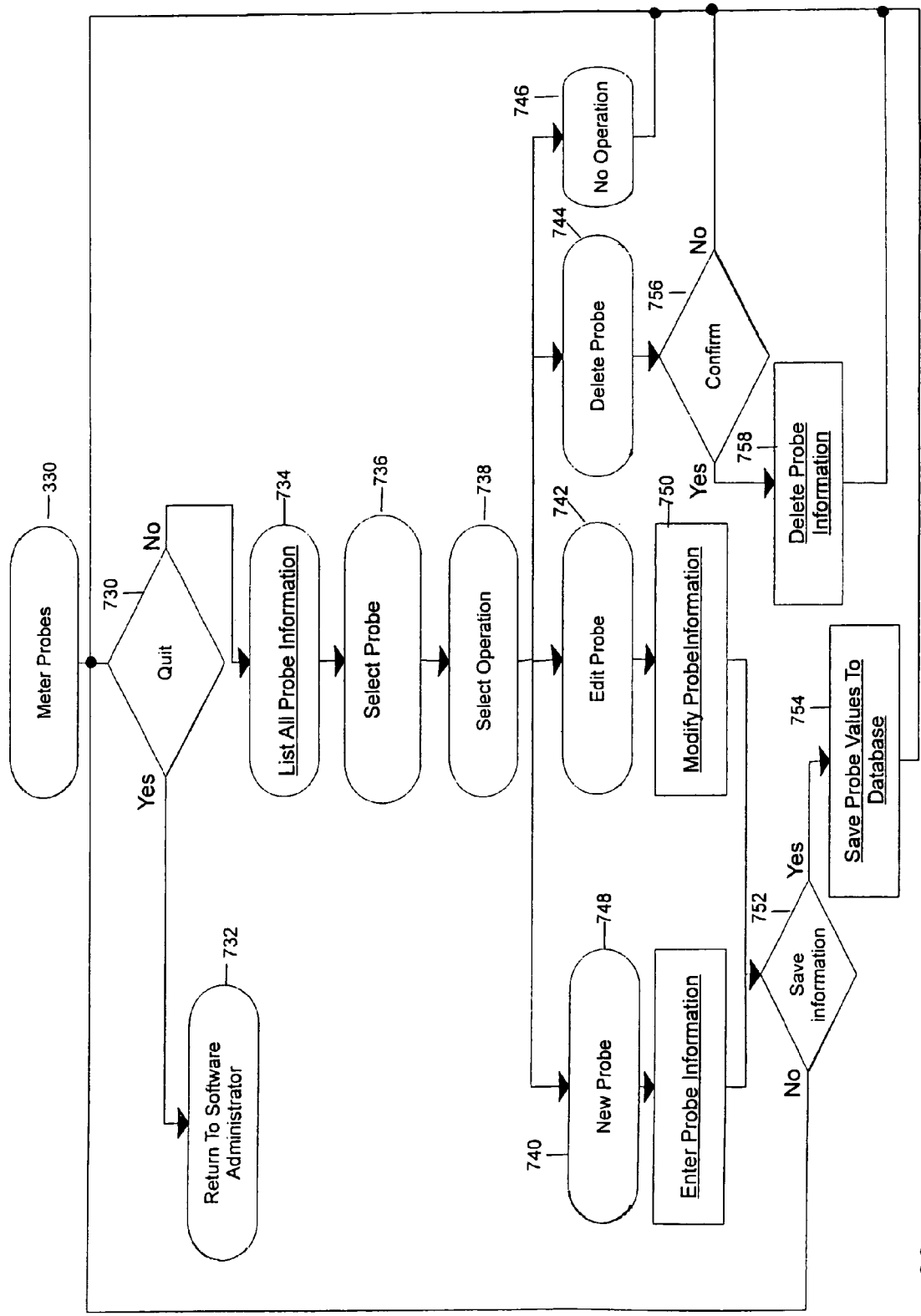
Figure 34:
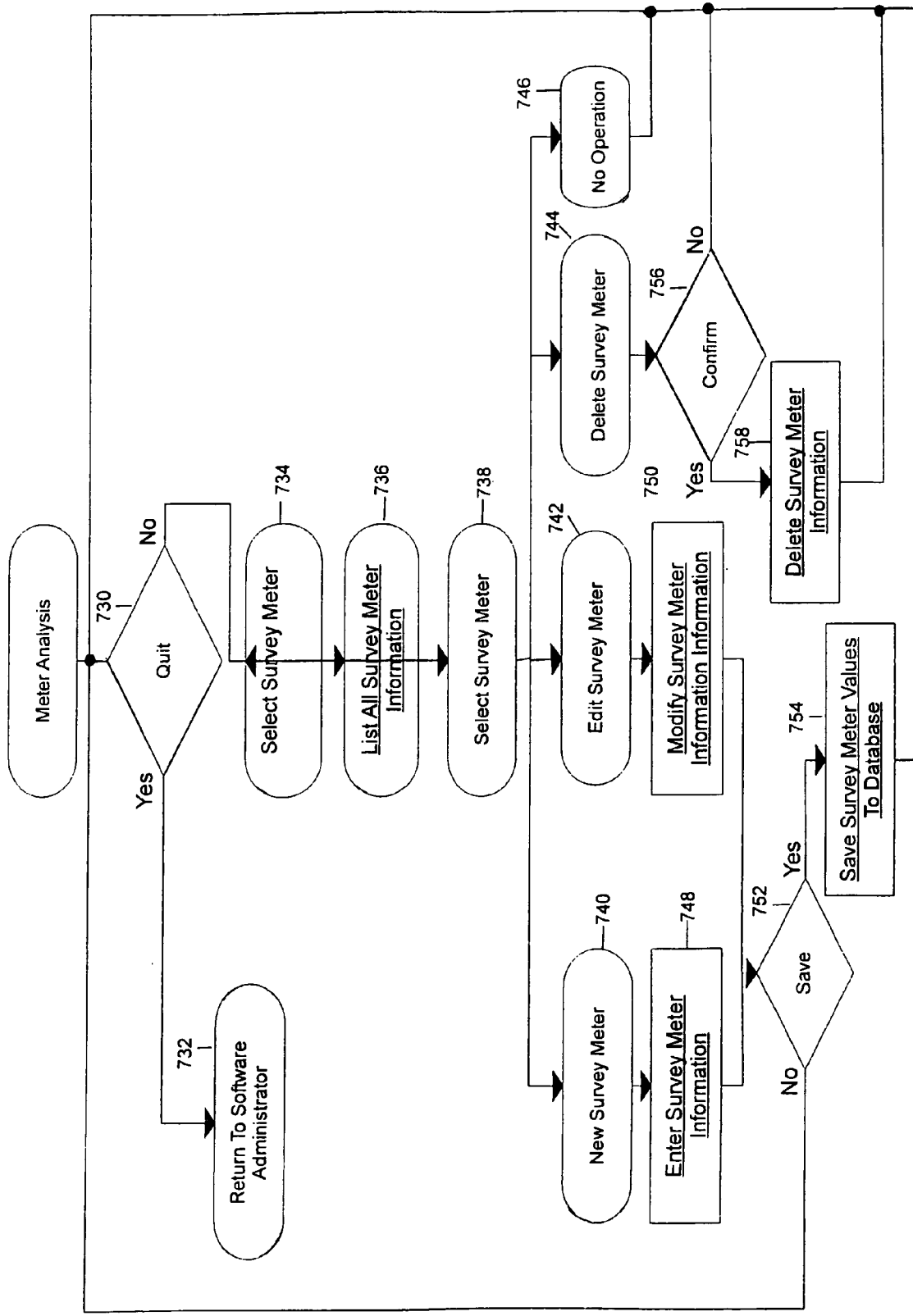
Figure 35:
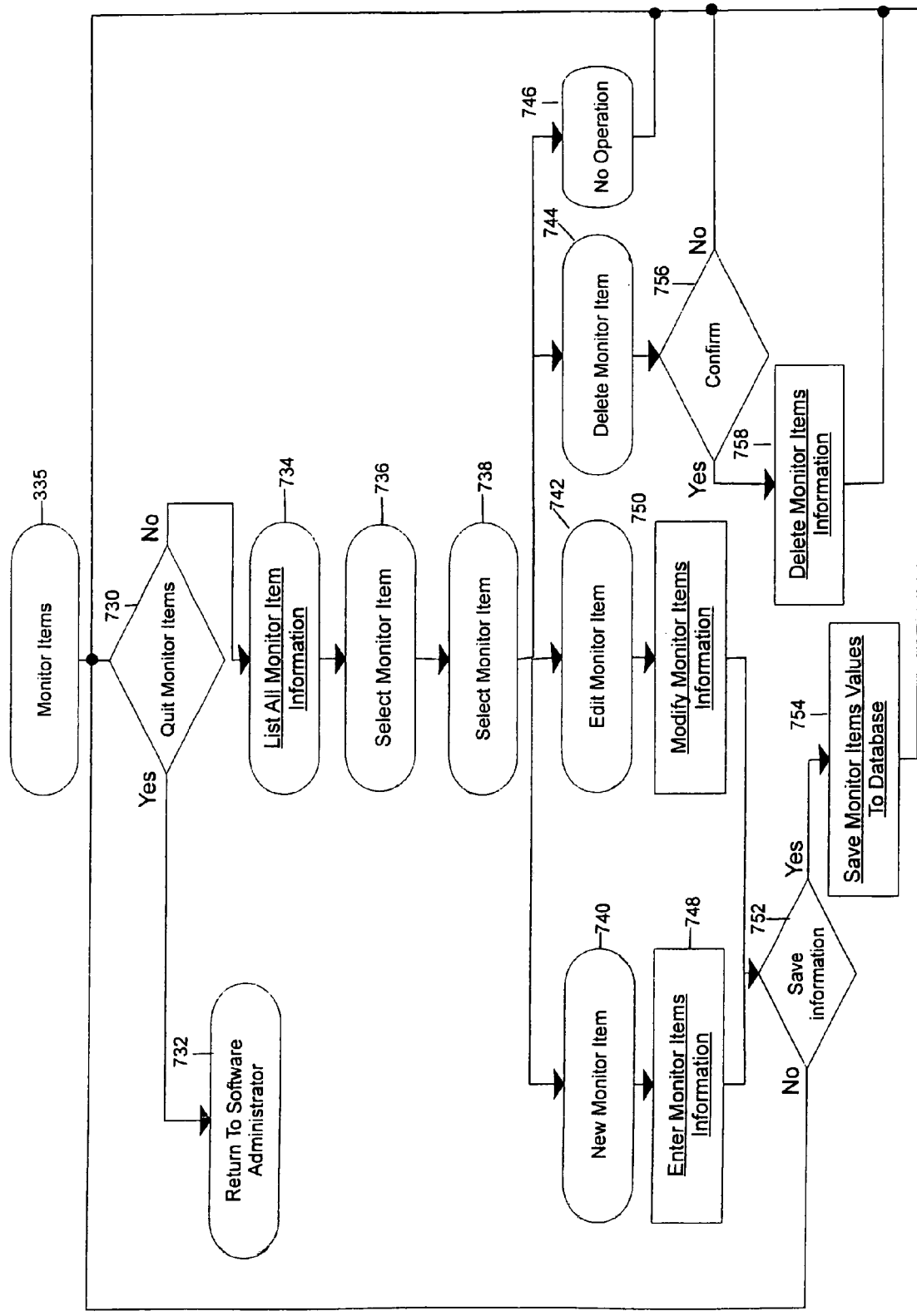
Figure 36A:
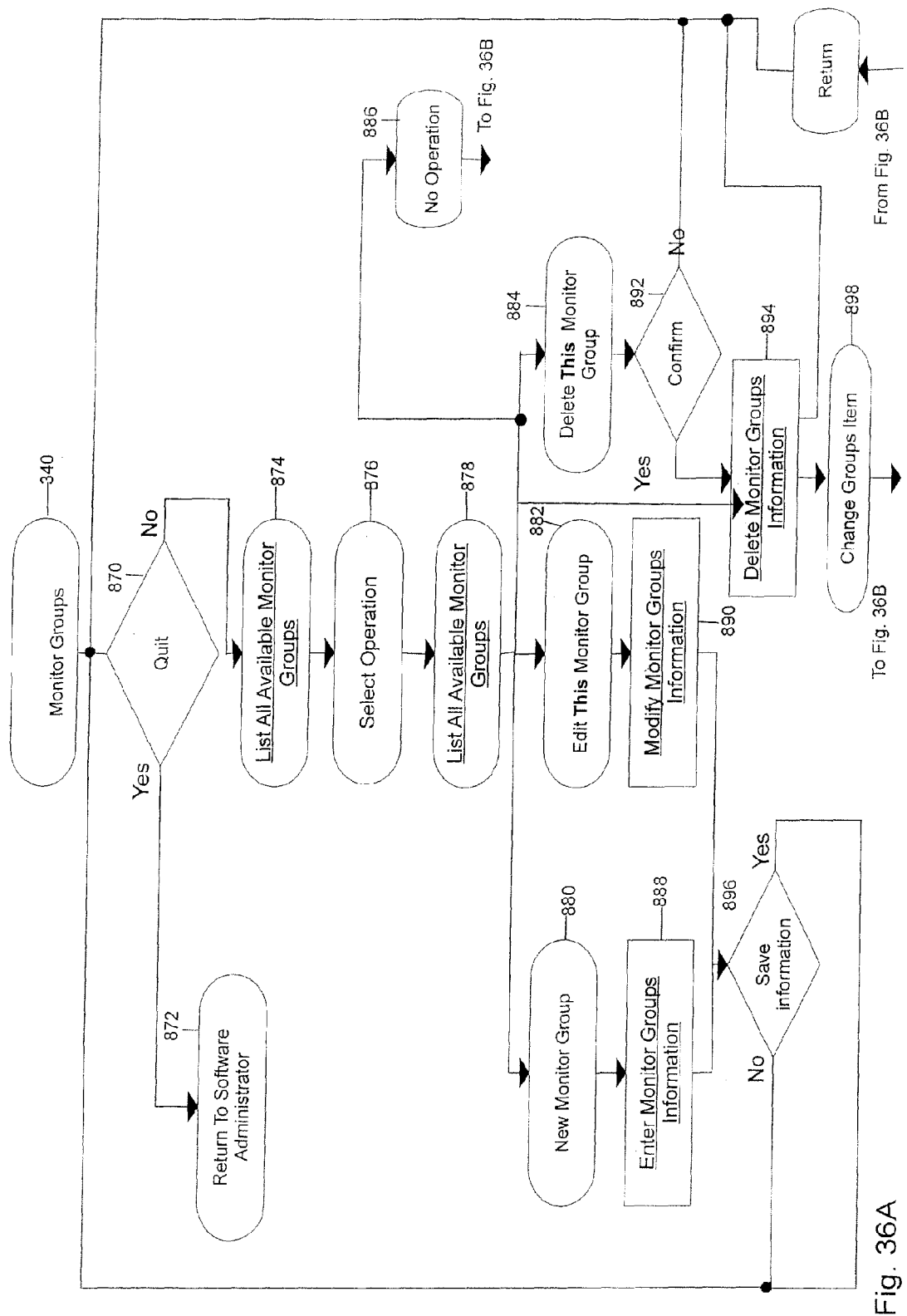
Figure 36B:
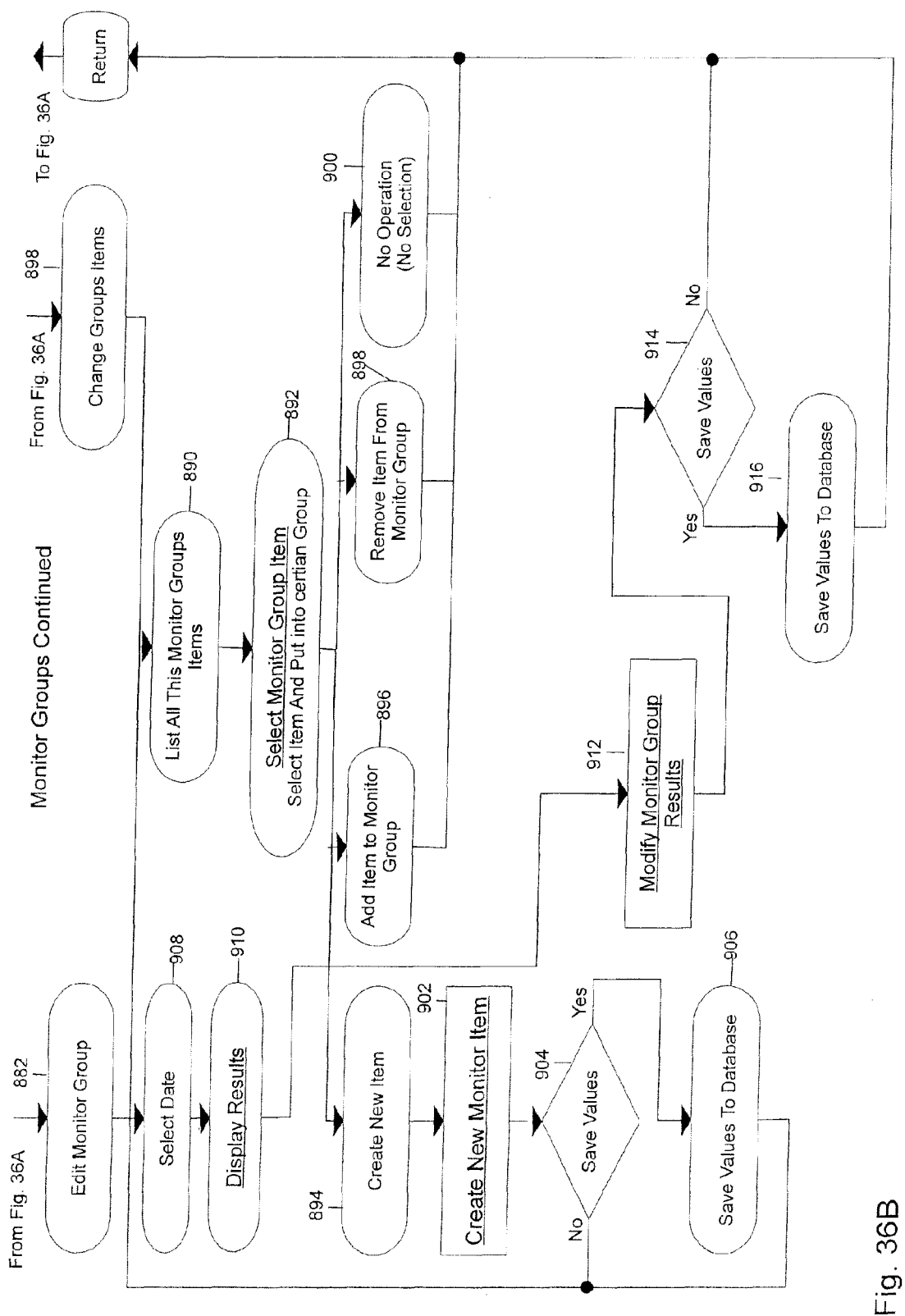
Figure 37:
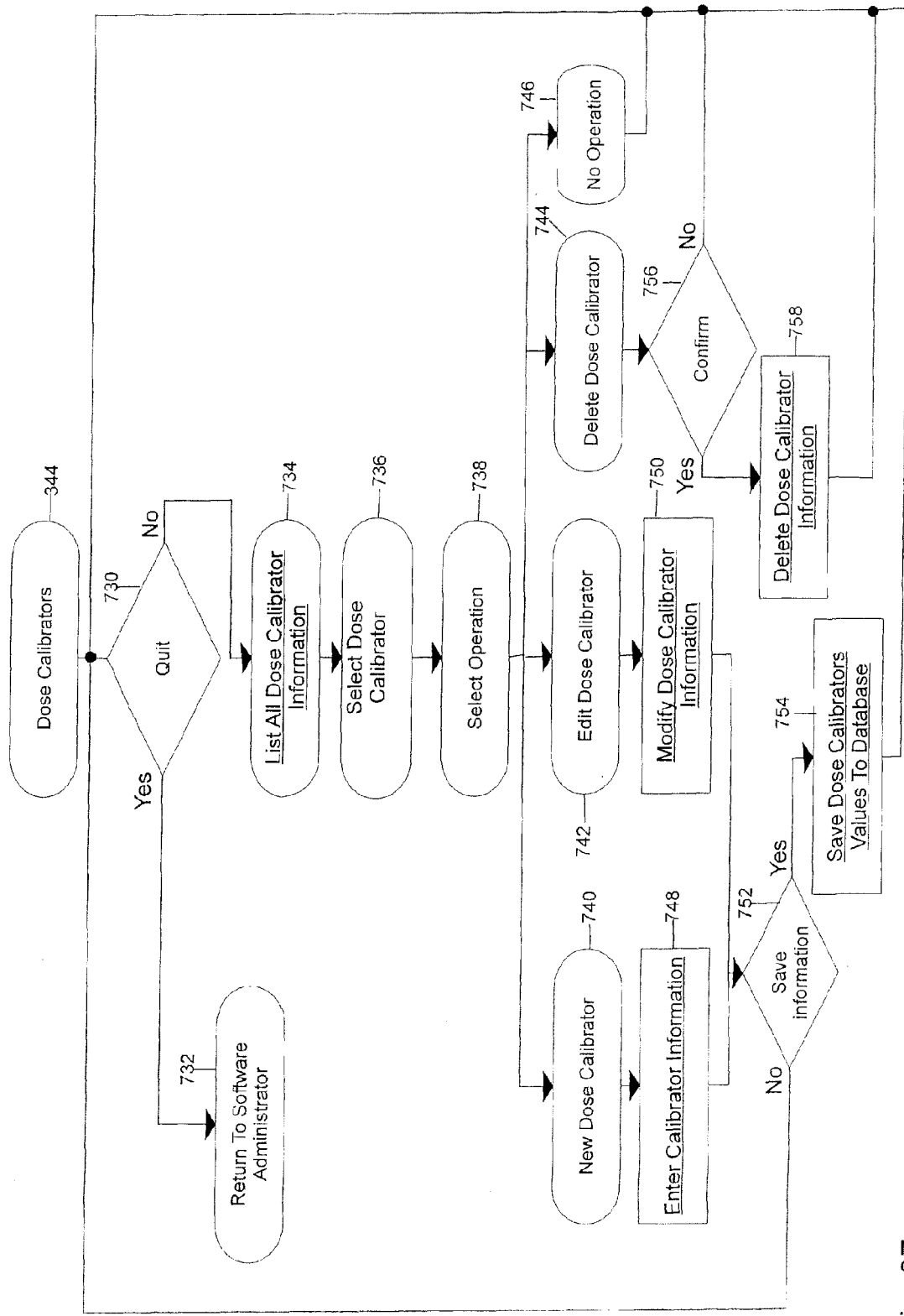
Figure 38:
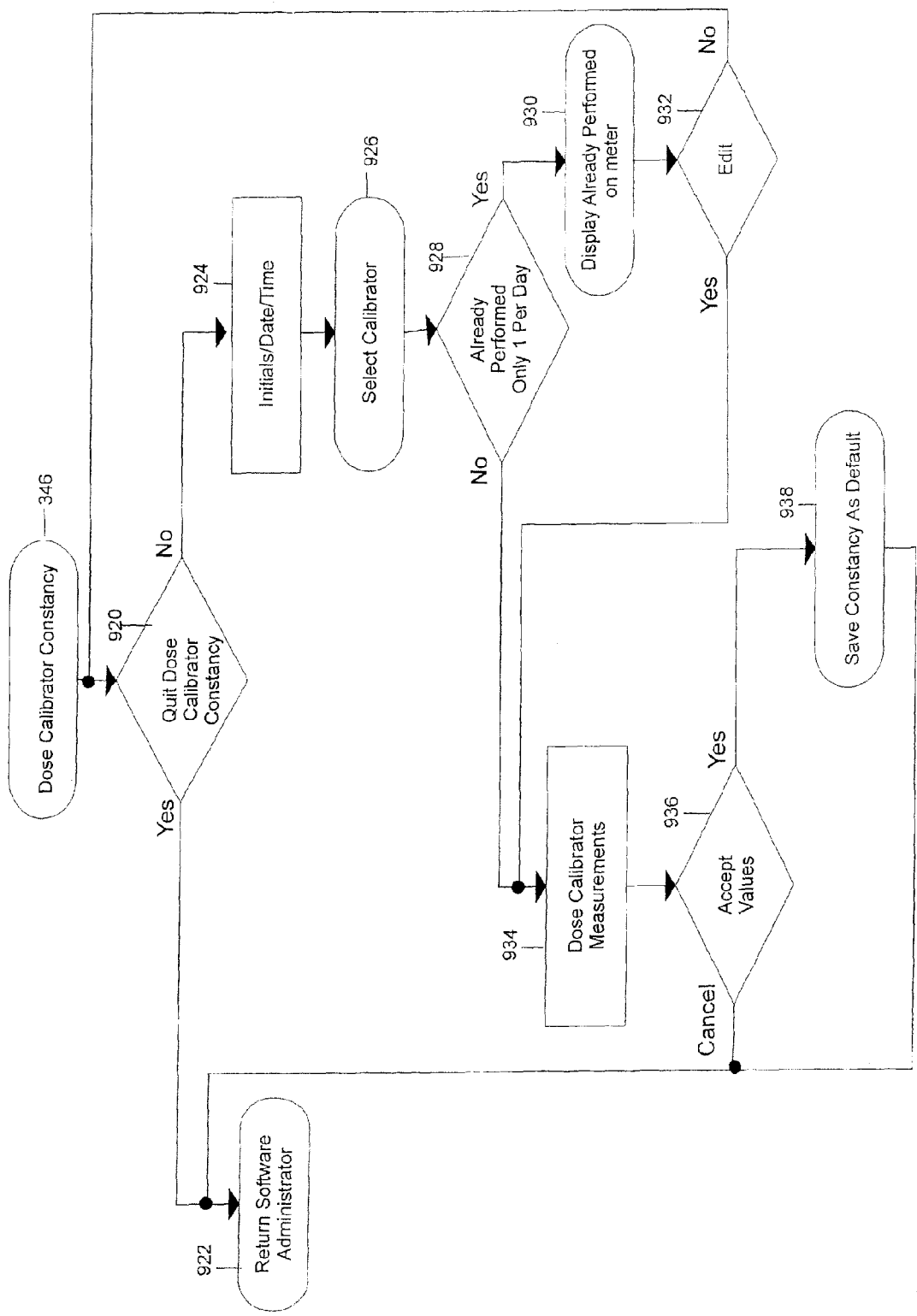
Figure 39:
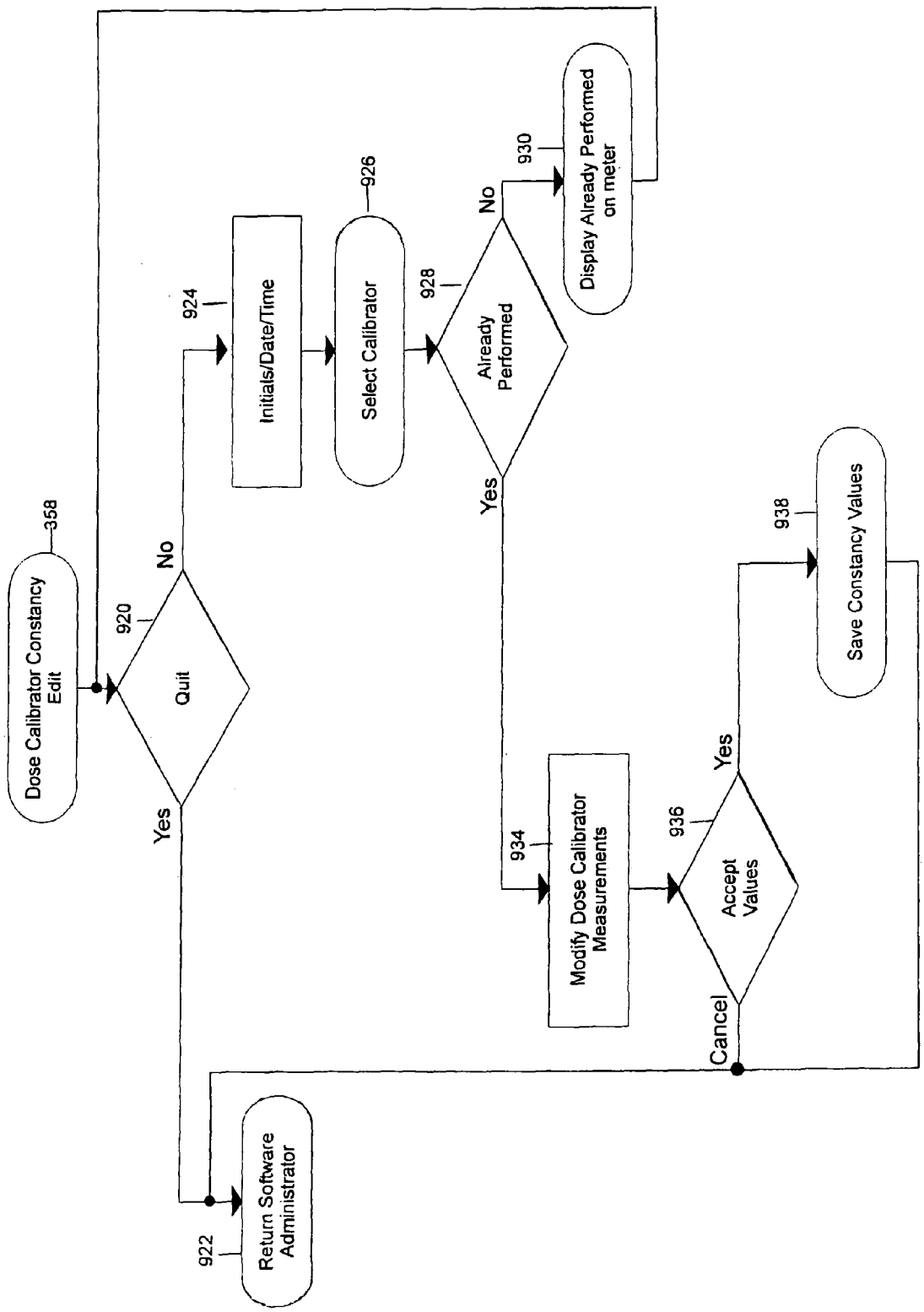
Figure 40:
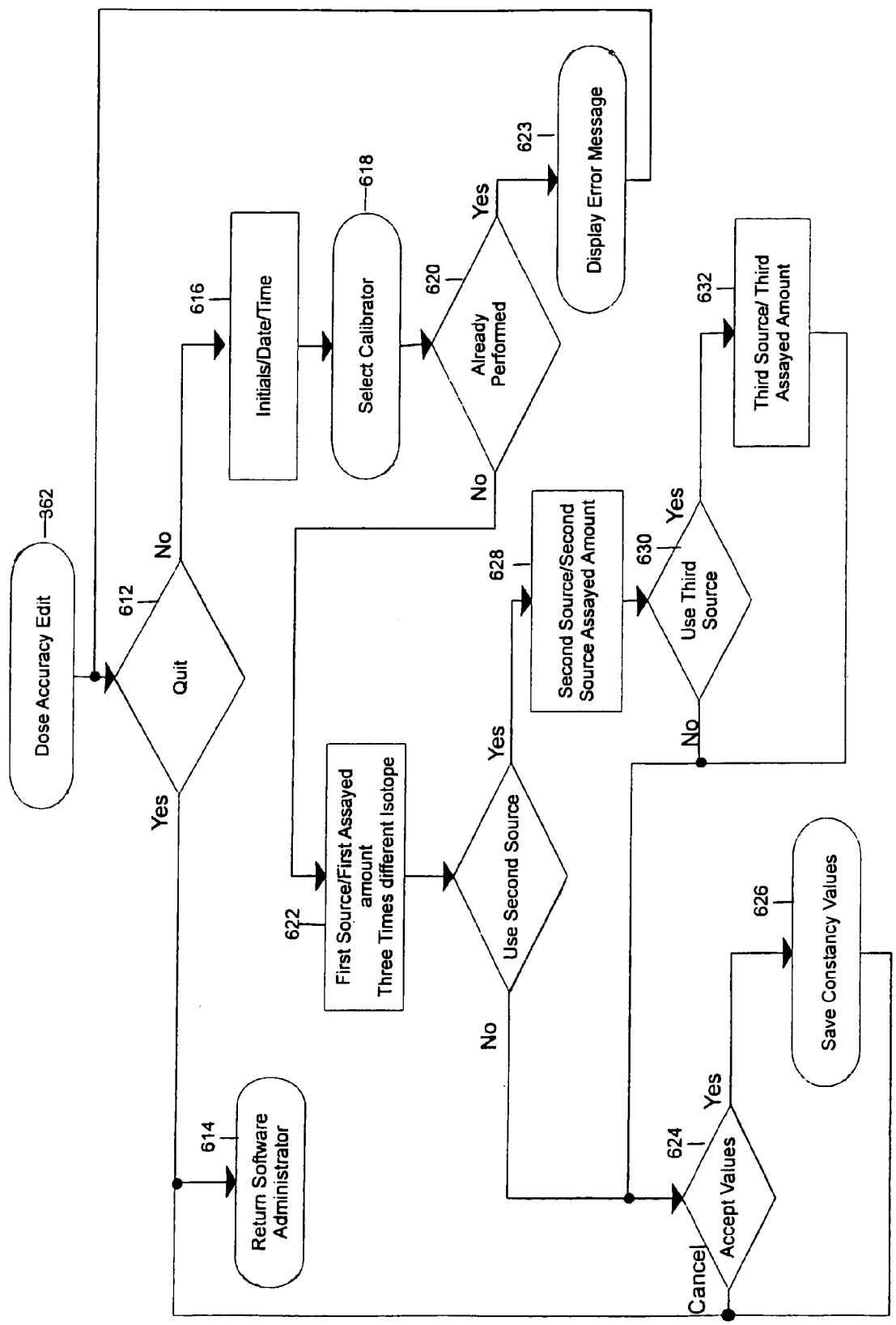
Figure 41:
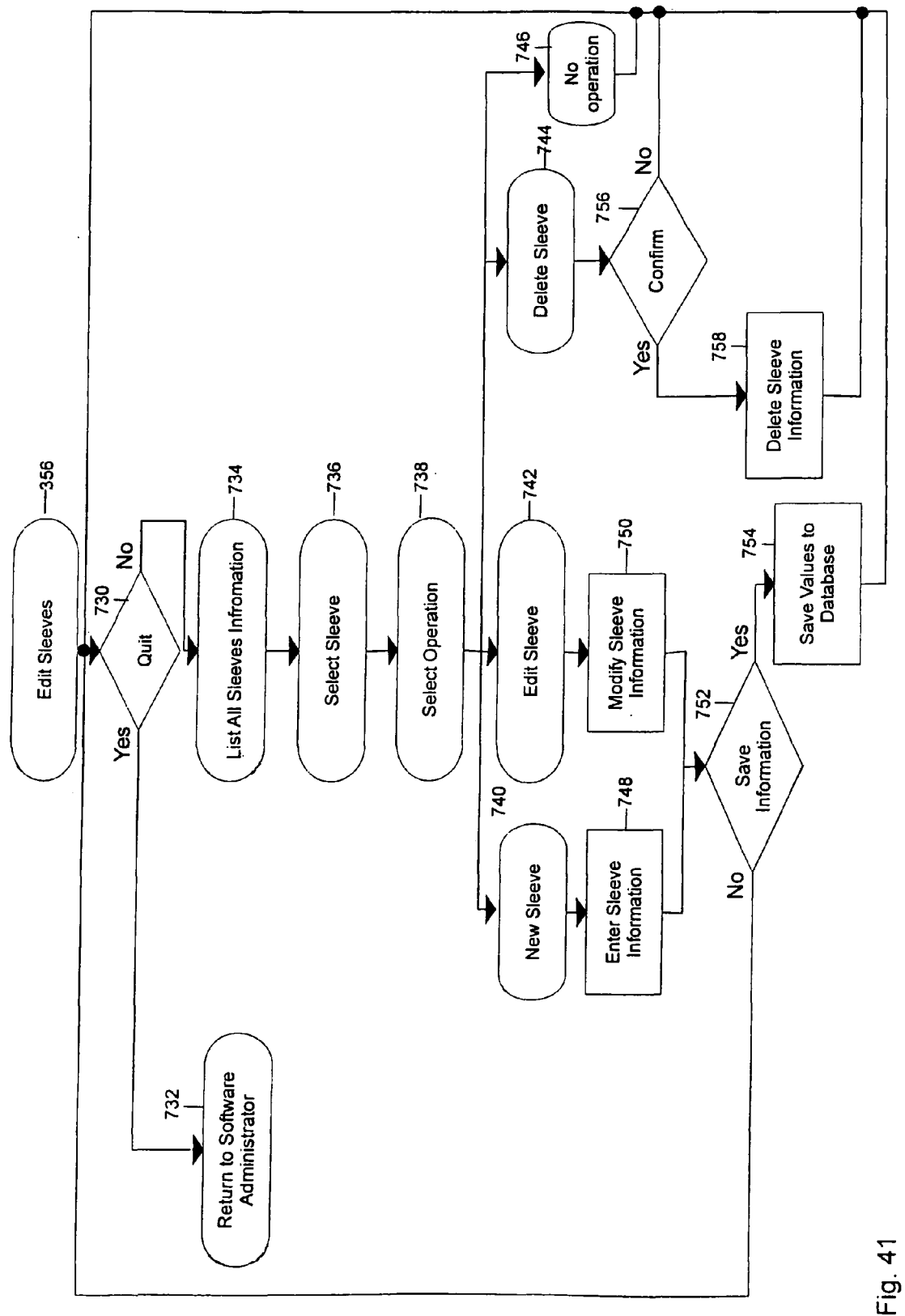
Figure 42:
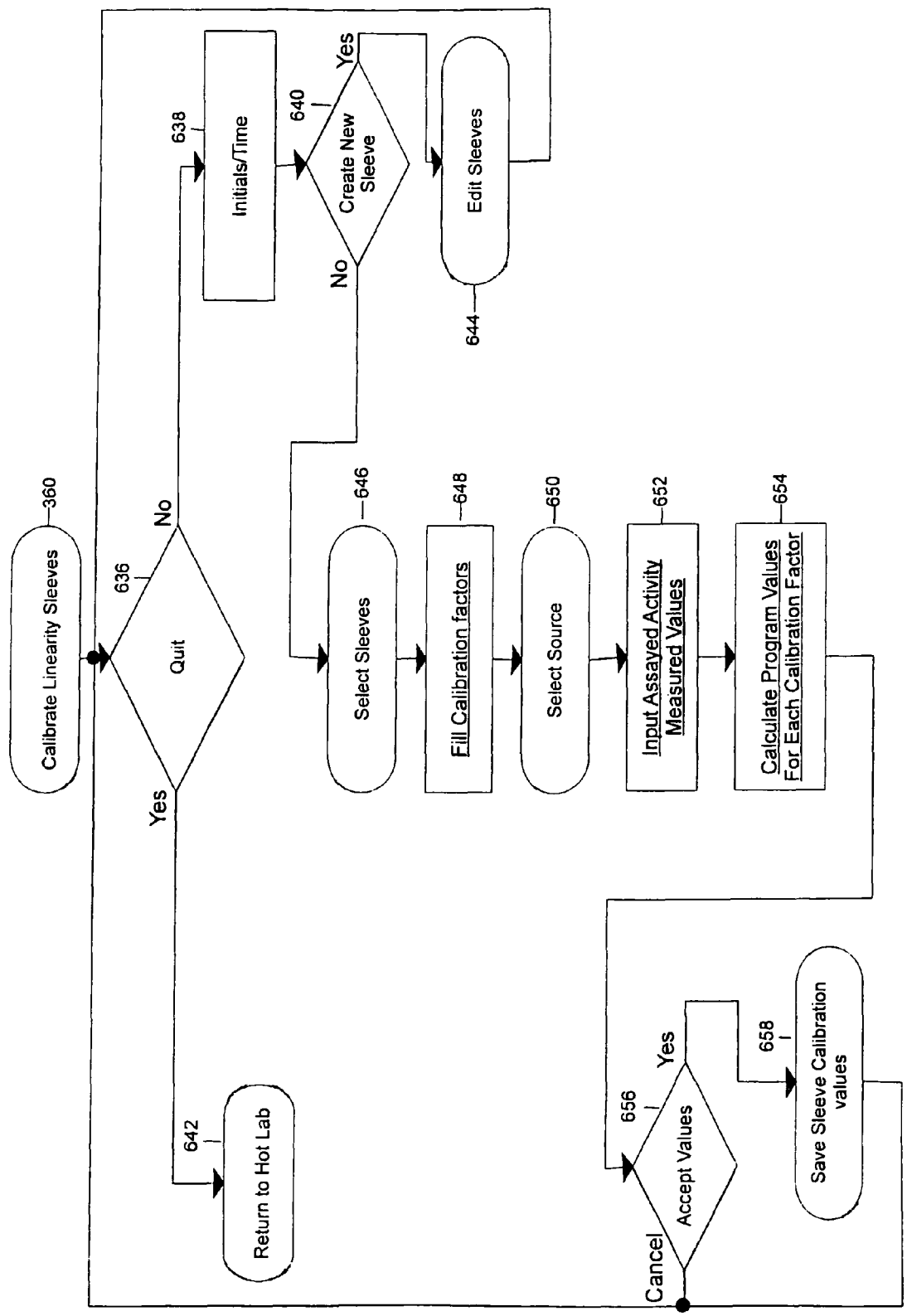
Figure 43:
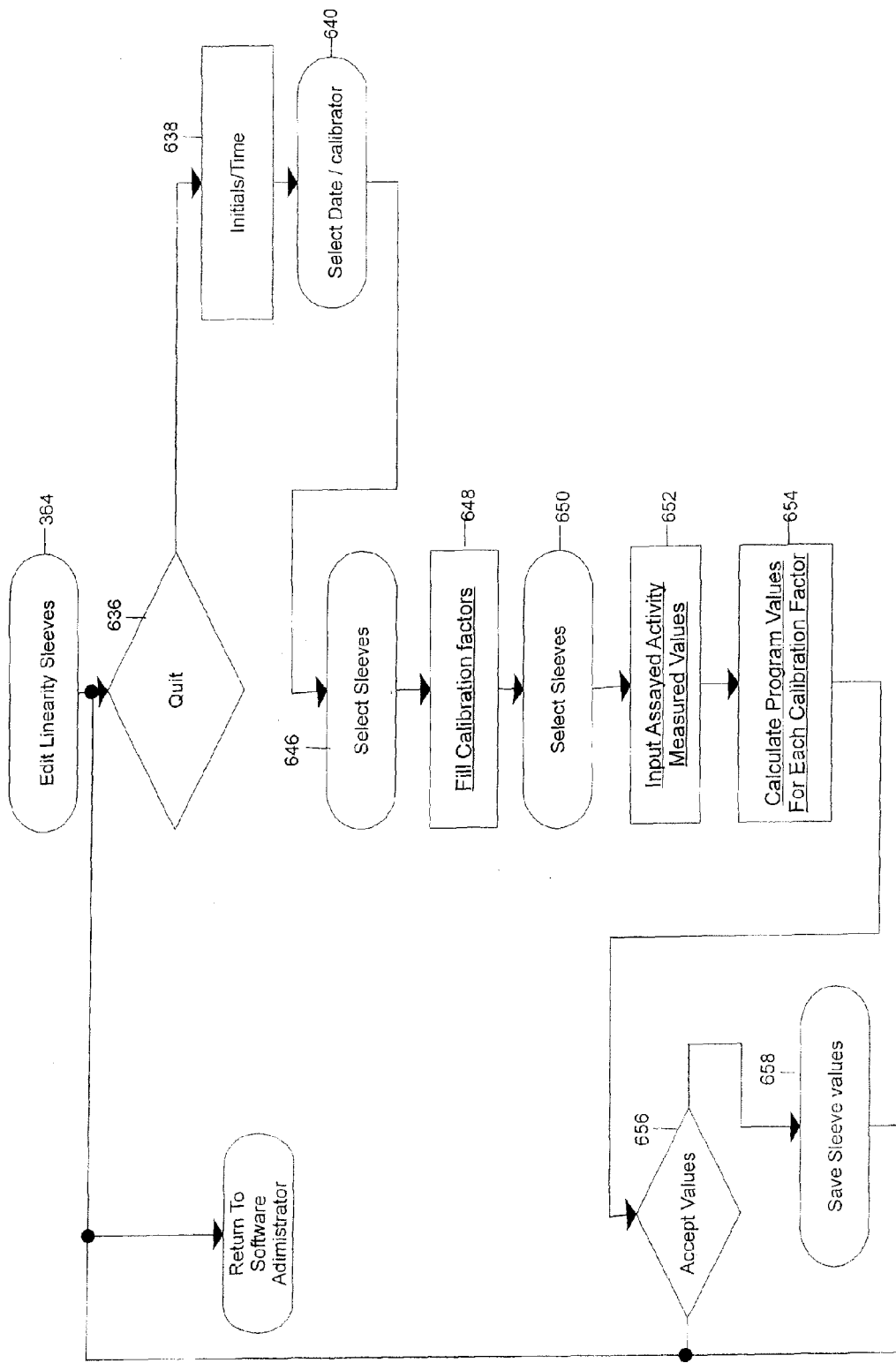
Figure 44:
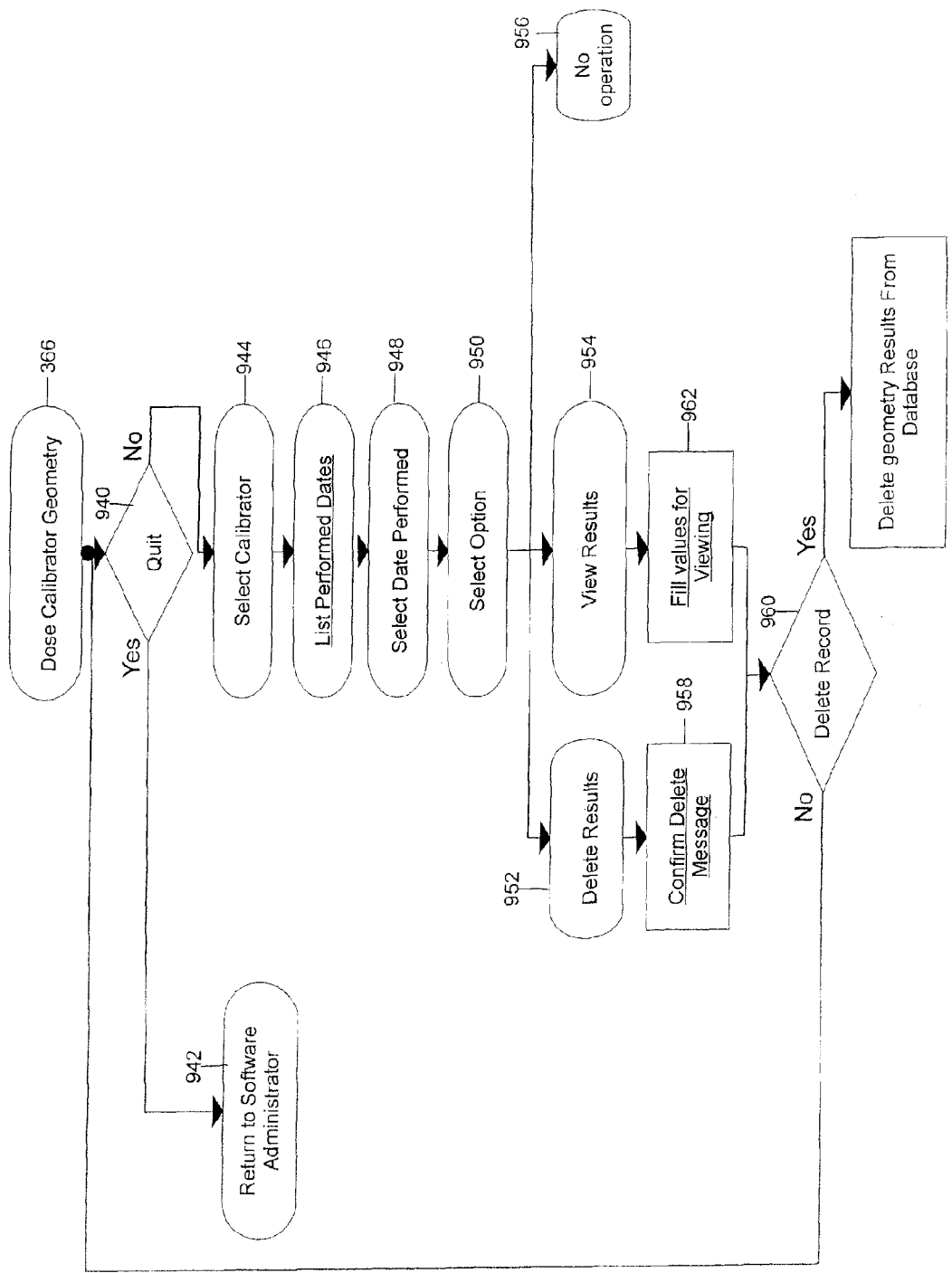
Figure 45:
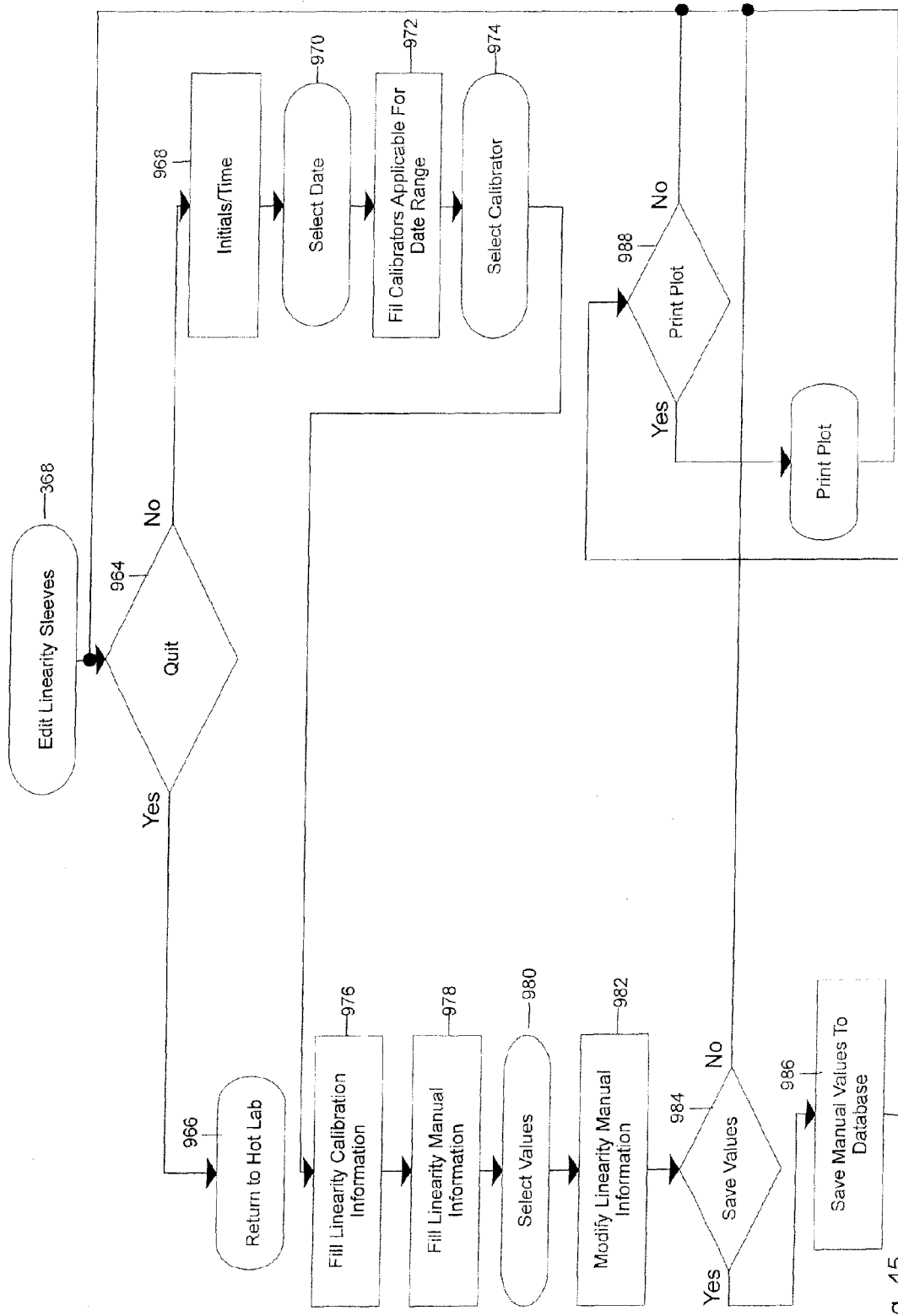
Figure 46A:
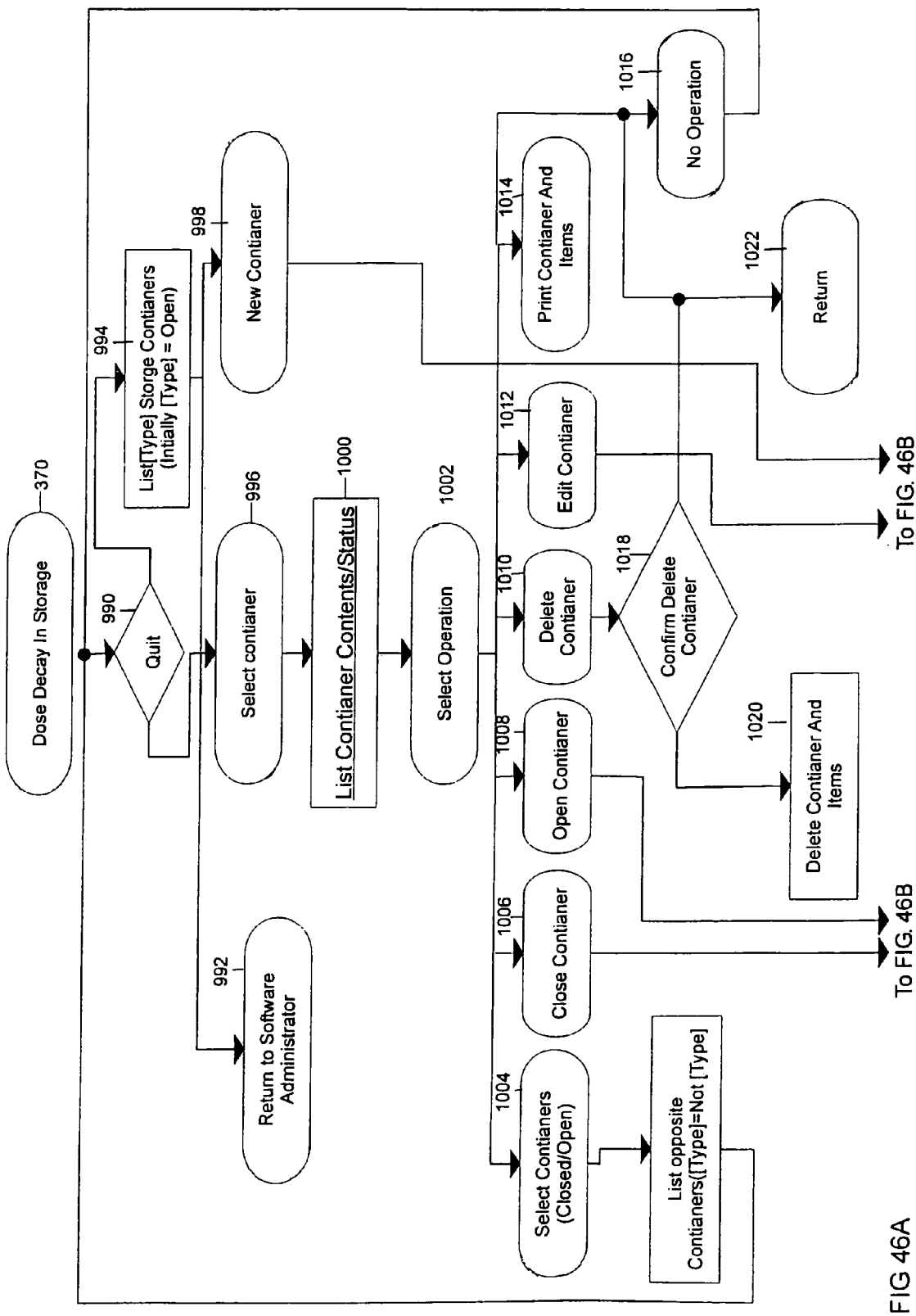
Figure 46B:
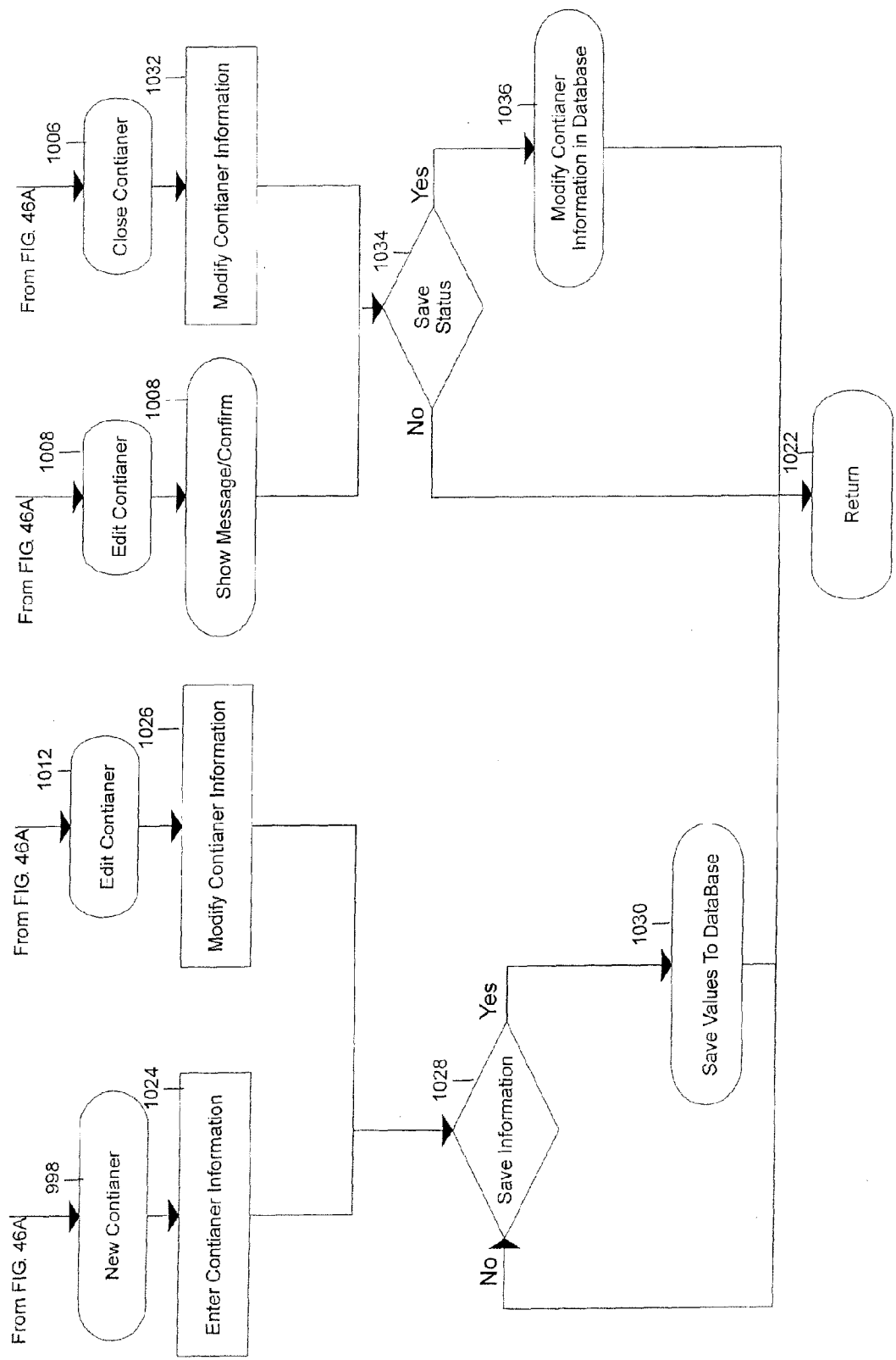
Figure 47:
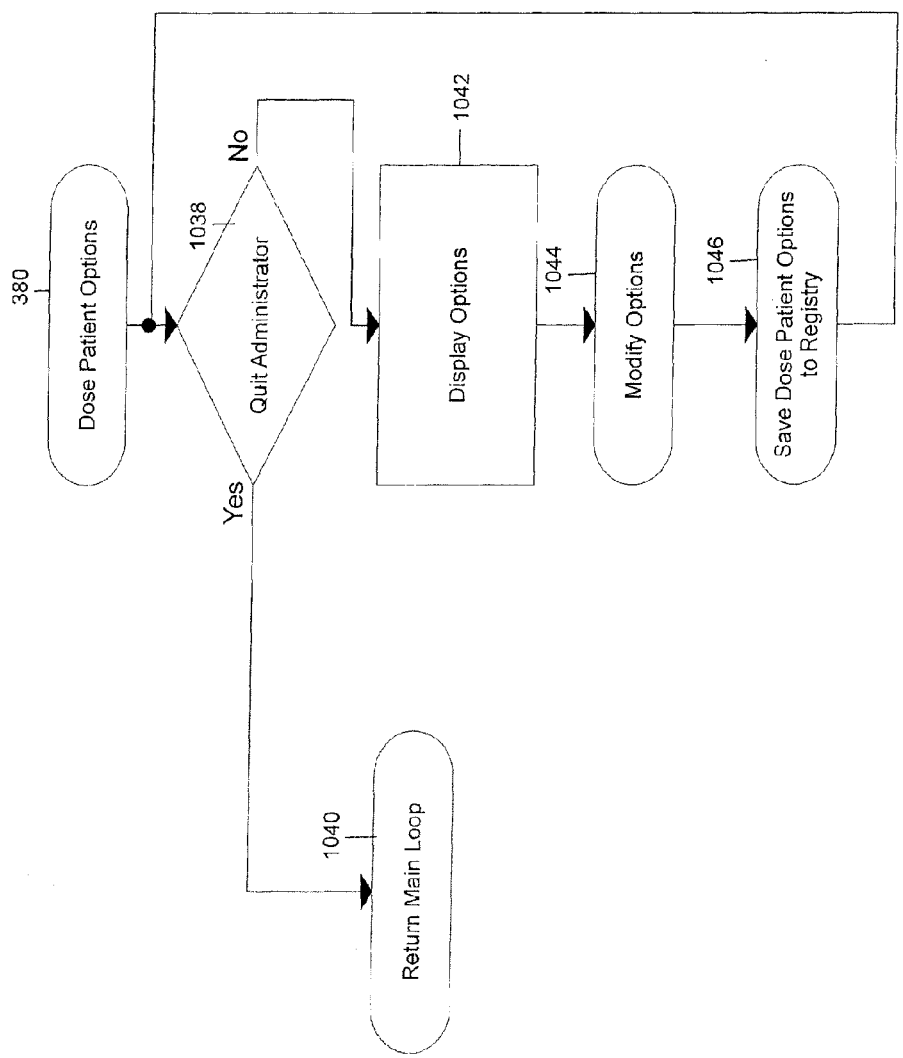
Figure 48:
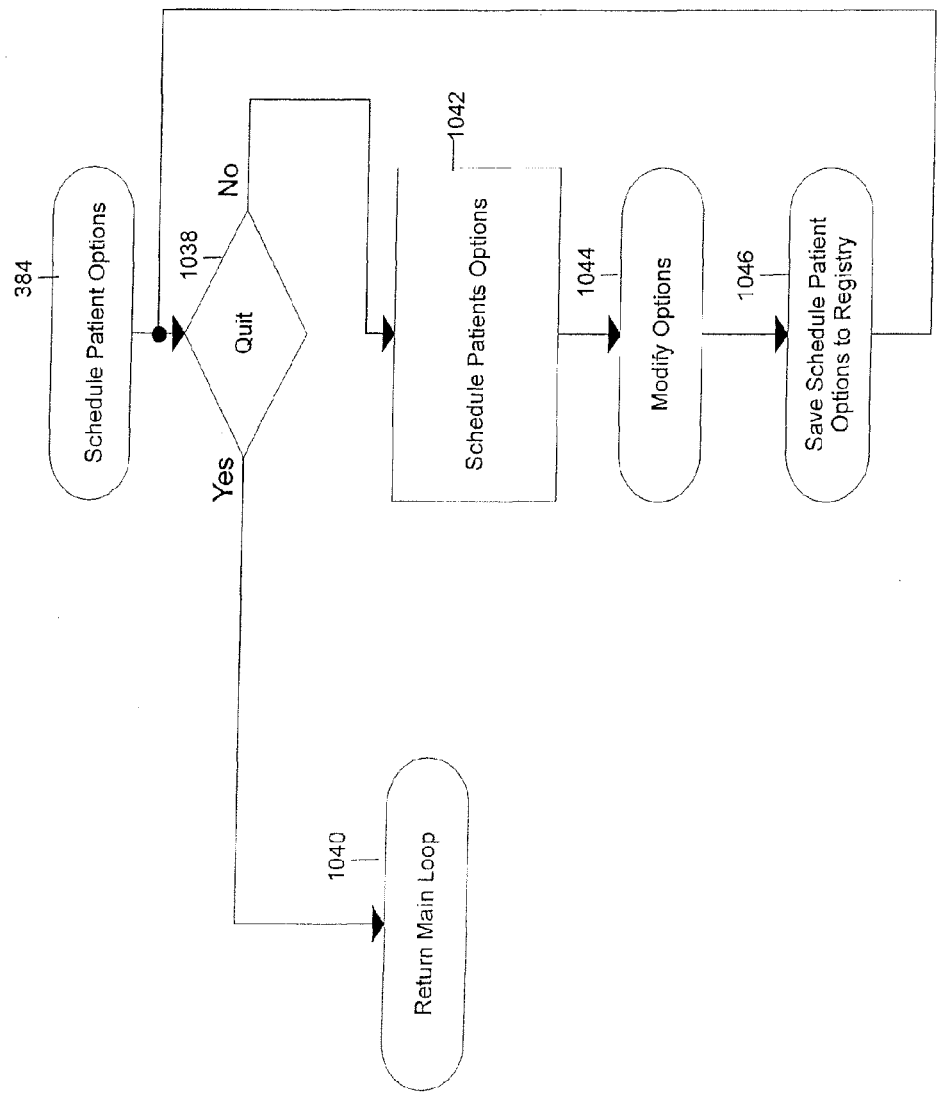
Figure 49:
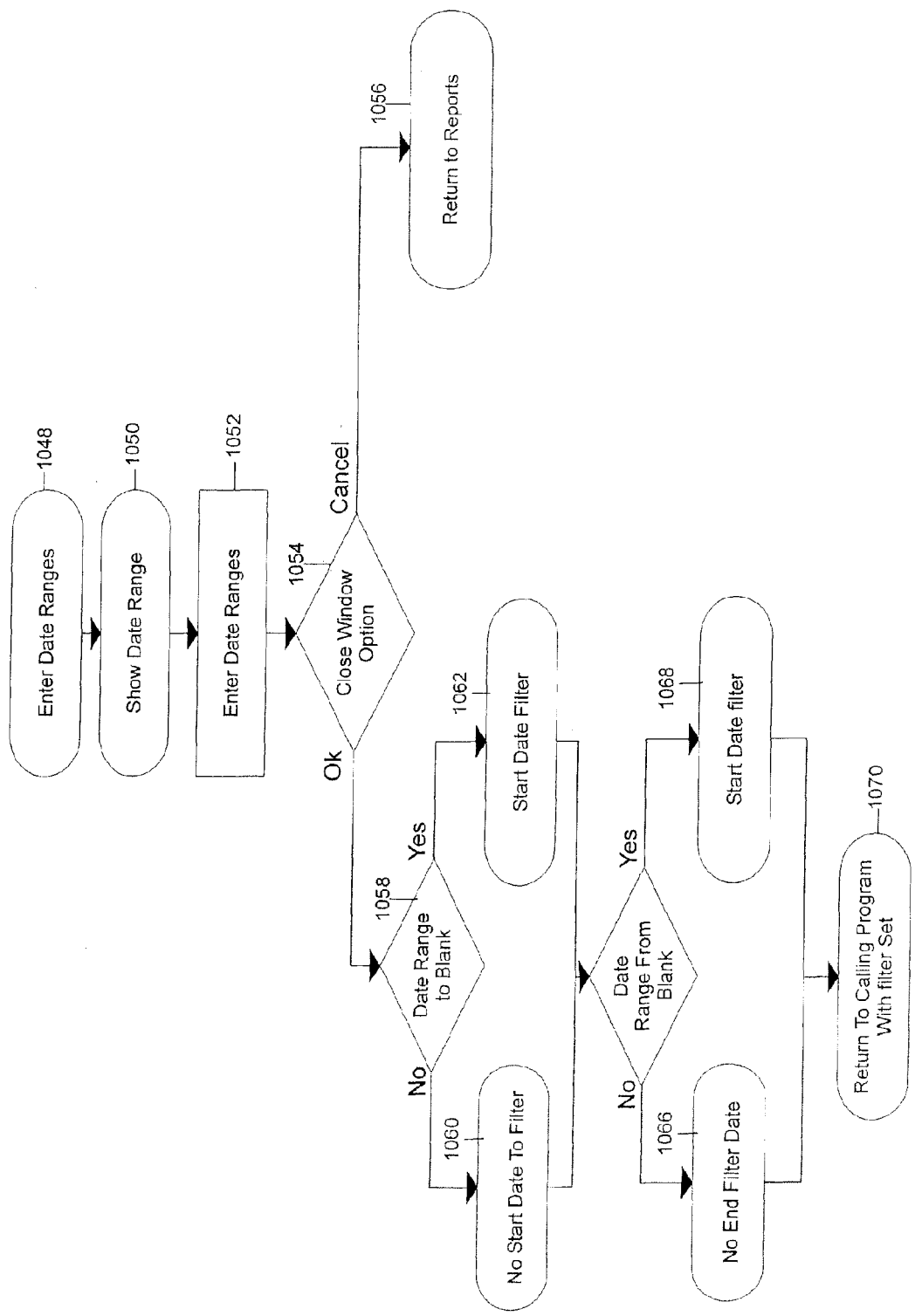
Figure 50:
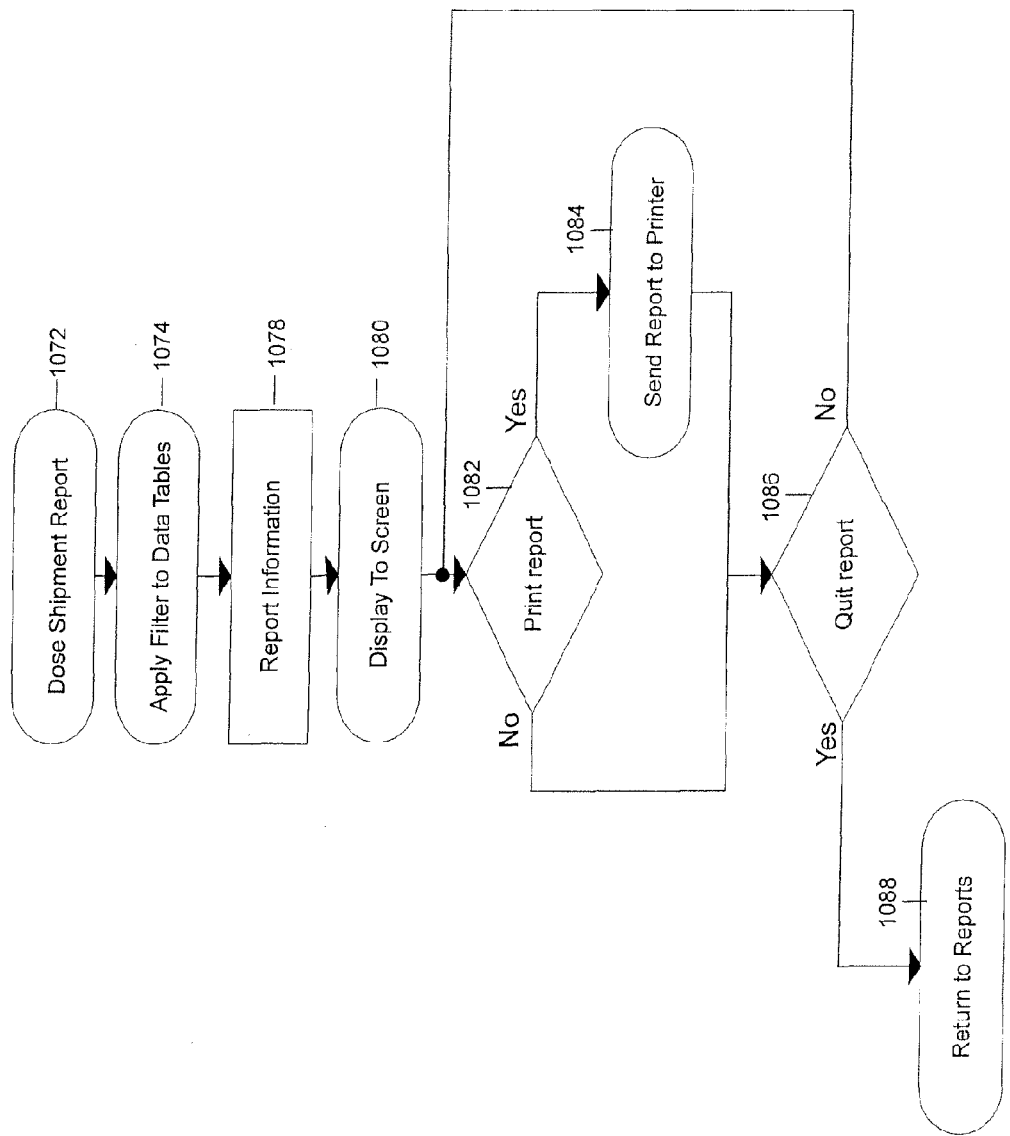
Figure 51:
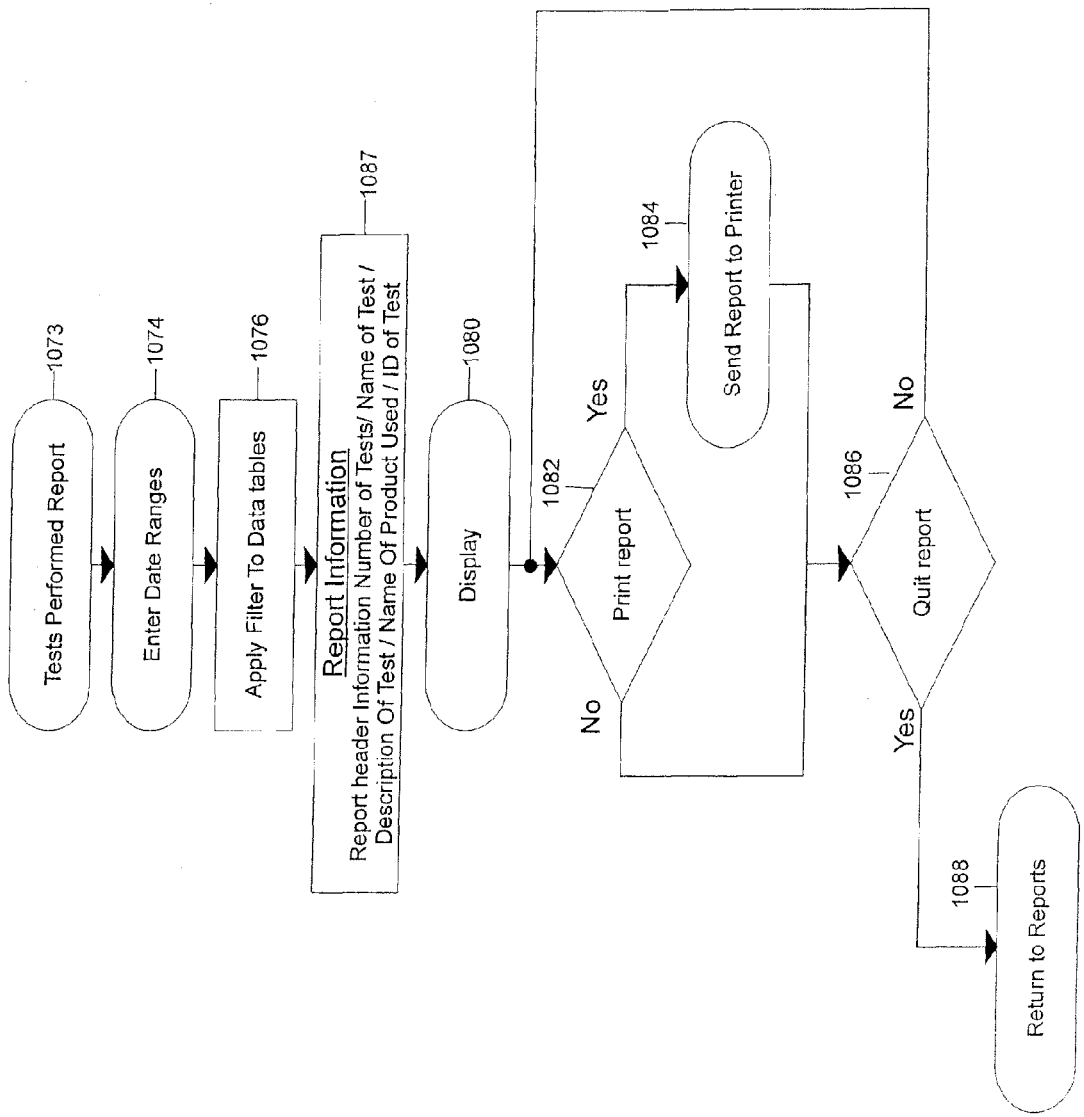
Figure 52:
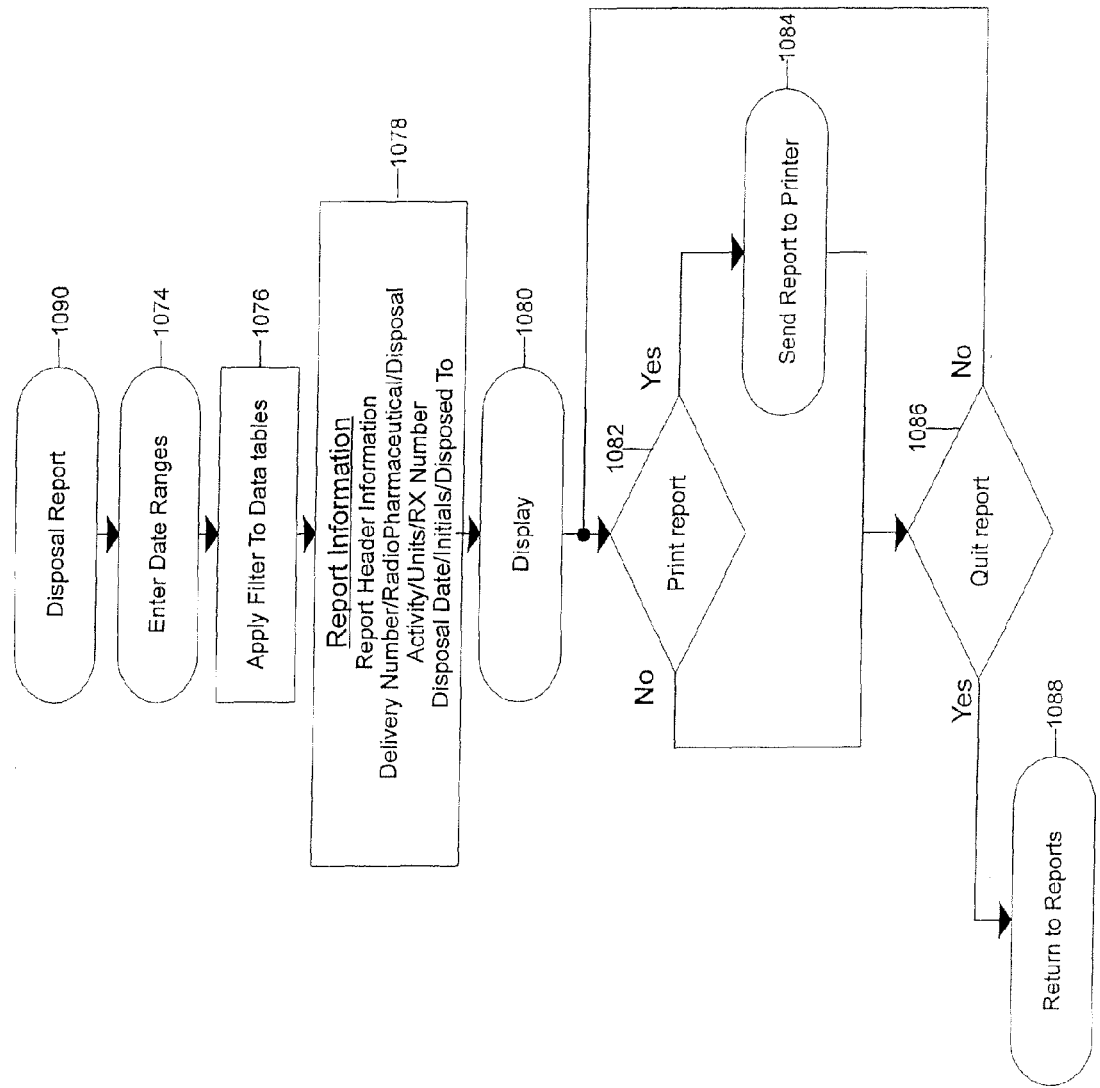
Figure 53:
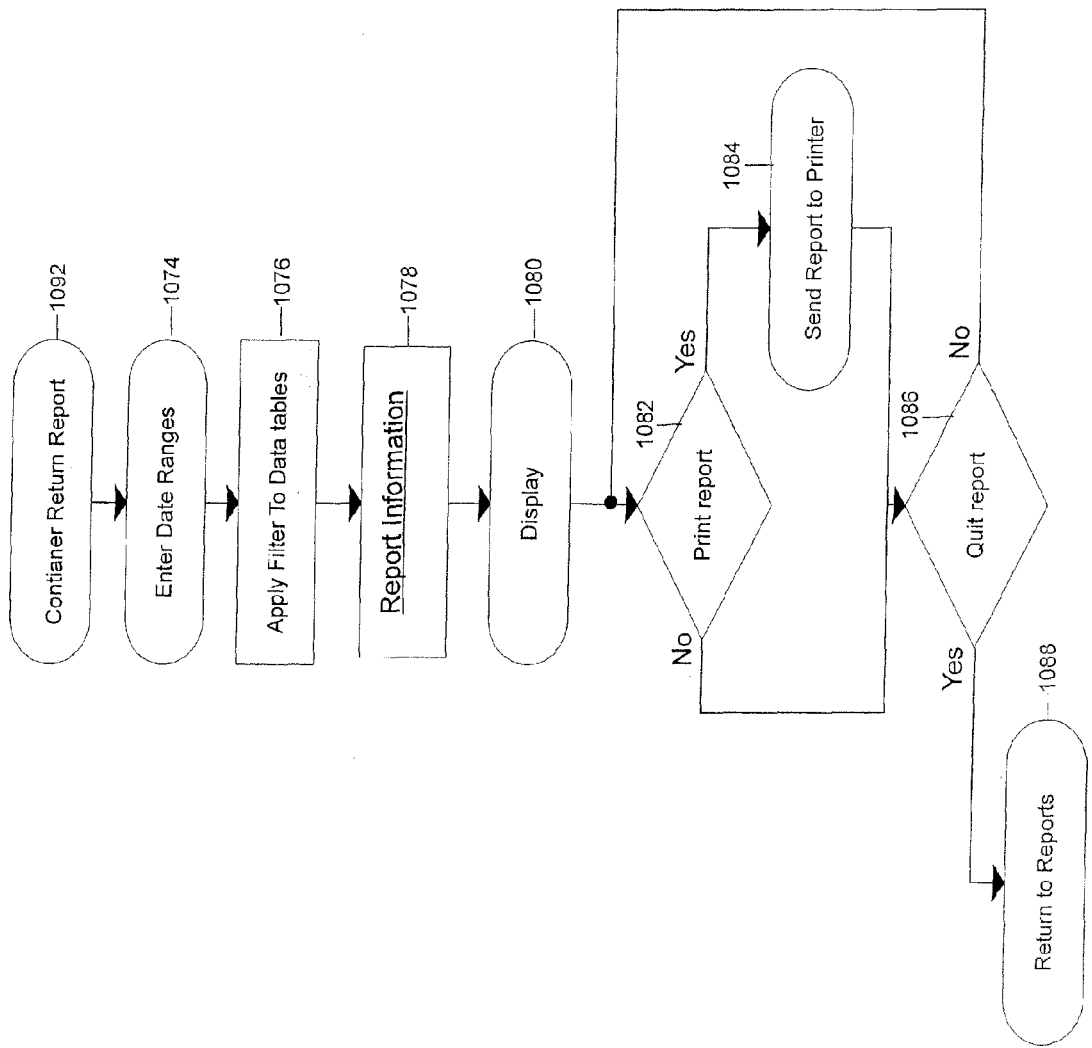
Figure 54:
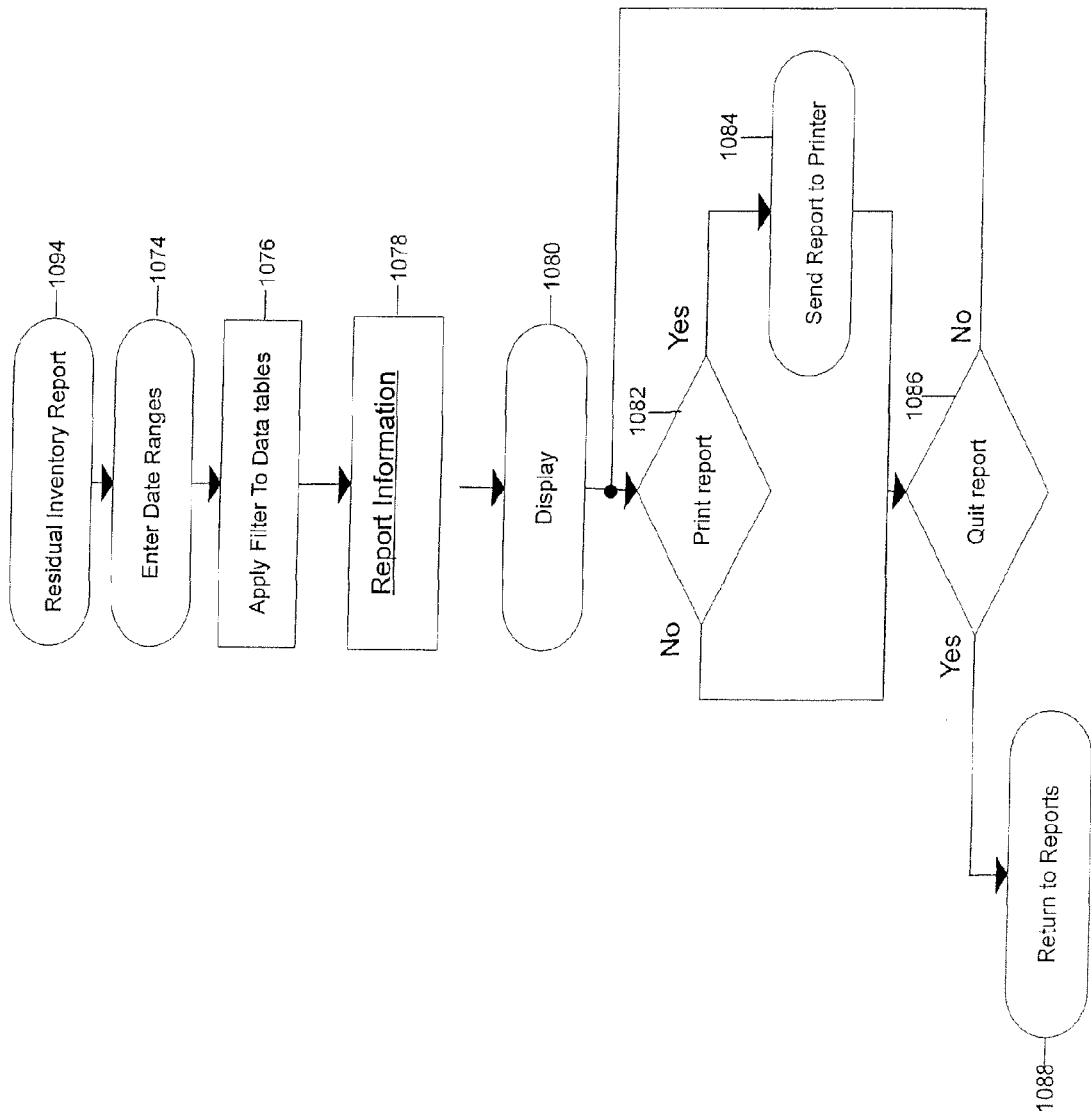
Figure 55:
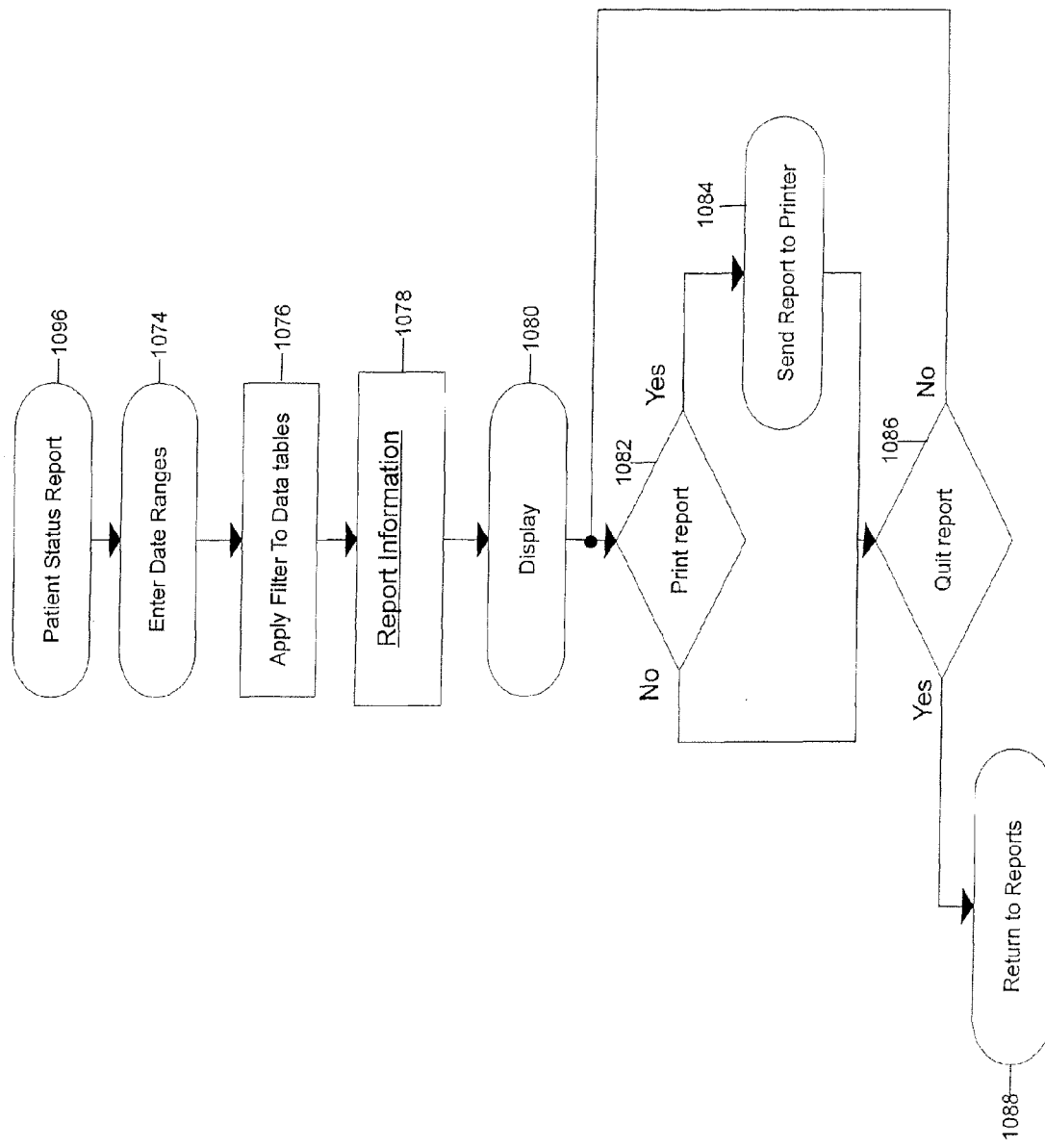
Figure 56:
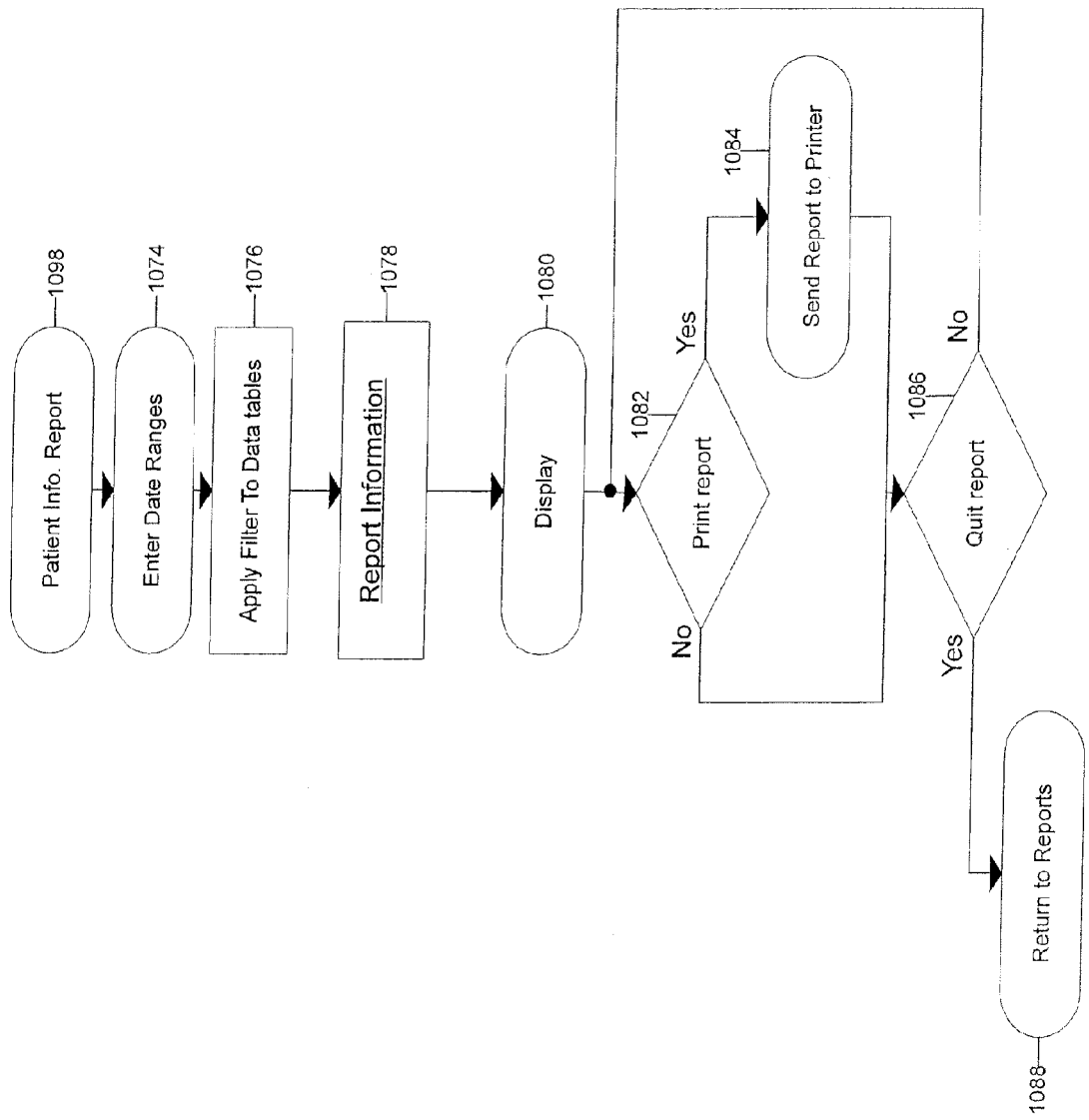
Figure 57:
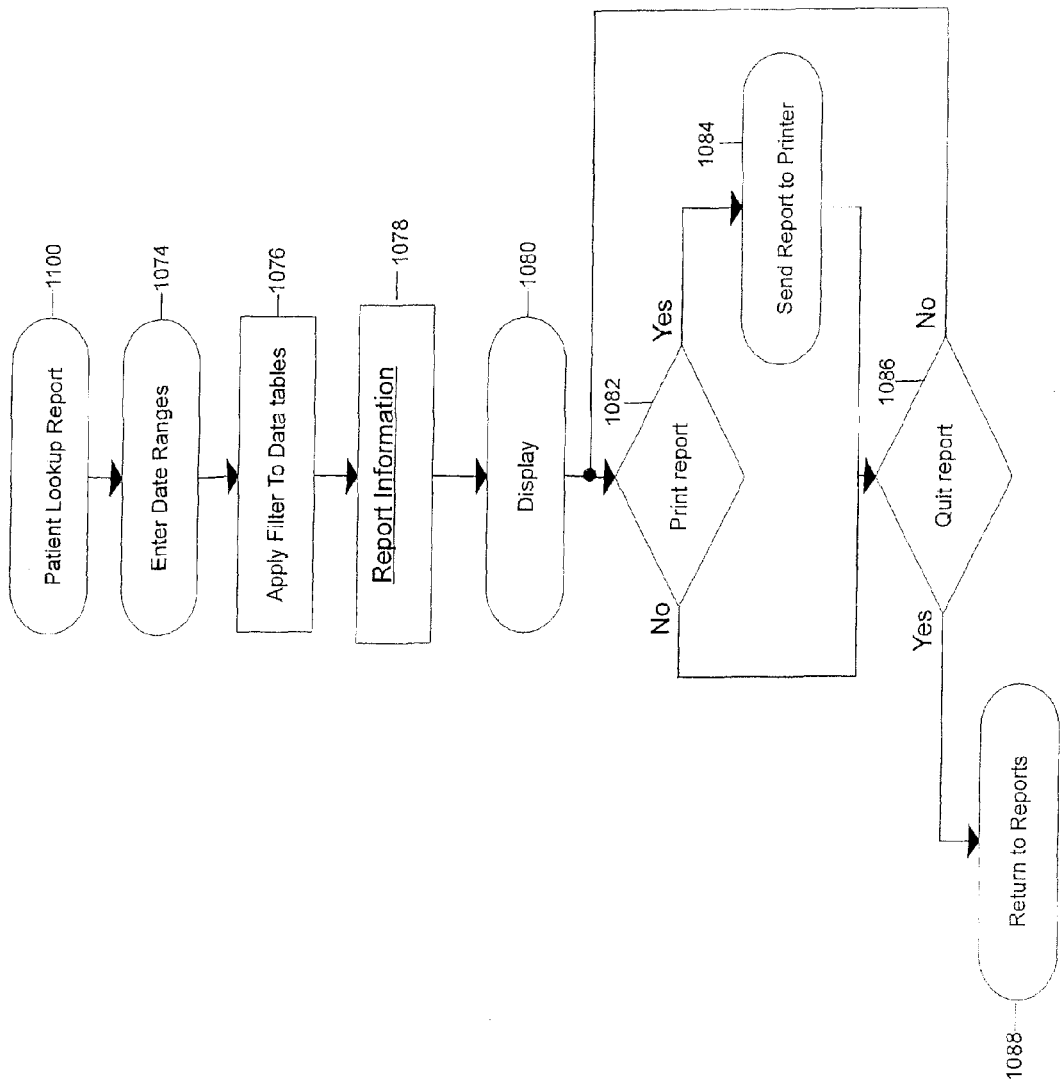
Figure 58:
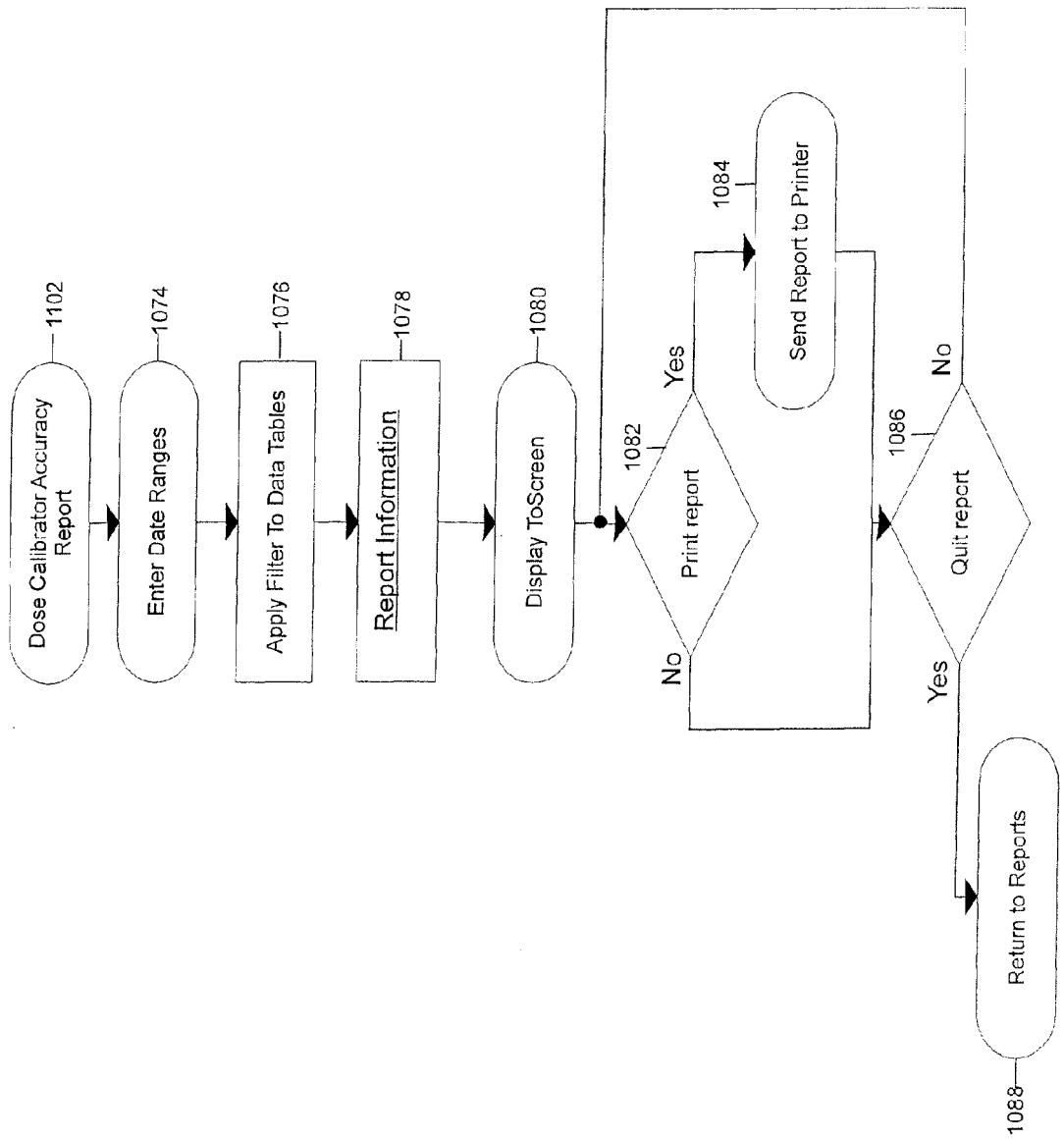
Figure 59:
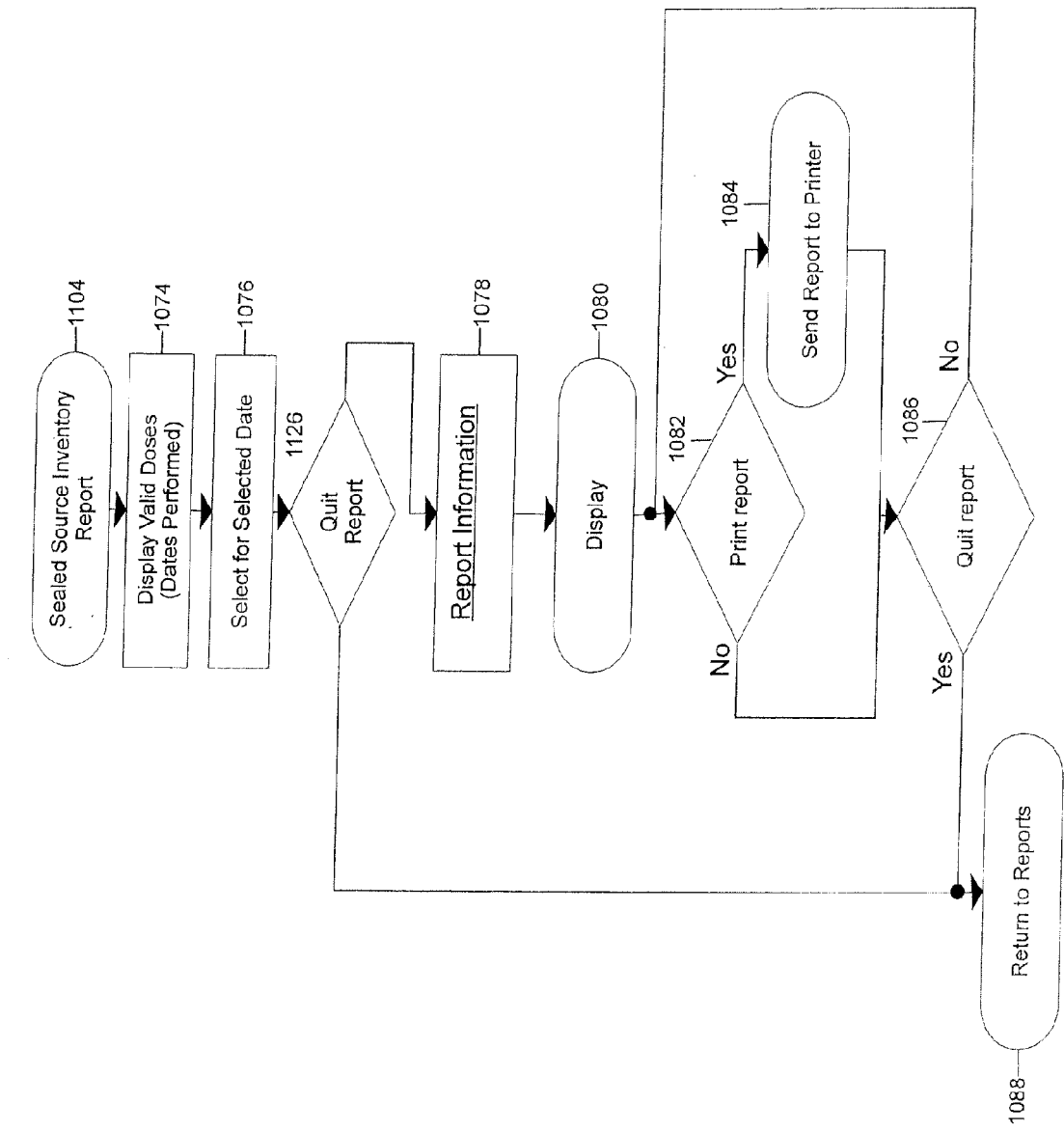
Figure 60:
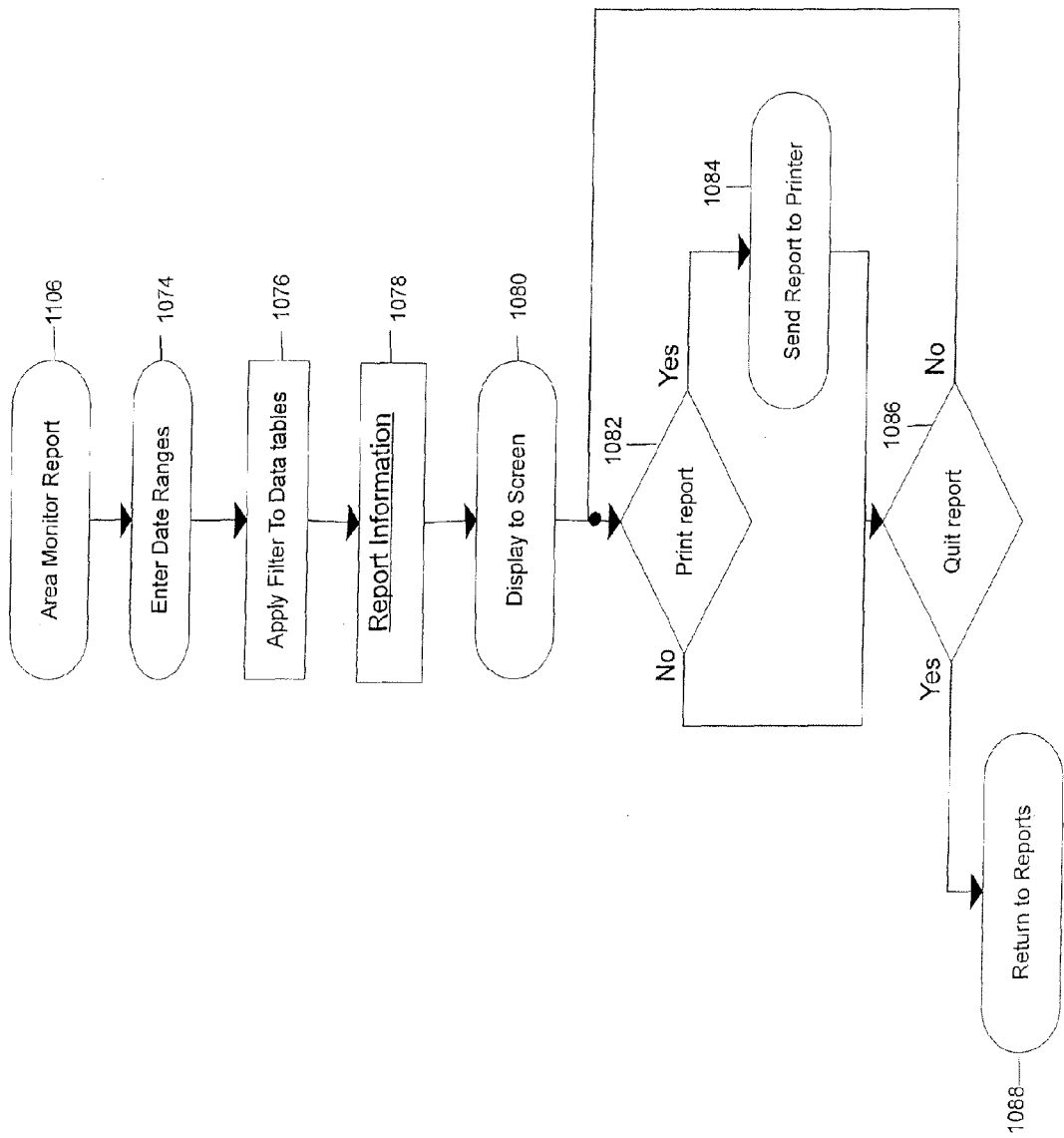
Figure 61:
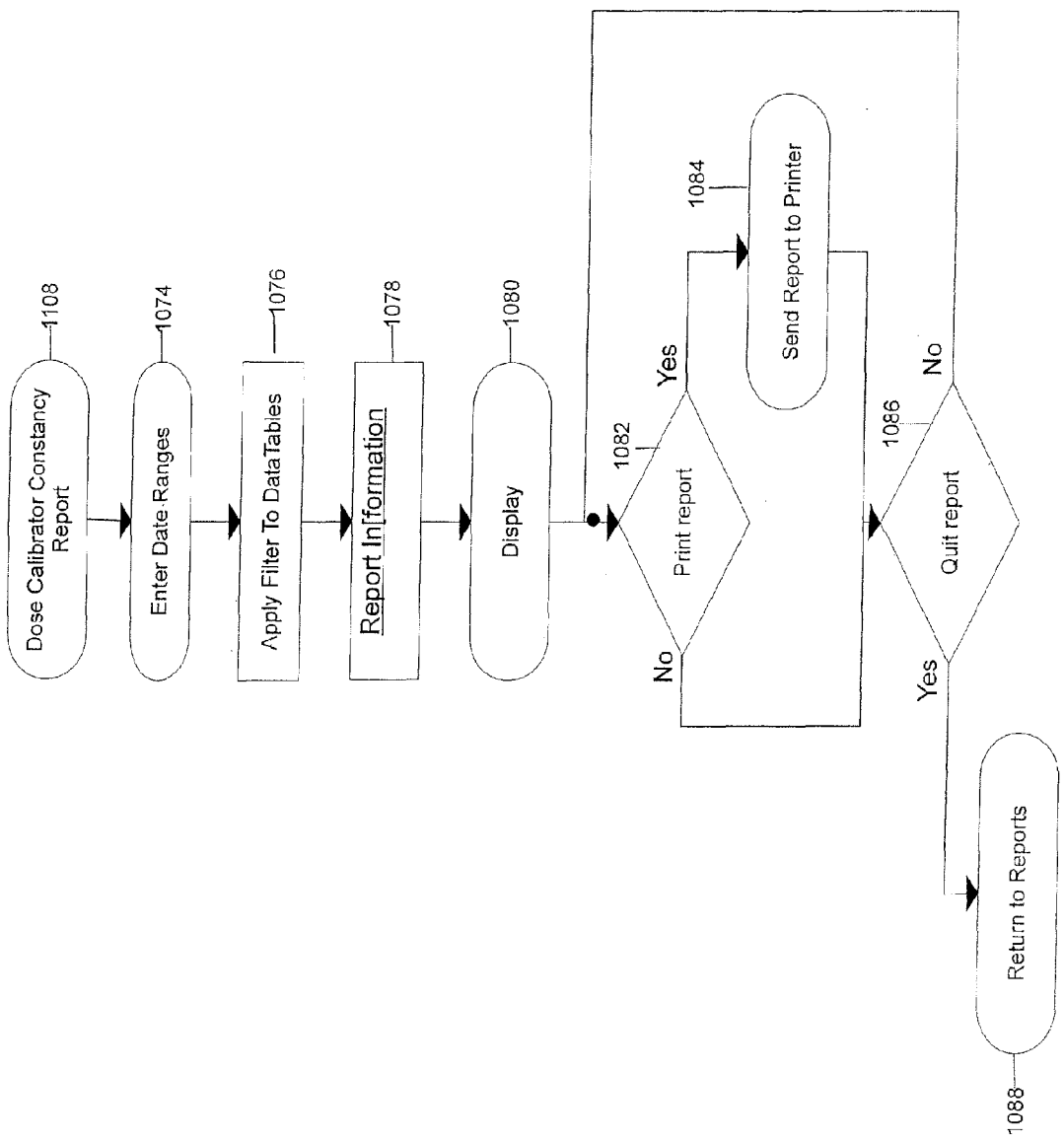
Figure 62:
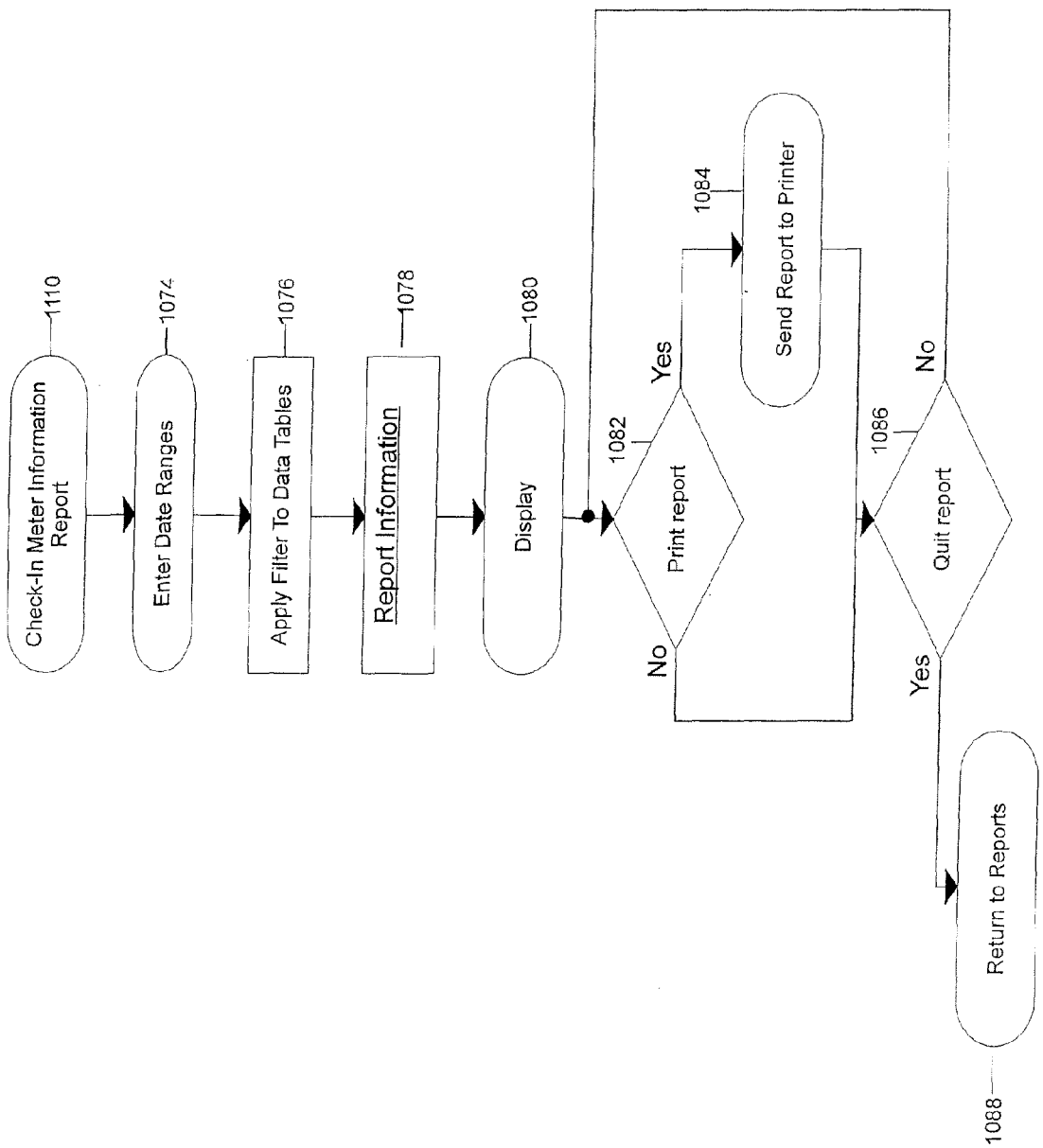
Figure 63:
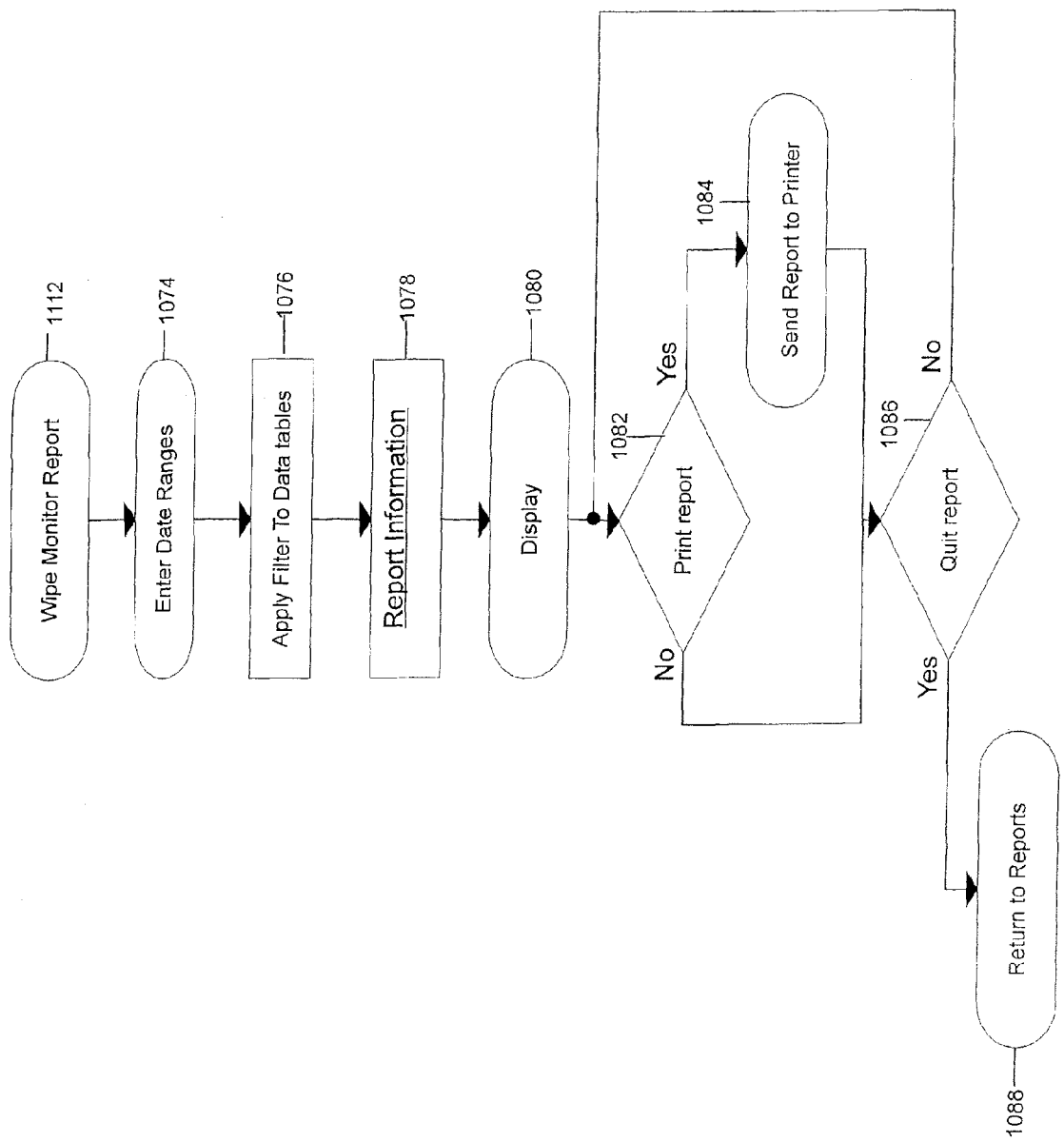
Figure 64:
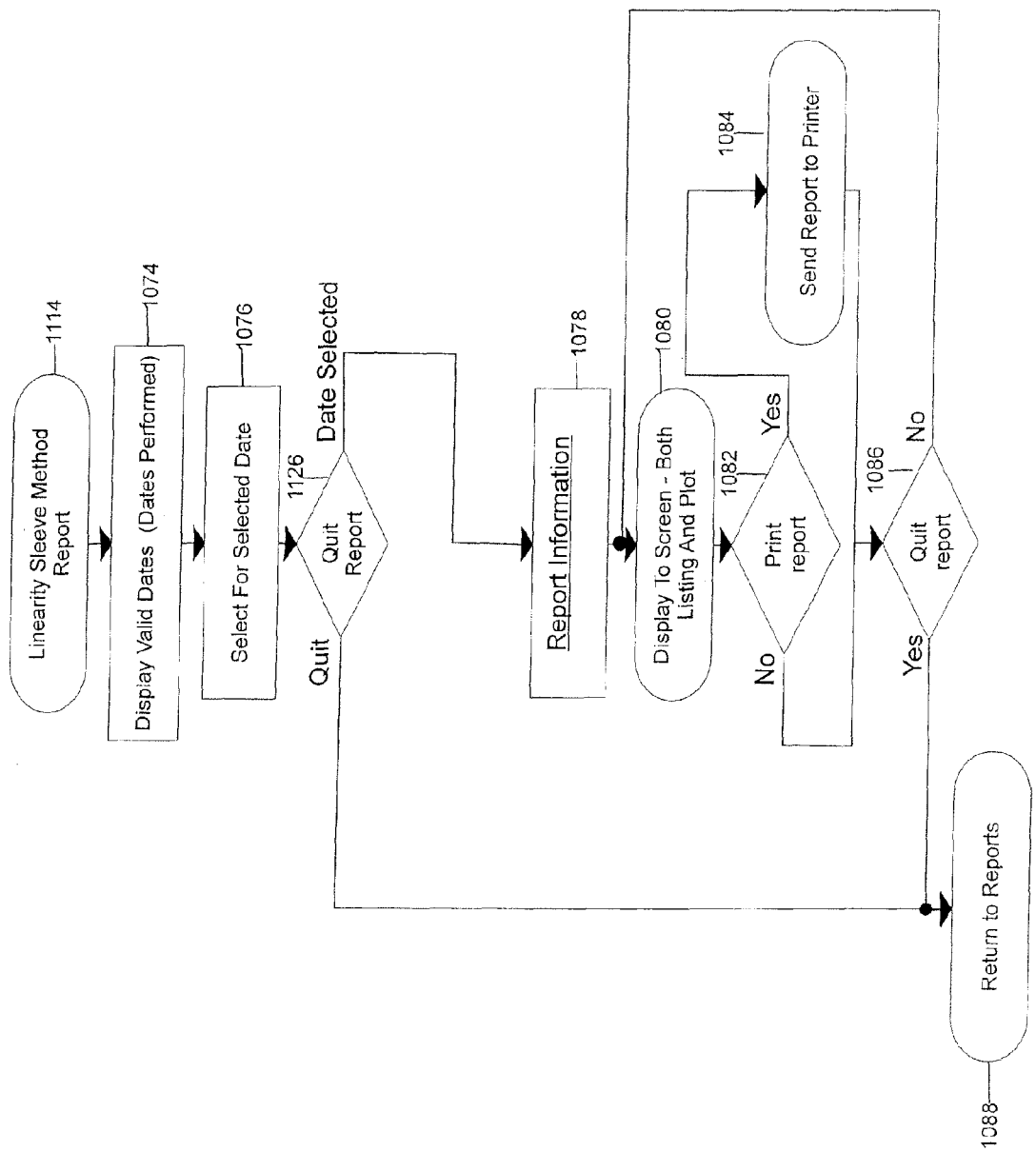
Figure 65:
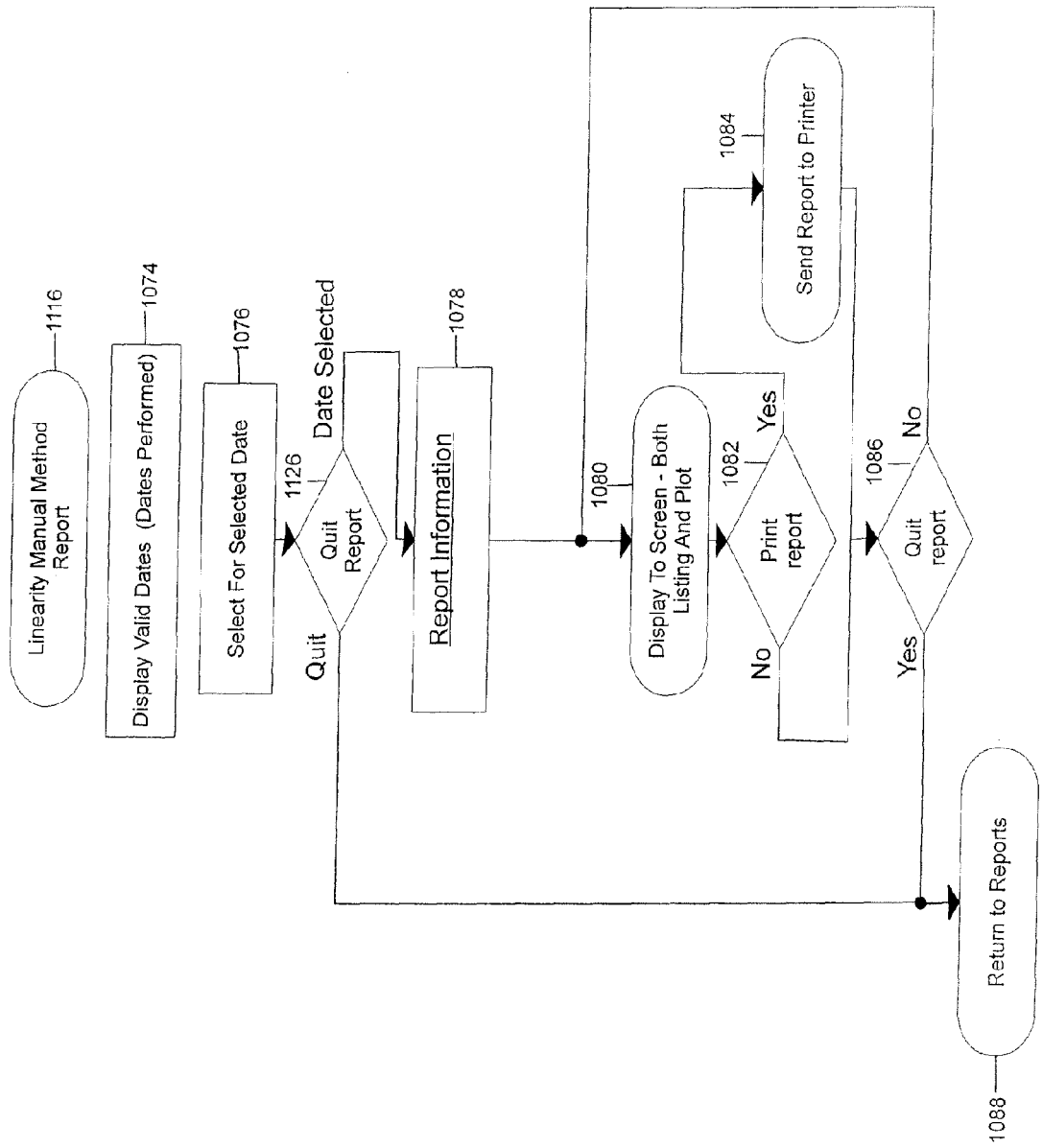
Figure 66:
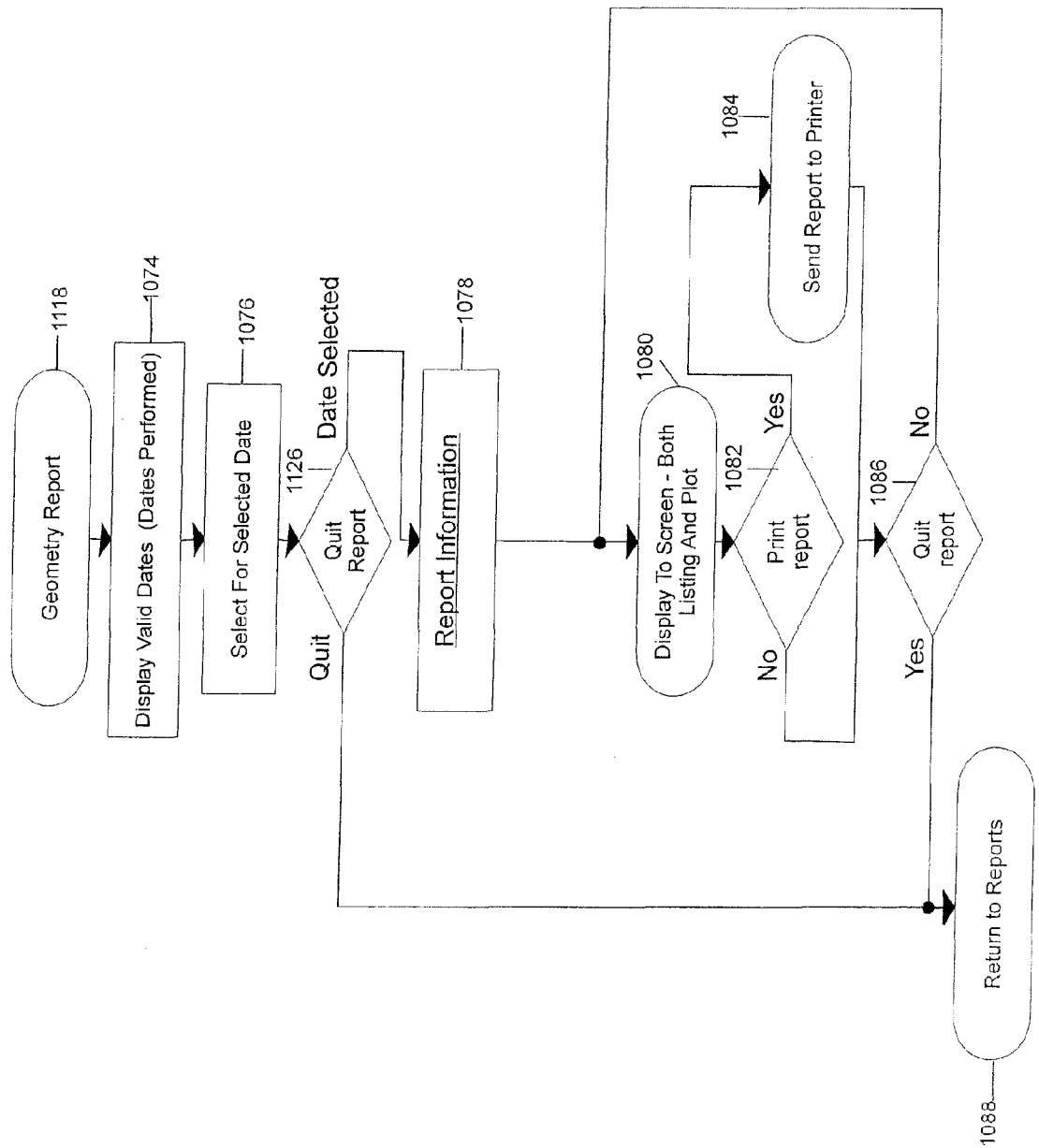
Figure 67:
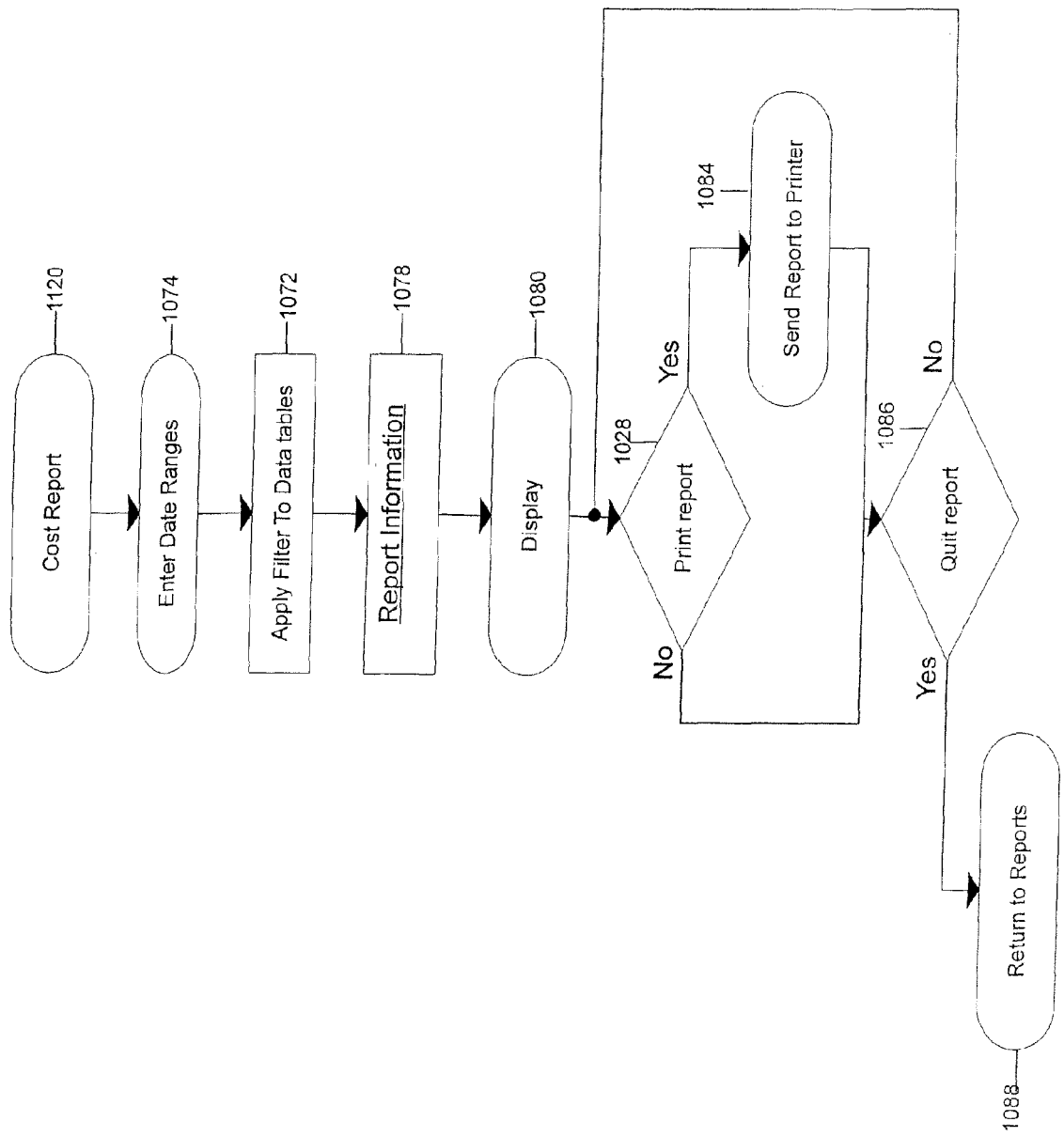
Figure 68:
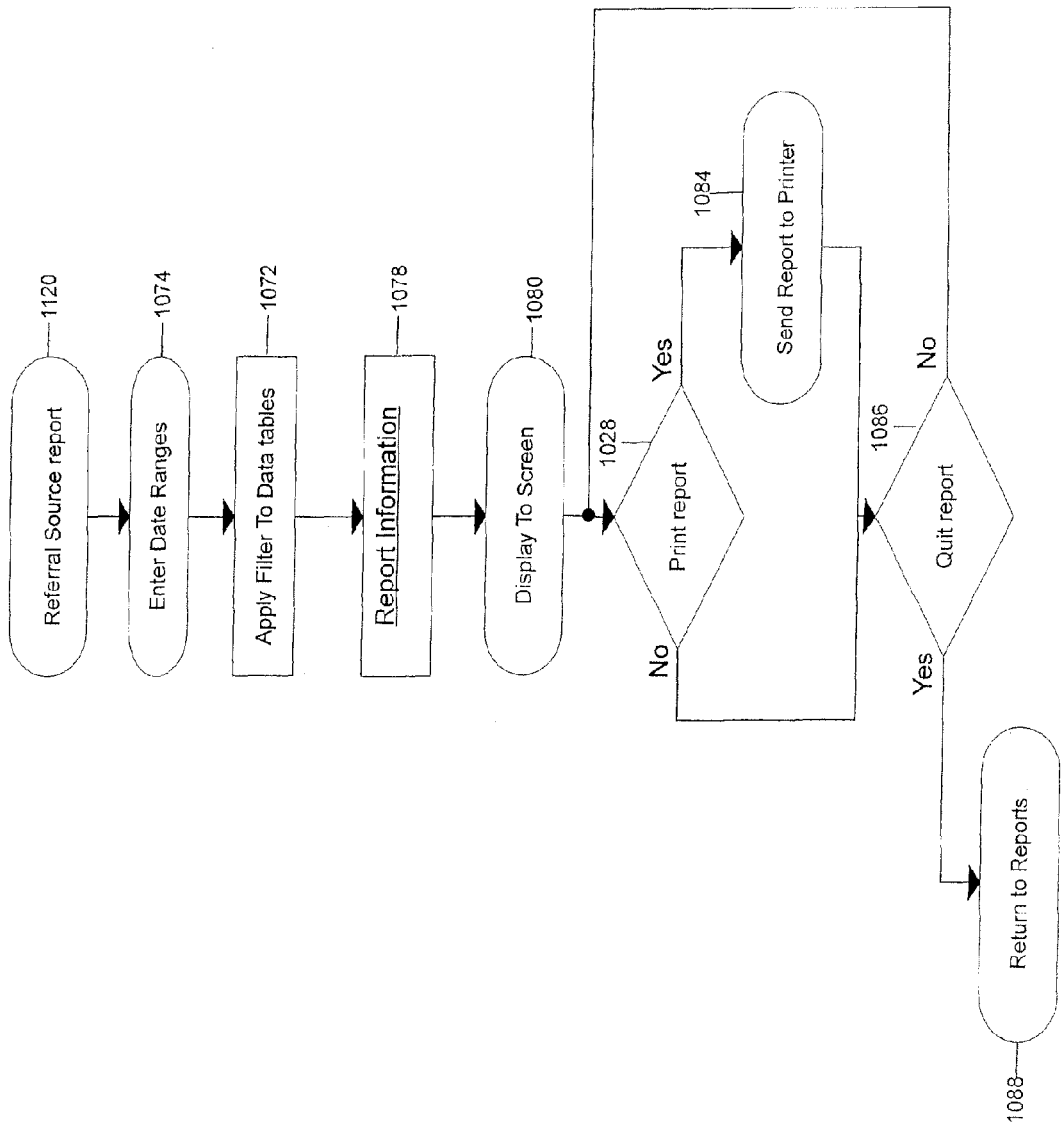
Figure 69:
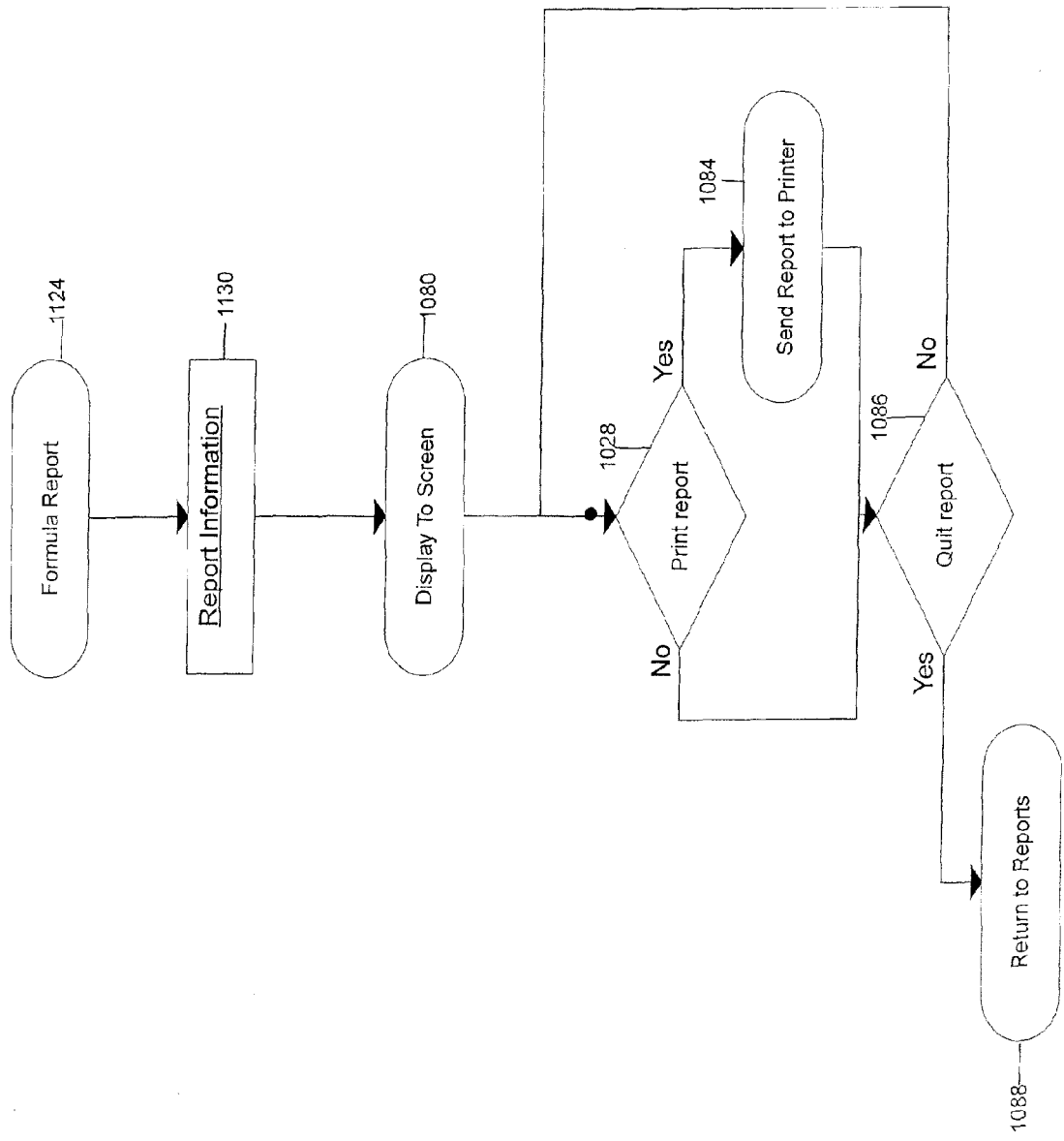
Figure 70:
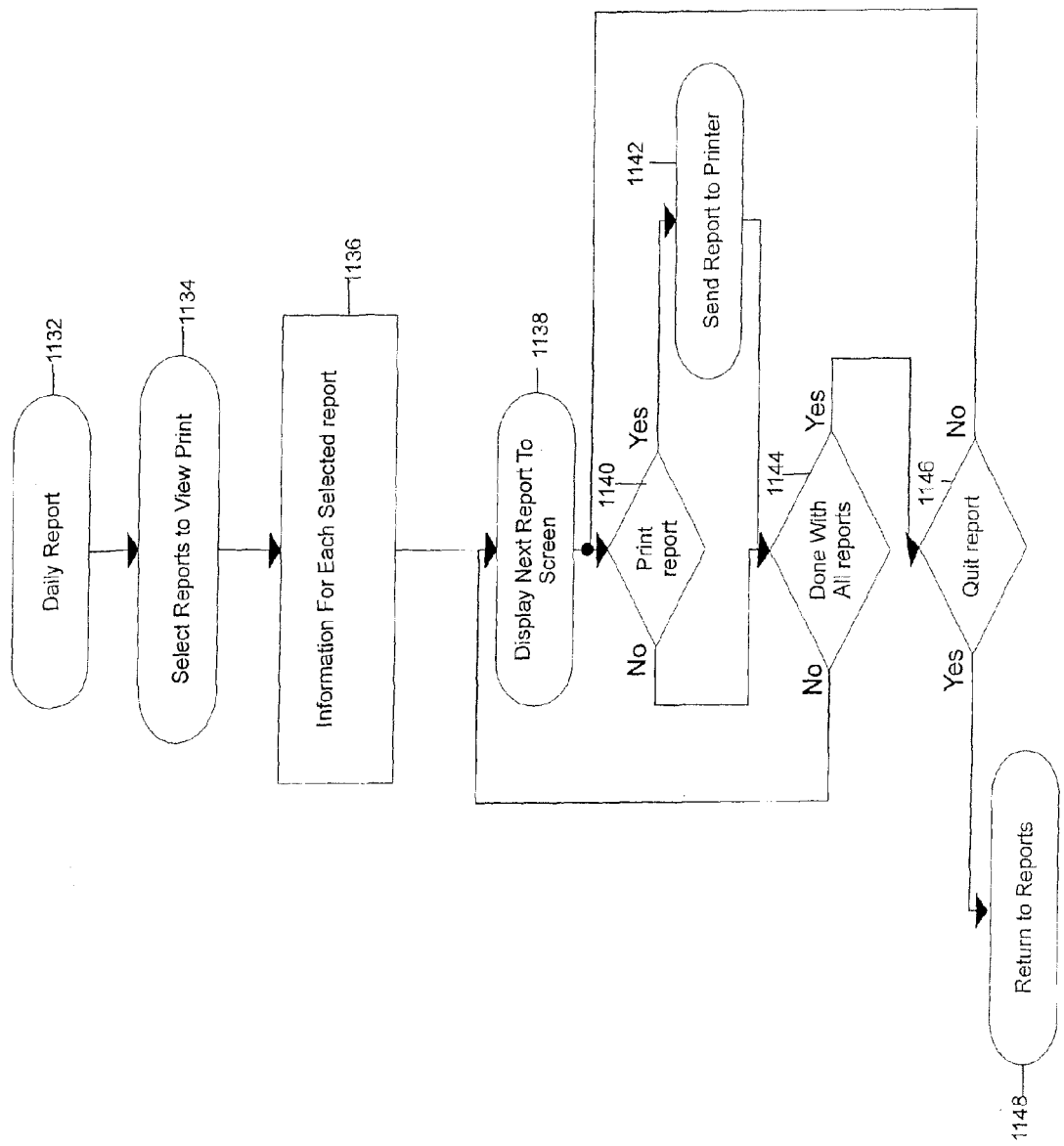

Having thus described the invention in general terms, reference will now be made to the accompanying drawings in which:

FIG. 1 is a symbol identification of the various symbols used in the following schematic block diagram flow sheets, forming part of the algorithm and method of the present invention;

FIG. 2 is a schematic block diagram flow sheet, showing the main steps forming part of the main loop in the algorithm and method of the present invention;

FIG. 3 is a schematic block diagram flow sheet, showing the steps involved in the scheduling of patients;

FIGS. 4A and 4B are schematic block diagram flow sheets, showing the steps involved in the programming for the receipt of doses to be administered to patients;

FIG. 5 is a schematic block diagram flow sheet of a chart showing those steps involved in viewing available doses for the various patients, in accordance with the present invention;

FIGS. 6A and 6B are schematic block diagram flow sheets, showing the selection of dosage per patient, in accordance with the algorithm and method of the present invention;

FIG. 7 is a schematic block diagram flow sheet, showing the steps involved in the ordering of doses, in accordance with the algorithm and method of the present invention;

FIGS. 8A and 8B are schematic block diagram flow sheets, showing the steps involved in the selection of a software administrator, that is, administration of the software allowing for the algorithm and the method of the present invention;

FIG. 9 is a schematic block diagram flow sheet, showing the steps involved in the selection of hot labs, that is, analyzing the conditions of radioactive laboratory operations;

FIG. 10 is a schematic block diagram flow sheet, showing the selection of reports for various activities which are performed initially in the algorithm and method of the present invention;

FIG. 11 is a schematic block diagram flow sheet, showing the disposal operations for disposing of radioactive pharmaceutical material and material contaminated thereby;

FIG. 12 is a schematic block diagram flow sheet, showing the select dose calculations formed by the algorithm and the method of the present invention;

FIG. 13 is a schematic block diagram flow sheet, showing the steps involved in the selection of dates and times for performing various activities and for setting those dates and times in the program of the invention;

FIG. 14 is a schematic block diagram flow sheet, showing the printing of a schedule in accordance with the invention;

FIG. 15A is a schematic block diagram flow sheet, showing the steps involved in a survey meter validation, in accordance with the present invention;

FIG. 15B is a schematic block diagram flow sheet, showing the steps involved in a wipe meter validation, in accordance with the present invention;

FIG. 16 is a schematic block diagram flow sheet, showing the steps involved in a daily constancy, that is, calibrating measurements involved in the use of radioactive materials in the hot labs of the present invention;

FIG. 17 is a schematic block diagram flow sheet, showing determination of dose accuracy in accordance with the present invention;

FIG. 18 is a schematic block diagram flow sheet, showing linearity sleeve steps used for performing the determination of fill calibration factors, input assayed amounts and calculated calibration factors;

FIG. 19 is a schematic block diagram flow sheet, showing a linearity manual method for calibration information, assayed activity and the retention thereof;

FIG. 20 is a schematic block diagram flow sheet, showing those steps involved in the geometry for calibration information and assayed activity, as well as calculations therefor;

FIG. 21 is a schematic block diagram flow sheet, showing the incorporation of physician information, that is, information relating to the physician prescribing such radioactive pharmaceuticals;

FIG. 22 is a schematic block diagram flow sheet, showing the insurance information involved with the dispensing of the radioactive pharmaceuticals, for purposes of billing and like activities;

FIG. 23 is a schematic block diagram flow sheet, showing those steps involved in information about scheduling activities;

FIG. 24 is a schematic block diagram flow sheet, showing steps involved in setting forth information regarding the room of a particular patient, to thereby ascertain the location of that patient;

FIG. 25 is a schematic block diagram flow sheet, showing the steps involved in determining dose information for a particular patient, in accordance with the present invention;

FIG. 26 is a schematic block diagram flow sheet, showing source information in accordance with the present invention;

FIG. 27 is a schematic block diagram flow sheet, showing the steps involved in source disposal, that is, disposal of sourced radioactive material, in accordance with the invention;

FIG. 28 is a schematic block diagram flow sheet, showing the steps involved in maintaining an inventory of radioactive material in accordance with the present invention;

FIG. 29 is a schematic block diagram flow sheet, showing the steps involved in patient dose information, that is, the dosages of radioactive material already administered to patients;

FIG. 30 is a schematic block diagram flow sheet, showing the steps involved in task information, that is, those tasks necessary and the days, months and weeks for administration of the algorithm and method of the present invention;

FIG. 31 is a schematic block diagram flow sheet, similar to FIG. 30, and shows additional test information generated and stored in accordance with the algorithm and method of the present invention;

FIG. 32 is a schematic block diagram flow sheet, showing steps involved in the recording of schedule information, in accordance with the present invention;

FIG. 33 is a schematic block diagram flow sheet, showing the steps involved in recording all information regarding meter probes used in the process and algorithm of the present invention;

FIG. 34 is a schematic block diagram flow sheet, showing steps involved in the meter analysis for the meters used, in accordance with the algorithm and process of the present invention;

FIG. 35 is a schematic block diagram flow sheet, showing those steps involved in the monitoring of various items used in the dispensing and recording of information regarding radioactive pharmaceuticals;

FIGS. 36A and 36B are schematic block diagram flow sheets, showing the steps involved in monitoring groups of individuals treated with the radioactive pharmaceuticals of the invention;

FIG. 37 is a schematic block diagram flow sheet, showing the steps involved in a dose calibration in accordance with the present invention;

FIG. 38 is a schematic block diagram flow sheet, showing the measurements set forth in a dose calibrator constancy method, in accordance with the present invention;

FIG. 39 is a schematic block diagram flow sheet, showing the steps involved in the method of editing the dose calibrator constancy, and is similar in that respect to FIG. 38;

FIG. 40 is a schematic block diagram flow sheet, showing the steps involved in editing of dose accuracy in accordance with the algorithm and method of the present invention;

FIG. 41 is a schematic block diagram flow sheet, showing those steps involved in the editing of sleeves used in the production of the radioactive pharmaceuticals;

FIG. 42 is a schematic block diagram flow sheet, showing the steps involved in the calibration of linear sleeves used in the preparation of the radioactive pharmaceuticals;

FIG. 43 is a schematic block diagram flow sheet, showing the steps involved in the editing of the linear sleeves dealing with decay of the radioactive material;

FIG. 44 is a schematic block diagram flow sheet, showing the geometry of preparing and using the dose calibrator to determine doses of the radioactive pharmaceuticals to be administered;

FIG. 45 is a schematic block diagram flow sheet, showing the steps involved in the manual decay of the radioactive pharmaceuticals, and typically referred to as the editing of the linear calibration;

FIG. 46 is a schematic block diagram flow sheet, and illustrates the decay of the radioactive material in storage and the determination thereof;

FIG. 47 is a schematic block diagram flow sheet, showing a chart setting forth the various options for dosing a patient;

FIG. 48 is a schematic block diagram flow sheet, showing the steps involved in the scheduling of various patient options;

FIG. 49 is a schematic block diagram flow sheet, showing the steps involved in the recording of dates for filtering of the doses to be administered;

FIG. 50 is a schematic block diagram flow sheet, showing the steps involved in preparation of a dosage shipment report;

FIG. 51 is a schematic block diagram flow sheet, showing the steps involved in preparation of a tests performed report;

FIG. 52 is a schematic block diagram flow sheet, showing the steps involved in preparation of a disposal report;

FIG. 53 is a schematic block diagram flow sheet, showing the steps involved in preparation of a container return report;

FIG. 54 is a schematic block diagram flow sheet, showing the steps involved in the preparation of a residual inventory report;

FIG. 55 is a schematic block diagram flow sheet, showing the steps involved in the preparation of a patient status report;

FIG. 56 is a schematic block diagram flow sheet, showing the steps involved in the preparation of a patient information report;

FIG. 57 is a schematic block diagram flow sheet, showing the steps involved in the preparation of a patient look up report, that is, a report with information about a particular patient;

FIG. 58 is a schematic block diagram flow sheet, showing the steps involved in the preparation of a dose calibrator accuracy report;

FIG. 59 is a schematic block diagram flow sheet, showing the steps involved in the preparation of a sealed source inventory report;

FIG. 60 is a schematic block diagram flow sheet, showing the steps involved in the preparation of an area report;

FIG. 61 is a schematic block diagram flow sheet, showing the steps involved in the preparation of a dose calibrator constancy report;

FIG. 62 is a schematic block diagram flow sheet, showing the steps involved in the preparation of a meter information report;

FIG. 63 is a schematic block diagram flow sheet, showing the steps involved in the preparation of a wipe monitor report;

FIG. 64 is a schematic block diagram flow sheet, showing the steps involved in the preparation of a linearity sleeve method report;

FIG. 65 is a schematic block diagram flow sheet, showing the steps involved in the preparation of a linearity manual method report;

FIG. 66 is a schematic block diagram flow sheet, showing the steps involved in the preparation of a geometry report;

FIG. 67 is a schematic block diagram flow sheet, showing the steps involved in the preparation of a cost report;

FIG. 68 is a schematic block diagram flow sheet, showing the steps involved in the preparation of a referral source report;

FIG. 69 is a schematic block diagram flow sheet, showing the steps involved in the preparation of a formula report;

FIG. 70 is a schematic block diagram flow sheet, showing the steps involved in the preparation of a daily report; and FIG. 71 is a schematic block diagram showing the fields in which data is introduced, and the accumulation of data for injection of a particular patient.

DETAILED DESCRIPTION OF A PREFERRED EMBODIMENT

The algorithm of the present invention is more fully described by reference to the following FIGS. 2-71. It should be recognized that this particular algorithm and method are primarily adapted for use with the medical facility, including individual physicians, although it could be adapted for use with a pharmacy or other facility authorized to dispense radioactive pharmaceuticals.

FIG. 1 illustrates the symbology which is used, and to that extent, is self explanatory with regard to data entry and processing of data, as well as a decision point. The decision point typically has more than one output, such that if a decision is "yes", for example, then one output occurs, and if a decision is "no", then another output occurs. The term "link to slide" identifies shifting to a particular flow chart. Thus, in the actual algorithm one can automatically move to a selected subroutine, illustrated on these various figures.

Each of the following routines are identified with a description of each routine. To a large extent, many of the steps are self explanatory, and do not require further explanation.

The main loop represents the start of the program and the various activities which take place. Some of the routines defined by these activities are hereinafter set forth in more detail. It can be observed that the algorithm generally loads any default information at Step 100, as for example, the default would include names and information. Next, the program will then show on a monitor the day's appointments at Step 102, and to also identify the tasks at Step 104.

At this point, the main program provides for a decision of the operator at Step 106, to either quit the program or to proceed with the program. If the decision is to quit the program, then the algorithm will cause the return to the showing of appointments. If the operator elects to continue with the program, the algorithm will then display a schedule patient routine 108, where the operator will schedule a particular patient. All of the information concerning that patient is introduced. In addition, the operator can either introduce, or can have previously introduced information displayed, about receipt of doses of pharmaceutical material at Step 110. The viewing of these doses are available at Step 112.

After the determination of the dose is made, the patient is actually dosed at Step 114, that is, the radioactive pharmaceutical is administered to the patient. That administration may occur at a hospital or a physician's office. However, that information must be sent back to the scheduler or individual who maintains the record keeping information for introduction into the data processing program. In this way, it is possible to keep track of the doses which were administered to a particular patient, and to also control inventory and the like.

Doses are ordered at Step 116. In this case, the algorithm is arranged so as to advise the operator of doses which must be ordered, as for example, from a radioactive pharmacy, and the next time period in which they must be ordered. As a simple example, if a particular patient requires a radioactive pharmaceutical on a periodic basis, that information is introduced into the electronic data processing system, and the information necessary will be displayed on a timely basis. As an example, for each patient requiring a particular pharmaceutical that day, the information will be displayed, thereby enabling the operator to advise the necessary personnel to otherwise order the doses, or to prepare the doses on an in-house basis.

The algorithm is provided with a routine identified as selection of a software administrator Step 118, or otherwise, software administrator tasks. In this case, a display screen may generate information about each of the tasks which the administrator is to perform. Moreover, the term "administrator" is typically referred to as that party who is monitoring the information on a display and introducing information. Details of the software administrator task is more fully set forth in connection with the description of FIGS. 8A and 8B. In essence, a single display can generate all of the routines to be required and the order in which they take place, so that the administrator or the scheduler can keep track of and insure that all activities are correctly performed.

The algorithm next presents a routine identified as "hot labs". In this case, the term "hot labs" refers to those activities, such as monitoring, cleaning and the like, which take place in those areas and with those instrumentalities involved in the actual contact with radioactive pharmaceuticals. Thus, and for example, this term encompasses those activities for measurement of radioactivity levels on counters, and other fixtures in a facility. It also provides for various subroutines dealing with disposal of radioactive instrumentalities, such as syringes, vials and the like. Indeed, the latter is an integral part of the administration of radioactive pharmaceuticals and subroutines are also provided in connection with the description of FIG. 9 of the drawings, each subroutine is presented on a different screen in the order to be performed and the necessary steps for each subroutine are set forth therein.

As indicated previously, reports are a critical part of dealing with any radioactive material, and in this case, radioactive pharmaceuticals. Consequently, a separate routine is provided for preparing reports at 122. In addition, disposal of the instrumentalities used in administration of the radioactive pharmaceutical are also important at Step 124.

The algorithm also provides other routines, such as selection of a particular word processor at Step 126, but which is not necessarily described in any further detail herein. However, that operation is fairly simple and standard in that the operator can select a particular desired word processing program. A dose calculation is performed at 128. Form information is introduced at Routine 130, backup information at Step 132, and help information at Routine 134. These various routines, such as the forms Routine 130, the backup Routine 132, and the help Routine 134, are only aids to the operator, but are not critical to the algorithm, and therefore, have neither been illustrated nor described in any further detail herein. However, the date and time setting at Routine 136 is important, in that all of the activities which take place are controlled by the date and time. Again, since the algorithm deals with administration of radioactive pharmaceutical materials, it is necessary to maintain accurate timing for delivery to each of the patients at a prescribed time, and to order the materials at a prescribed time. For this purpose, there is an update time Routine 138. The operator can also terminate the algorithm at Routine 140.

FIG. 3 illustrates the routine for scheduling of patients, namely, that Routine 108. In this case, the routine includes an initialization 142, which displays current appointments. The operator then can decide whether to schedule or not schedule at Step 144. If scheduling is to be stopped, the algorithm will return to the main loop at Step 146, and if scheduling is to be performed, the algorithm will move to Step 148 for scheduling of a new appointment. The operator the selects the type of schedule, whether a single or a multi-information schedule, at Step 150, or otherwise, can print the schedule at Step 152.

When introducing multiple patient information, and for that matter, when introducing single patient information, the algorithm allows for introduction of and the concomitant display of information, such as the date, the room in which a patient may be located, the name of the patient, the sex of the patient, weight, birth date, city and state, and address, as well as diagnosis and notes. This information is introduced in both multiple or single patients at Step 154 for multiple patients, and Step 156 for single patients. In addition, insurance information, physician information and the scheduler, can also be introduced. There is also a subroutine 158 for change of appointments. These appointments can be changed and saved at Step 160.

When a schedule for one or more patients is needed, it is possible to print that schedule at Step 162. It is also possible to use the information to order a radioactive pharmaceutical to be administered to a patient at Step 164. Information regarding the administration of a dose is displayed at Step 166. There is also provision for changing of room date and the like at Step 168, and renewal of appointments at Step 170.

With regard to the actual dosage to be administered to a patient, reference is made to FIG. 4A and FIG. 4B which show the receiving of doses in Routine 110. In the routine of receiving a dose, current doses are displayed at Step 172. A decision is made at Step 174 to either receive doses or to not receive further doses. If there is an election to receive no further doses, the algorithm automatically returns to the main program at Step 176. If there is an election to receive further doses, then there is provided an initial handling display Step 178, in which information must be entered. In this case, information such as the date and time of receipt of material, the condition of the container, placement of the packages and the labels removed, can be introduced.

Thereafter, at Step 180 a decision is made to determine whether or not a cold dose will be administered. In this case, a decision to introduce other than a cold dose would be directed to Step 182, where a survey meter is then validated. The survey meter provides background surface information at Step 184. Also, a selected wipe meter is validated at Step 186. In this case, the wipe meter area is determined at Step 188, and the measurement of any contamination from wipe areas by cotton swabs and the like can be recorded and presented. Thus, the wipe meter can determine the amount of radioactivity at particular locations which have been wiped with a swab or the like.

The algorithm next moves to Step 190, which shows the entry of a dose. When a dose is entered, the bar code on the bottle, or other vial containing that dose, is examined at Step 192, as best shown in FIG. 4B. If the vial or other container is scanned, the information on the bar code is interpreted and displayed at Step 194. Product information may also be introduced at Step 196, and include, for example, the type of product, the volume, the calibration date, activity date, and the expiration date. If the dose is not scanned, product information can be manually introduced at Step 198, and this may include the same type of information at Step 196.

A determination can then be made at Step 200, as to whether or not the bar code is valid. This data can then be saved at Step 202, and can be modified at Step 204. If the information is modified, then the algorithm will shift to a display of entering doses 206. If there is no modification of the information, then a Step 206 will allow the operator to either quit and return to the main loop, or otherwise, to refresh the current dose, including for example, filter, expiration date and time, and current date and time at Step 208.

In order to view the available doses in inventory by an operator, the step of selecting the available doses at Step 210, can be used. This will show available doses and filter information, as well as the expiration date and time, and the current date and time, at Step 212. At this point, a decision is made by the operator at Step 214 as to whether or not to quit the viewing of available doses and if the operator elects to quit such viewing, the algorithm returns to the main loop at Step 216. If there is a decision to continue viewing, a decision is also made at Step 218 to enter new dose information.

New dose information provides a series of decisions for entering this new dosage. A first decision at Step 220 determines whether a filter is unavailable, and at Step 222 a determination is made as to whether a filter is available. At Step 224, a decision is made as to whether or not all material is to be filtered. In each case, there is a display at Steps 226, 228 and 230, for each of the previous three decision steps, which show unavailable doses, available doses and, finally, available and unavailable doses.

A routine for selecting a dose for each patient is provided, that is, Routine 114, is shown in FIGS. 6A and 6B of the drawings. In this case, a display of a selection of a dose per patient is made at Step 232. This will display, at Step 234, the available doses only, the filter and time information, that is, the expiration date and time, and the current date and time, and the filter appointment date and the current date. A decision is then made by the operator to stop the dosing routine at Step 236. If there is an election to stop the dosing display, then the algorithm will return to the main loop. If there is no decision to stop dosing, the algorithm will then allow additional information to be introduced and displayed. Thus, a decision is made as to whether or not a patient is to be dosed at Step 238.

If a patient is not scheduled, a decision is made as to whether or not to schedule a new appointment at step 240, the appointment can then be made and displayed at Step 242. At Step 244, if a patient is scheduled for a new dosage, the available doses of the selected type will be displayed. This will also include filter information for the doses, whether or not they are available, the expiration date and time, and the current date and time. In addition, it is possible to edit the appointments at Step 246. In the editing, as indicated, an appointment can be scheduled at Step 242, or otherwise, an appointment could be deleted at Step 248. This will display and take place at Step 250.

If there is no deletion of appointments, then it is possible for the operator to show all product at Step 250. In this case, again, all the available doses are shown at Step 252. At this point, the patient can be dosed with information at Step 254. A decision is made as to whether or not the patient should be dosed at Step 256, and if so, a decision is made as to the doses which are available at Step 258. If there is no new dose available, then a decision must be made as to whether or not new doses must be received at Step 260. If new doses are to be received, that information can then be displayed at Step 262. Otherwise, it is possible to select a different dose at Step 264.

If doses of a desired radioactive pharmaceutical are available, then it is possible to measure the amount of radiation for those one or more particular doses at Step 266. In this case, the control amounts, that is, the amount of radiation can be measured or determined, the amount to be administered can be presented or introduced, the residual amount, that is, the amount of radiation in a syringe after administration, and the date, time and initials of the party entering such information can be also entered. Thereafter, a decision is made as to whether or not a particular pharmaceutical is administered at Step 268. From there, the maintaining information on the actual administration is finished at Step 270. After determination of the administration information at Step 270, the routine returns to Step 234, in order to operate the same routine, again, for additional patients.

If doses are to be ordered for a patient at Routine 116, a display for ordering of doses occurs at Step 272, as shown in FIG. 7. In this case, a display 272 will show today's orders and the date for which a new order should be made, that is, a selected date. If the ordering of a new dose does not take place, then the routine will return to the main loop. Otherwise, if a new dose is to be ordered at Step 276, then the date for which the order is to be made is introduced at Step 278, and this may include such information as the date and time and the comments of the operator.

If an order is made at Step 278, a determination is made as to whether or not the order is manually entered at Step 280. In this case, if the order is not manually entered, the order will have to be printed at Step 282 and sent to a source, such as a radioactive pharmacy, for delivery. Alternatively, the order can be sent by a fax or e-mail, at Step 284. If there is a manually entered order at Step 280, information such as the date and time, test product information and amounts of units available, can be introduced at Step 286. This information can be saved at Step 288 and Step 290, and then used for updating orders at Step 292. That information is then introduced into the manual entry of orders at Step 280.

Another main menu dealing with administration is shown in FIGS. 8A and 8B, and deals with the selection of software administrator at Step 292, and the tasks therefor, at Routine 118. The selection of the software administrator deals with administration information, such as the physicians, and the insurance which may be available, rooms, management of the source of radioactive pharmaceuticals, editing and monitoring steps, the management of doses and the like.

This administration at Routine 118 is more fully illustrated in FIGS. 8A and 8B, as aforesaid. It can be observed that after the software administration is selected at Step 292, it is possible to either stop at Step 294 and return to the main loop, or otherwise, to proceed and move to Step 296. After an operation is selected at Step 296, it is possible to move to a main set up display 298. From this, physician information can be handled at Step 300, insurance information at Step 302, scheduling information at Step 304, and rooms for a particular patient at Step 306. In this case, either information can be displayed, and in like manner, for Steps 300 through 306, it is also possible to introduce information.

Another subroutine would involve the inventory of the radioactive pharmaceutical is provided at Step 308. In this case, the source of radioactive material at 310 can be displayed or entered in that step identified as sources management. At source disposal, the information regarding the disposal of a radioactive pharmaceutical can be displayed or entered at Step 312. The dose information can be entered or displayed at Step 314, editing information at Step 316, and editing doses at Step 318. In the case of editing the inventory and editing the doses, a determination is made as to the life of the radioactivity in those particular doses. A system subroutine at Step 320 is also provided for tasks at Step 322, such as area monitoring, tests for a single dose at Step 324, and study step 326 for multiple tests.

A dose management subroutine 328 is also provided and is, in effect, an inventory subroutine. In this case, each of the following steps can either be a display of information or an entry of information. Thus, meter probe information can be displayed or introduced at Step 330, the status of a survey meter can be made or data regarding same can be entered at Step 332, and a wipe meter at Step 334. The term "wipe meter" does not necessarily refer to a particular type of meter, but rather, that meter which is used for measuring the amount of radioactivity absorbed by a swab. The term "survey meter" similarly does not refer to a particular meter per se, although it may, and generally refers to direct measurements of items, such as those instrumentalities used in the handling of the radioactive pharmaceutical, e.g., syringes and the like.

Monitor items information can be introduced or displayed at Step 336, wipe items at Step 338, monitor groups at Step 340, and wipe groups at Step 342. In like manner, dose calibrator information can be entered at Step 344, and a constancy set up, which is also a dose calibrator, can be introduced or displayed at Step 346. Again, the term "dose calibrator" does not refer to a particular type of calibrator, but rather, the calibration of the amount of radioactivity in a selected dose.

The system subroutine 320 also includes various related functions, such as a backup data system which may be displayed or entered at Step 348, available forms at Step 350, registration of information at Step 352, and word processing at Step 354. In actuality, Steps 352 and 354 are not really necessary in connection with the algorithm of the invention.

In order to produce the various doses of radioactive pharmaceutical in the dose management subroutine 238, the sleeves which are used for producing the radioactivity, as in Step 356, can be displayed or entered. In effect, this is a dose calibration and is usually performed on a daily basis, in order to determine the decay of a source of radioactive material. A DC constancy information can be displayed or introduced at Step 358, sleeves can be calibrated at Step 360, and a dose accuracy edit can be made at Step 362. The term "DC" calibrator at Step 366 typically refers to a dose calibrator and provides the accuracy thereafter. In this case, linearity measurements provide for a check and balance of the linearity of the radioactive material. For example, since it is known that the radioactivity will decay over a period of time, it is possible to determine how linear the decay may be, and the amount of that decay.

The determination of a dose calibrator accuracy uses a known source, such as, for example, 50 millicuries of product introduced into a dose calibrator. Three readings are made, and if neither has a X % deviation, as for example, a 5%, deviation, the meter is calibrated, otherwise, that meter must be re-calibrated.

An editing of sleeve linearity information can be either displayed or information introduced at Step 364, a DC calibrator geometry at Step 366, an edit of a linear manual introduction at Step 368, and a decay in storage editing can be made at Step 370. The term "linearity" by the sleeve method, or otherwise, "sleeve linearity", essentially refers to the insertion of a container or other instrumentality into a lead sleeve, or other sleeve, which will block radiation. In effect, the sleeve blocks at least a portion, but not all, of the radiation and so, therefore, it is necessary to calibrate all of the sleeves used in the system. The amount of radiation normally blocked by a sleeve is known. However, since there will be a decay factor, it is known that one must compare that to a standard. In this way, there is a dual check.

At this point, contrast to the linearity method is also to be noted. In the linearity method, it is known that radiation will also degrade according to a logarithmic decay. If an instrument is being examined, in order to determine its accuracy, it is possible to readily determine the amount of radiation which decay. For example, if a product of a known isotope, having a known decay, of e.g., sixty hours is taken, those measurements can be made over an interval and any fault in the instrument in making measurements can be determined.

From the selection of the operation at Step 296, it is also possible to elect a preference step at 372, as best shown in FIGS. 8A and 82. From this an operation is selected at Step 374, and on a main screen, a display is made at 376 and classification data can be entered at Step 378. A dosage of a patient can be displayed at Step 380, and after dosing thereof, at Step 382 it is possible to determine and use residual amounts, link additional dosages after injection, and percent of allowance on injection. The select operation Step 374 also allows for scheduling of patients at Step 384. In this case, several fields for information are presented, as for example, a sex field, birth date field, weight, address, diagnosis, insurance, and physician information. A printing operation can be actuated under the select operation subroutine 374, such as printers in Step 388. Default of the printing operation at Step 390 will allow for return at Step 392 through the initiation of the software administrator routine. Several of these subroutines and the associated steps are hereinafter described in more detail.

With regard to that routine identified as "hot labs" in Step 120, the steps of that routine are more fully set forth in FIG. 9. In order to select the hot labs subroutine, either information is displayed or processed at Step 394. A decision is then made by the operator at Step 396 to either terminate the hot labs routine and return to the main menu, or otherwise to continue and select a hot lab operation at Step 398. As indicated previously, the term "hot labs" refers to measurement of the amount of radioactivity in an instrumentality or in a radioactive pharmaceutical. Thus, a dose calibrator constancy or so-called "daily constancy", can be displayed at Step 400. In each of the following steps, the information can either be displayed, or otherwise, information can be introduced.

The accuracy of any determination is introduced at Step 402. Thereafter, a determination can be made as to whether or not there is going to be a linearity sleeve analysis at Step 404, or the use of a linearity manual method at Step 406. A geometry, that is, the amount introduced into a container can be made at Step 408. A sealed source inventory, that is, how much radioactive pharmaceutical is present in the facility, can be made at Step 410. No operation at Step 412 would cause a return to the beginning of this subroutine.

The linearity sleeve method generally involves the use of a sleeve to be inserted around a bottle or like device. The sleeve is preferably formed of a lead material so that the amount of radiation decay is minimal. In this case, a known isotope is used for reference purposes. Normally, it may take a substantial period, as for example, sixty hours to measure decay in some radioactive materials. This measurement informs the user almost instantaneously about any fault in the instrument making the measurements. In short, this step allows for the calibration of any meters which make measurements.

FIG. 10 illustrates the subroutine of reports 122, and constitutes an important aspect of the algorithm of the present invention. In this case, the information regarding reports can either be processed or displayed at Step 414. At this point, the operator can make a decision as to whether to either stop reports and return to the main menu, or to otherwise continue at Step 416. If the operator elects to continue, the operator can then select a particular report to run at Step 418.

Some of those reports which can be generated include daily reports 420 or patient reports 422, or dose tracking reports 424. In the daily reports 420, either a true daily report 426 or a spanned report, that is, over a period of days 428, can be generated. The daily report identifies a single day report, whereas the spanned reports identifies a plurality of days. Patient status information is determined under the step of patient reports 422, such that the status of the number of patients can be displayed or entered at Step 430. The patient information can either be displayed or entered at Step 432, and patient look-up information, that is, all tests performed on that patient, can be performed at Step 434.

With regard to dose tracking reports 424, it is possible to either introduce or display test or process dose shipments at Step 426, the type of tests performed at Step 436, the type of tests performed at Step 438, the container return reports, a complete disposal report at Step 442, and a residual inventory report at Step 444. At this point, the algorithm allows for return at Step 446 to the subroutine 122.

It is also possible to generate lab reports 448, as well as additional reports 450. The selection of lab reports at Step 448 also carries a number of sub-steps, and which all either display information or allow for input of information, or both. This includes the DC accuracy at 450, sealed source inventory at Step 452, area monitoring at Step 454, and DC constancy at Step 456. In these cases, and as indicated, information can be introduced, processed or displayed.

The step of lab reports 448 also provides for a step of check-in meter information 451, that is, the information relating to a wipe monitor 460, information relating to a linearity sleeve method 462, and information relating to a linearity manual method 464, and to geometry 466.

The term "geometry" refers to geometric variations which may exist in the amount of radiation in a particular container. As an example, if a container had 100 cc of a radioactive material, it may provide an initial radiation measurement of 9.9 millicuries. If one diluted that amount with pure water to 200 milliliters, the radiation should still be 9.9 millicuries.

However, it has been found in practice that there can actually be some deviation. It is important, however, to obtain consistent readings and the "geometry" will allow for testing to determine that deviation, and perhaps a standard deviation which may exist in dilutions.

The additional reports generally include such reports which may be useful for the management of the organization using the algorithm, and includes a cost report 468, a referral source 470, and formula information 472.

The disposal of radioactive material in subroutine 124 is more fully illustrated in FIG. 11 of the drawings, and starts with actuation of the select disposal Step 474. The term "select disposal" for Step 474, actually refers to the type of disposal which will take place. Disposal is used in a broad sense to include actual discarding, sealing in a container for delivery to a location which is capable of handling radioactive waste, return to the source of the radioactive pharmaceutical or the like. In each case, tracking of the disposal must take place.

A decision is made by the operator at Step 476 to either return to the main loop or to proceed. At this point, it is possible to introduce the date, time and initials of the operator to obtain a display of available inventory 480, or otherwise, to select a particular container 482. When information about a container is selected, various choices are available, including information about whether or not to return to the manufacturer at Step 484, and then to update the container and, for that matter, the items contained in that container at Step 486. It is also possible to measure, or otherwise, process information for a decay in storage, at Step 488, and thereafter to update the container, and the items contained in that container, at Step 490. There is also a step referred to as "medical garbage" 492, and which allows for an update of containers and items which may be held in the container at Step 494. This routine provides for selecting any of a variety of operations to perform at Step 496.

After the operation to perform is selected at Step 496, the various operations which are available are shown and include an "add to container" step, which provides for either adding additional material or radioactivity to a container of a radioactive pharmaceutical. There is also an "add selected inventory" Step 500, or for that matter, a "remove selected inventory" Step 502. Further, there is a print container and content Step 504, which allows for printing of information for the container and the contents thereof. Preferably, the printing would occur in the form of printing a label.

The subroutine 124 also allows for showing of closed containers at Step 506, and the showing of open containers at Step 508. With closed containers, it is possible to remove or add the container back to the inventory at Step 510, and to also show or add the open container back to the inventory at Step 512. An additional Step 514 enables the selection of the particular container to be either added to or removed from the inventory. Moreover, it is possible to then perform the selected operation at Step 516. When there is a decision to either add or remove a container at Step 514, the container is surveyed at Step 518, identified as "place holder", and from there this information is introduced into the update Step 494.

The select dose calculator routine 128 is more fully illustrated in FIG. 12, and refers to those steps involved in the calculation of a particular dose to be administered to a patient. In this case, the operator can start with the step of the select dose calculator, namely, Step 520. As in the previous routines, the operator makes a decision at Step 522 as to whether to return to the main menu or to proceed. If the operator elects to proceed, the operator will activate the calculator tab at Step 524 and thereby enable selection of the particular radioactive pharmaceutical, information such as the weight of the patient, and like information.

In the example as illustrated, the operator can select, for example, a heart accelerator, such as adenosine for six minutes at Step 526, or adenosine for five minutes at Step 528. There is also a pediatric radioactive pharmaceutical 530. Each of these steps allow for entry of the weight of the patient at Steps 532, 534 and 536, respectively. Moreover, the selection could be for dipyridamole, namely, a heart accelerator, at Step 538 and for introduction of the weight of that patient 540. In each case, after the weight of the patient is introduced, it is then possible to determine if that input is valid at step 544. If the weight is not valid, a displayed error message will be presented. If the weight is valid, then the calculation routine will allow for calculation of the amount of adenosine at Step 546, and the same holds true for adenosine for five minutes at Step 548, and the pediatric at Step 550, as well as the dipyridamole at Step 552.

In order to allow for proper operation of the entire algorithm, and although the routine is fairly simple, it is important to set the current date and time, as best shown in FIG. 13. In this case, there is a routine for setting that date and time, and the operator would select the date/time operation at Step 554. A decision is made by the operator to either set the date or the time, or both, at Step 556. If the operator elects not to set the date or time, a system date or time is entered at Step 558 and saved at Step 560. Otherwise, if a decision is made to set the date or time at Step 562, the step will allow for setting the program date and the program time, the list of the patient and the list of the current tasks. Thereafter, a return to the main loop is provided at Step 564.

In order to print a schedule, as for example, a schedule for the following day, the following week, etc., a routine 566 is provided. The operator will then make a decision at Step 568 as to whether appointments are listed for that day. Inasmuch as the scheduling of patients and the scheduling of acquisition of radioactive pharmaceuticals is a critical part of the process for which the algorithm has been designed, a separate print schedule 566 can be generated, as best shown in FIG. 14. This print schedule 556 is not shown in the original main loop of FIG. 2, inasmuch as it is not one of the functions normally performed. However, it does allow for an operator to examine the schedule to acquire necessary information constantly. The print schedule 566 provides for a decision block to determine whether or not appointments for that particular day exist, at 568. If the operator desires to view such current appointments, the algorithm will create a schedule report, including current appointments. This report will include, for example, office information, that is, name, address and identification number, as well as appointment information, that is, time, name, test and phone of the patient. This information is shown in Step 570.

If the operator elects not to view the appointments for that day, there will be display of an error message to the effect that there are no appointments to present at Step 572. However, assuming that the operator has elected to obtain that information at Step 570, that information is displayed on a screen at Step 574. The operator can also make a decision at Step 576 to determine whether or not to print that schedule, and by sending that information to a printer at Step 578. Thereafter, the algorithm returns to the scheduling of the patient at Step 580. Following the desirability of a scheduling of patients, there are several subroutines for dealing with evaluation and measurement, as well as accuracy determinations. All of these subroutines are necessary when dealing with a radioactive material.

The first of these evaluations is a meter validation 582. The first of these meter validations is that of a survey meter validation. The operator is also provided with a decision step 584 to determine whether or not to proceed with validation or not to proceed. If the operator decides to obtain such a meter validation, the algorithm will proceed to Step 586 to obtain the meter data. Such data will include the initials of the operator, the time and date of the validation, a probe calibration date, a battery pass or fail test, a source name, a serial number, and MR/HR current reading. Obviously, other data could be included or some of this data could be eliminated, as may be desired. After all of this data has been presented to the operator at Step 586, the operator can then accept or not accept the survey at Step 588. If the operator accepts the survey at Step 588, a Step 590 automatically occurs to save that survey in the database.

FIG. 15B provides for a wipe meter validation, as opposed to a survey meter validation, and is essentially the same as FIG. 15A, with the exception that it deals with a wipe meter as opposed to a survey meter. The survey meter validation is shown in FIG. 15A. Consequently, the steps in connection with validation of the wipe meter in FIG. 15B are the same as those steps in FIG. 15A. Again, it is to be understood that the term "wipe meter" and the term "survey meter" do not refer to a particular meter per se, but rather, to the type of monitoring activity which takes place.

"Daily constancy" is a term used to refer to the consistency in the amount of radioactivity in a particular dose of a selected radioactive pharmaceutical. Thus, for example, patients may be administered the same dosage of the same radioactive pharmaceutical on different days. It is quite important to insure that the measure of the radioactivity on one day is essentially consistent with the amount of radioactivity on another day. In addition, it is important to insure that the radioactivity of one pharmaceutical is correlated directly to the radioactivity of another pharmaceutical. Thus, it is also equally important to insure that any calibrator used to measure this constancy is consistent.

The algorithm thereby provides for a daily constancy determination at Step 592 in FIG. 16. The operator similarly has a choice to determine whether or not to examine the daily constancy, or to avoid such examination at Step 594. If there is essentially no decision to examine the daily constancy at Step 594, the algorithm automatically causes a return to the hot labs Routine 120. However, proceeding with a daily constancy allows for the operator to input both time and date and, potentially, the initials of the operator at Step 596. At that point, the operator then selects a calibrator in order to make such a determination at Step 598. If the constancy determination has already been performed for that selected calibrator, the algorithm will automatically alert the operator at Step 598. Thus, the operator then has a choice at Step 600 to determine if that calibration has already been performed. If it has been performed, there will be a display of an error message at Step 602, and which may provide a statement to the effect that the dose calibrator has been completed for that day, but that the operator can edit the information. If the calibration has not been performed, there will be several dose calibrator measurements at Step 604.

For purposes of describing the dose calibrator measurements, there is given an example of a measurement with cesium (Cs), copper (Cu), cobalt (Co), and barium (Ea). More specifically, for purposes of this example, a measurement is made for cesium-137 (Cs-137), cobalt-57 (Co-57) and barium (Ba-133). The measurements may be performed with technetium (Tc-99m). An example of a cesium-137 measurement is set forth below:

I-123 (uCi)/TI-201 (uCi)/Cs-137 (uCi)/Tc-99m (uCi)/Co-57 (uCi)

Xe-133 (uCi)/I-131 (uCi)/Ga-67 (uCi)/In-111 (uCi)/Other (uCi)

After the calibration has been determined at Step 604, the operator can then elect to accept the values determined at Step 606 or, otherwise, cancel such determination. If the operator elects to accept the values of Step 606, the operator can so indicate and the algorithm will automatically save the constancy to a database at Step 608.

Dose accuracy is determined at Routine 610 in FIG. 17 of the drawings. As indicated in connection with the main loop of FIG. 2, the doses may be ordered from an external source, or they may be prepared in the pharmaceutical laboratory. In either case, it is important to know about the accuracy of the pharmaceutical and the accuracy of the radioactivity contained in that pharmaceutical dose. This routine involves a determination of the accuracy of the equipment, and not the doses per se. In effect, this is a quality control test usually performed on a bi-annual basis. After the operator elects to perform a dose accuracy, the operator has an opportunity at Step 612 to either proceed or not to proceed. If the operator elects not to proceed, the present accuracy level, if known, is maintained and the algorithm will return to the hot labs Routine 120 at Step 614. If the operator does proceed with the dose accuracy, the operator can introduce identification information, such as the operator's initials, the time and date at Step 616. The operator will then select a particular calibrator at Step 618.

If the calibration at Step 618 has already been performed, the algorithm will generate that information, such that a decision is made at Step 620. If the calibration has been performed, an error message will be displayed at Step 623. A message to the effect that, "the dose accuracy has been finished for the day and you may edit it only." However, if there has been no calibration for that day, the algorithm will cause the routine to move to Step 622 for a first source. In this case, the first source provides information for the first assayed amount, the second assayed amount, and the third assayed amount. If the operator does not elect to determine the accuracy of a second source, the algorithm will provide for an acceptance of the values at Step 624, and will thereupon either save the accuracy values to the database at Step 626, or return to the hot labs at Step 614.

The dose accuracy routine also allows for determinations of assays with second and third sources. These sources may be different radioactive test compositions, or otherwise, different radioactive test compositions. The second source similarly provides for a first assayed amount, a second assayed amount, and a third assayed amount source at Step 628. The algorithm can then allow the operator to determine if there will be an accuracy determination of yet a third source at Step 630. If there is to be a determination of a third source, then the algorithm will proceed to Step 632, where there is, again, a first assayed amount, a second assayed amount, and a third assayed amount. This will also provide a constancy determination or measurement of consistency.

It should be understood that although the dose accuracy Routine 610 provides for either assay with first, second and third sources, it is also possible to provide for an accuracy determination with yet a fourth source, a fifth source, etc. Those determinations would be performed in essentially the same manner as the first, second and third source determinations were made. The algorithm would merely be expanded accordingly.

FIG. 18 illustrates the routine for a linearity sleeve calibration 634. In effect, a sample can be placed in a suitable container, such as a vial, and inserted into a sleeve, such as a cylindrical open ended sleeve, and preferably, a lead sleeve. In effect, in the linearity sleeve calibration method, there is a simulation of time so that one can determine the logarithmic decay of an isotope in the radioactive pharmaceutical, over a period of time. The decay of this isotope is effectively compared with a known decay value for the same isotope. The sleeve linearity method is effective, in that it substantially reduces the amount of time which would be required for measurement of a normal decay, in absence thereof.

The operator can determine whether or not to proceed with a linearity sleeve calibration routine at Step 636. If there is no election to make a linearity sleeve calibration, the algorithm will automatically return to the hot labs Routine 120. In addition, it will cause a selection of any previous values that may have been determined. If the operator elects to proceed at Step 636 with the linearity sleeve method, the operator will cause an identification at Step 638, including for example, the operator's initials, the time and date. Thereafter, a particular calibrator is selected at Step 640. At that point, a determination will be made as to whether or not this calibration has been performed at Step 642. If the calibration has been performed an error message will be provided at Step 644, with the display of a message to the effect that calibration has already been performed.

If the calibration has not been performed, the operator then selects the sleeves for calibration at Step 646. This may be operated in conjunction with prompts from a display screen, advising of which sleeves have or have not been calibrated. Thereafter, fill calibration factors are introduced at Step 648. These fill calibration factors present all of the information necessary about the sleeve, and shows any percent deviation from the normal. Calibrations may be conducted, for example, with the following color combinations: black/black; red/black+orange; black+yellow/black; green/black; and blue/black+purple.

Thereafter, the select source can be displayed at Step 650. In this case, there will be a display of the amount of the isotope which is generating the radioactivity in any particular pharmaceutical. Measured values of the input assayed activity is then conducted at Step 652. The same color combinations that were used for the fill calibration factors in Step 648 are also used. In this case, one takes the black and disposes a red sleeve over that, then an orange sleeve, and in each case, calculates the percent deviation and the correction value therefor. Finally, it is then possible to calculate program values for each calibration factor at Step 654. The assayed time with respect to the decay corrected value, and the assayed percent of deviation, is also determined. At this point, the operator can determine whether or not to accept the values which are then determined at Step 656. If the operator accepts those values it will be transferred to the database at Step 658.

Linearity may also be determined by the manual method Routine 670, in FIG. 19 of the drawings. In this case, the same type of information which is obtained in the linearity sleeve method is also determined in the linearity manual method, except that in this case, the linearity and the various calibrations are determined manually. Thus, the operator can determine whether to proceed with the manual linearity method at Step 672. If the operator does so elect to stop this method, then the algorithm will automatically return to the hot lab Routine 120.

If there is a linearity determination by the manual method, then the identification information is taken at Step 674 which, again, includes the initials of the operator, the time and the date. Thereafter, a calibrator is selected at Step 676. Again, another decision is made at Step 678 as to whether or not this calibration has already been made. If the calibration has been made a display or a message will be presented at Step 680, with a message to the effect that the method cannot be performed twice on the same day. If this routine has not been performed, on that date, then there will be a selection of the source for this method at Step 682. From there, the fill calibration information can then be introduced. In this case, the calibration date, the calibration time and the calibration activity can be input or presented at Step 684. The values of the input assayed activity can then be input at Step 686. Again, a decision is made at Step 688 to either save these values or, otherwise, to discard them. If these manual values are saved, they are then stored at Step 690. The hours, time, date, the assayed activity base hours, the predicted activity, and the percent deviation can then be displayed or input.

At this point, after all input values have been saved, it is possible print a plot of this information at Step 692. The manual values from this method can also be saved at Step 694. After the values from the linearity manual method have been saved at Step 694, it is possible to then terminate the linearity manual method of calibration. Further, it is also possible to return to the hot labs routine previously described.

As indicated previously, the term "geometry" refers to that determination as to whether or not the calibrators themselves are making accurate measurements of radioactivity. Thus, and as indicated previously, if a source indicates a specific number of millicuries of radiation, that source should provide the same reading if it is diluted with a non-radioactive substance. Determination of this geometry, which is really a geometric variation, is set forth in FIG. 20 of the drawings. In this case, there is a subroutine for geometry at Step 696 which may, again, be referred to as a geometric variation. Again, the operator can make a decision at Step 698, as to whether to proceed or terminate this routine. If there is a termination, the algorithm will return to the hot labs routine at Step 698. If there is a determination by the operator to proceed with this geometric variation examination, the operator will introduce his initials, time and date, at Step 700. A particular calibrator, such as the dose calibrator, is selected at Step 710. A determination is then made as to whether or not this calibration has been made at Step 712. If this calibration has been made, a display error message will show at Step 714. In effect, this display error message may read "the dose calibrator geometry has already been performed for this day."

If there was no calibration performed for a particular day, the algorithm will then identify a selected source to be evaluated at Step 716. This source may be a syringe or a vial, or other element which is going to be evaluated. Thereafter, fill calibration information is provided at Step 718. This information may include calibration date, the calibration time and the calibration activity. Thereafter, the assayed activity is then measured at Step 720. This would include the input assayed activity and the measured values, as for example, volume with respect to time and with respect to assayed activity.

The Routine 696 also allows for the algorithm to calculate certain measurements at Step 722, as for example, a decay correction value, the correction factor and normalization activity. This can be performed on multiple occasions. Thereafter, the values which were calculated at Step 722 are then saved at Step 724. Further, the geometry values or geometric variation values are saved in the database at Step 726. At this point, the operator can close this routine at Step 728, and either return to this routine again, or return to the hot labs Routine 698.

A physicians information subroutine 300 is more fully illustrated in FIG. 21 of the drawings. This is essentially the same subroutine, which is identified in FIG. 8A of the drawings. This particular routine allows for display of information about any one or more physicians, the identifications of which are already introduced into the database. This subroutine also allows for introduction of information about a physician, who may not have been introduced previously into the database, to be presently introduced.

The subroutine 300 involves the determination as to whether or not to proceed at Step 730. If there is determination not to proceed with physician information, the operator can make that decision and return to the software administrator at Step 732. Otherwise, the operator would proceed to Step 734, in which all physician information is listed. This may be a listing of any selected physician, the identification of which has previously been introduced into the software and include, for example, the name and identification number, or the introduction of a new physician thereto. Thereafter, the routine allows for selection of a physician at Step 736, and the selection of an operation to be performed at Step 738. When the select operation is initiated, there is a possibility of introducing data about a new physician not previously introduced into the system at Step 740. There is also a possibility of editing information about physicians at Step 742, as for example, changing the name or identification number of that physician. Step 744 allows for deletion of that physician, and Step 746 allows for no selection of any one physician.

If a new physician is to be introduced into the system, the operator will introduce information at Step 748. This would include, for example, the name and identification number. In like manner, if the information about a physician is to be edited, that information will be edited by the operator at Step 750. This information from Steps 748 and 750 is then saved, if desired, at Step 752. The values of this information is then added to the database at Step 754.

If there is a decision to delete the physician, in order to insure that there is no error in this election, the operator, again, is provided with a decision Step 756 and if the operator does not wish to confirm the deletion of that physician, the routine will return to the beginning. If the operator elects to confirm that deletion, that information will be deleted at Step 758.

FIG. 22 illustrates the insurance information subroutine 302, which also shows in FIG. 8A of the drawings. In this case, reference numerals, which have been used to identify physician information in FIG. 21, will be used in FIG. 22 to identify like activities. However, it should be understood in connection with FIG. 22, that the activities set forth are applicable to insurance and not physician information. However, since the activities are essentially the same, the reference numbers for those activities in FIG. 21 are employed in FIG. 22.

With regard to insurance information, as opposed to physician information, the name of the insurer, the street address, city, state and zip code, possibly phone number, the principal contact at that organization, title, etc., may be introduced. Again, this subroutine provides for an introduction of new insurance, editing of the insurance, deleting the insurance, or no operation. Again, if insurance information is introduced, it would include the same information, such as the name of the insurer, the street address, the city, state and zip code, phone numbers, etc. The same would hold true if the insurance information was modified, or if the insurance information was deleted.

The scheduler subroutine 304 is more fully illustrated in FIG. 23 of the drawings. Here again, the same reference numerals which have been used in connection with physician information in FIG. 21, will be used in FIG. 23 for like activities. As indicated, essentially the same activities occurred in connection with FIG. 22 for the insurance information subroutine 302.

The scheduler information is that information relating to the individual who schedules the treatment of the patients and the ordering of supplies, and like information. In this case, the name and identification of the scheduler would be used in place of the physician in the subroutine 300 of FIG. 21. Beyond this, all of the activities, and the steps identified thereby, are essentially the same.

The room information subroutine 306 is more fully shown in FIG. 24 of the drawings. Again, the activities performed with respect to the room information is essentially the same as that set forth in physician information Routine 300, FIG. 21. Hence, again, like reference numerals identifying the same activity in FIG. 21 will be used in FIG. 24. The room information is essentially self explanatory, and identifies the particular room in which either an operation will occur, that is, in effect, the room in which the patient will be located for these particular activities. The dose information subroutine 314 is more fully illustrated in FIG. 25 of the drawings. Again, the term "dose" information is self explanatory, in that it provides for the doses of a selected product, and particularly, a radioactive pharmaceutical product, which is to be administered to a patient. Also, since the activities are the same as those for physician information in FIG. 21, the same reference numerals used in FIG. 21 will also be used in FIG. 25. However, with regard to entry of dose information and the modification of dose information, a product description would be entered. In addition, the half life, possibly in terms of hours, the shelf life, possibly in terms of hours, and the cost information may also be identified in Steps 748 and 750 of FIG. 25. Again, the dose values, which are saved to the database at Step 754 in FIG. 25, would include the product description, the half life, the shelf life, and potentially, the cost.

There is also provided a source information subroutine 760, more fully illustrated in FIG. 26 of the drawings. In this case, a user can inquire from the database about source information, such as activity level calibration data and the like. Thus, activity levels could be listed, and for that matter, de-listed, since they are primarily used for instrument calibration information. As indicated previously, a constancy quality control examination may be made, and in this case, information can be introduced into the database. This information is, however, for purposes of insuring a daily constancy.

Again, it is to be noted that the activities performed in the sources information are essentially the same activities performed in the physician information subroutine 300 and, again, like reference numerals employed in FIG. 21 will also be employed in this FIG. 26. The sources disposal subroutine 312 is more fully illustrated in FIG. 27 of the drawings. This subroutine starts with a decision by the operator at Step 762, to determine whether or not to proceed with this subroutine, or return to the software administrator at Step 764. If there is an election to proceed, the operator will set the date and the operator's initials at Step 766, in order to identify that operator.

The source disposal subroutine provides information about the sources of items included in the database, and particularly, radioactive items and the location of those items. In particular, the source disposal subroutine 312, is concerned with elimination of all finished radioactive instrumentalities and radioactive materials. This subroutine provides that necessary record keeping information as to what happened to the particular instrumentality or pharmaceutical involved. In this case, all available inventory, that is, all available source materials, are identified at Step 768. This would include the calibration time, calibration date, and calibration activity. Thereafter, the operator can observe and potentially select the particular disposal option at Step 770. The operator can elect to provide for return to the manufacturer at Step 772, provide for decay and storage at Step 774, deliver the medical garbage at Step 776, or to restore at Step 778.

Alter selection of a particular disposal option, each one of the selection decisions would move to Step 780, in which there is a list of all inventory for this particular selection disposal option. This would include, for example, the calibration time, calibration date, calibration activity, and like items. In effect, all inventory in the decay Step 774 would be shown. Thereafter, the operator can select the item to be treated in Step 782. In essence, there will be a selection of the particular source and what to do with that source. In other words, is there an election to move the source to the disposal option. If there is such a decision in Step 782, the operation itself is performed at Step 784. Thereafter, the algorithm will allow for return to Step 786 for no operation.

The editing of inventory subroutine 316 is more fully illustrated in FIG. 28 of the drawings. In this case, the operator will elect to either quit this routine at Step 790 and return to the software administrator at Step 792. Otherwise, election to proceed will provide for the operator to set the date range involved, that is, from a given date to a given date, at Step 794. In this case, the operator can elect to either show the inventory or not show the inventory at Step 796. If the operator proceeds to show all of the inventory, that inventory will be listed at Step 798 for that specific date range, identified at Step 794.

Inventory information may include, for example, a description of the inventory, a calibration of the activity, the calibration date, the calibration time, the delivery number, expiration date, expiration time, the date received and the time received, the receiver's initials, the volumetric units, and like information. After all this information has been displayed for the selected inventory in that selected date range, a decision is made as to whether or not to edit that information at Step 800. If that information is to be edited, again, the initials of the operator, the date and time, the description of the product, the volume in units, the calibration date, the calibration activity, the expiration date and expiration time can all be edited, or any portion thereof can be edited, at Step 802. Thereafter, a decision is made to either save the inventory information at Step 804, or to delete that inventory information at Step 806. If there is a decision to save the inventory information, that value is saved at the database in Step 808, and if there is a decision to delete this information, it is deleted from the inventory database at Step 810.

Patient dose information can be edited in subroutine 318, as more fully illustrated in FIG. 29 of the drawings. In this case, the patient dose information allows for the operator to make a decision at Step 812, to either quit the editing subroutine and return to the software administrator at Step 814, or otherwise, to proceed. If the operator proceeds, the date range is set at Step 816. This information would include, for example, the dose information for a particular patient from a given date to a given date.

Thereafter, the subroutine 318 provides for an operator to determine whether or not to show the patient doses at Step 820. If there is a decision not to show the patient dosage, then the algorithm will return to the beginning of the patient dose information. Otherwise, the algorithm will then provide for listing all patient dose information at Step 822. In this case, the schedule, the dosage activity, the dosage activity units involved, the date injected, the time injected, and the operator's initials, are all either input or displayed at Step 822.

Following the information in Step 822, the operator can decide whether or not to edit the item in Step 824. In this case, any particular item illustrated in Step 822, can be edited. Again, the edit information would include the initials of the operator, the date, the name of the prescription involved, the prescription number, the dosed activity, the dosed activity units, the residual product amount at Step 826. After the information has been edited, the algorithm allows the operator to either save this information at Step 828, or to delete this information at Step 830. If there is a decision to delete the information, the algorithm will return to the beginning of this subroutine at Step 818. Otherwise, the values of these doses can be deleted from the patient dose database at Step 832. If there is an election to save this information, the information will be saved in the database at Step 834.

FIG. 30 illustrates the task information subroutine 322. Those steps involved in the task information are essentially identical to the steps involved in the physician information subroutine 300 in FIG. 21. Here again, like reference numerals will be used to represent like activities. However, it should be recognized that some of the information which may be presented or, otherwise, input may be different, although the activities are essentially the same as presented in FIG. 21.

Referring to the task information in FIG. 30, the subroutine is essentially the same as for the physician information subroutine 31, and essentially parallels that subroutine. However, in this case, the task information includes the name, description and type of task involved, the days of the week involved, the month, day and year, and whether or not this is a quarterly information selection. The select task operation at Step 736 may constitute, for example, a monitoring of a selected area or a monitoring of a selected instrumentality. The select operations Step 738, in this case, would constitute those groups of items which are to be monitored.

One of the important aspects of task information is the fact that it operates as a type of reminder program, which is linked directly to the process performed by the algorithm. This task information routine will prompt the user to do several functions. As an example, this routine will cause the user to do daily constancy examinations and daily backup examinations.

Another one of the important aspects of task information is the fact that the user literally has the ability to introduce those tasks which the user desires to perform for that particular organization. Thus, as a simple example, when a task is presented, the operator can merely examine that particular task and by using the cursor to move to that particular function, or to go directly to that function if the computer is equipped with a touch operated screen. Thus, it can be seen that task information is effective both as a reminder, and which also allows an organization to easily insert the tasks which it would like to have performed on a periodic routine.

Task information at Step 748 would provide for the entry of the name of the party, the description and type of information, the days, month and year. That same information would be provided if there was an election to modify the task information. Finally, that same information would occur when deleting that information at Step 758, or saving that information to the database at Step 754 of FIG. 30.

FIG. 31 illustrates the test information subroutine 322 in more detail. In this case, the test information subroutine closely parallels the physician information subroutine 300, as shown in FIG. 21. Consequently, those like reference numerals used in FIG. 21 are also used in FIG. 31.

Inasmuch as the activities in test information 322 are the same as activities in the physician information subroutine 300, the activities will not be again described. However, the information which is introduced or which is generated is different than in FIG. 21, and relates to those tests which have been conducted.

Particularly, these tests are designed to provide information about the radioactivity of certain radioactive pharmaceutical products which are to be administered. However, these tests could also be used for measuring instrumentalities and the like.

In effect, the term "test information" really refers to tasks which have to be performed with regard to a patient. Task information in the previous routine referred to those activities which had to be performed, but not necessarily, with respect to a particular patient. Test information, however, deals only with patients.

In Step 734 of FIG. 31, in place of physician information, the test information is introduced and includes, for example, the name and description of the product, the identification of that product, such as an identification number, the absolute units of the product. There is also a determination of whether or not such test is applicable to this product. The same information is provided at Step 748 and step 750, as well as Steps 754 and 758, in FIG. 31 of the drawings.

It is to be noted, that the selection of a test to be performed, such as the selection of a physician in Step 736 in FIG. 21, is not used. Such information is not required for test information. However, after the operation 738 is selected, the subroutine proceeds in essentially the same manner as the subroutine 300 for physician information in FIG. 21.

FIG. 32 shows the study information subroutine 326 in more detail. This subroutine has many of the steps in common with test information. In this case, the operator can make a decision at Step 836 as to whether to return to the software administrator at Step 838 or to list the available studies to be performed at Step 840. After all of the available studies at test 840 have been either input or displayed, the subroutine proceeds to Step 842 where a listing of all such study information is provided. Specifically, the name and description of the study is identified at Step 842. From this, the operator may select a particular study at Step 844. Thereafter, the study information for that particular study is identified at Step 846. This information would include the study tests involved, the hours and the minutes involved, and the name of the test and the description of the test, or other information, if desired. It is possible to select a particular operation at Step 848, if desired. However, this step could be deleted, if desired.

Study information is closely related to test information, in that it involves information which has been obtained with respect to patients. Typically, study information involves the grouping of tests into individual blocks. Thus, if a patient had a plurality of similar tests, and one wished to examine the history of the results of those tests with that particular patient, the study routine would allow an automatic gathering of the tests for that particular patient, and which would thereby allow examination of the tests for that patient. In like manner, it is possible to examine tests performed only with one particular radioactive pharmaceutical used on that patient, and also another study for examining the results of administration of a different radioactive pharmaceutical for that same patient.

After selection of the operation, a decision is made as to perform a new study at Step 850, edit a selected study at Step 852, delete a study at Step 854, or perform no operation at Step 856. If no operation is performed, the subroutine returns to the beginning of the study information.

If a new study is selected at Step 850, it will be necessary to identify the name and description of the study, whether to add or remove the study, the test names and the test descriptions involved. That same information would apply at Step 858. If there was a decision to edit the study at Step 852, then modify study information is introduced at Step 860. This is the same information which would be entered into the enter study information Step 858.

If there is a decision to delete the test, the operator is then queried as to whether or not he or she confirms a deletion of that test at Step 862. If so, the information is deleted at Step 864. If the information is to be saved at Step 866, that information is then saved and introduced into the database at Step 868.

The meter probes subroutine 330 is more fully illustrated in FIG. 33 of the drawings. In this case, the steps performed are the same steps as those used in the physician information subroutine of FIG. 21. Consequently, the same activities provided in FIG. 21 will carry the same reference numerals in FIG. 33. The primary difference is that in place of physician information, information regarding meter probes is provided.

In connection with the performance of the algorithm, probes are used with each of the meters that are tested. Moreover, probe information would relate to the name, the description of the probe, the model number, potentially the manufacturer, and the serial number. Different probes may be used with the various meters and it is important to insure that each probe provides the same information. Inasmuch as there could be a difference between results from the different probes with the same meter, the probes are specifically identified and tested, in accordance with the subroutine 330.

FIG. 34 illustrates the subroutine meter analysis 332, identified in FIG. 8A of the drawings. In this case, meter information, such as the survey meter information, can be displayed on the screen of a monitor for the user. The algorithm in this case is very similar to the algorithm for FIG. 33 and, therefore, like reference numerals will be used. In this case, the meter analysis shows that for the survey meter. However, and although there is no particular subroutine shown for a wipe meter analysis, that analysis would be essentially the same as shown in FIG. 34.

The flow of the algorithm is almost identical to that of FIG. 33. Even the information which is generated and introduced is similar. In the case of the survey meter, Step 34 would carry the name and description of the meter, the model number, the manufacturer's serial number, the calibration date, the name of the operator, and the probe number. Similar information would be introduced at the enter survey meter information Step 748, modify the meter information at Step 750, delete that information at Step 758, and save the information at Step 754.

With regard to a subroutine for the wipe meter, and although not illustrated, the information sought or introduced is almost identical. However, with regard to the wipe meter, there may be information regarding the percent of efficiency of the probe used therewith.

FIG. 35 illustrates that Routine 335 for monitor of items. Again, the routine is identical to that shown for meter probes in FIG. 33 and, therefore, the entire routine is not described herein. However, with regard to the items which are monitored, these items are essentially non-patient items. In particular, they are the areas or items which have come into contact with the radiation. Tables, counter tops, syringes, probes and the like, thus, fall into this category. Some of the information which may be introduced or displayed is that dealing with the name of the item, the description of the item and, particularly, a "trigger value". This is essentially the value in which the amount of radiation exceeds a predetermined level. This is important to know so that the individual handling the items which may be radioactive is not overexposed.

FIGS. 36A and 36B deal with the monitor of groups of items, and is that Routine 340 identified in FIG. 8. In this case, the monitor group will refer to certain items which have been grouped together for purposes of analyzing those items, or of determining other information relating to those items. Thus, and for example, if certain items were included in a room identified as A, those items may constitute one group, and the items in another room identified as B would constitute the items for that group, and so forth.

It is also possible to group items by the types of items. For example, all probes can be analyzed, all meters can be analyzed, etc. This type of information can be effective in determining, for example, if one technician was not performing his or her tasks properly, or otherwise, inefficiently. Thus, the ability to allow examination of these items by groups can be quite advantageous.

The Routine 340 also includes that decision making Step 870, which allows for an operator to either decide to quit the routine and return to the software administrator at Step 872, or to proceed. If the operator proceeds, information regarding the lifting of all available groups can be displayed at Step 874. In this case, for example, the name of a particular group and the description can be identified. In the case of meters, there may be a naming and description of the meters involved in that particular group. Assuming that meters were to be monitored, the operator then selects a particular operation to be performed at Step 876. Thereafter, all of the available monitor groups are identified at Step 878. This would include the name and description of the meter, as well as the particular meter or meters involved.

The operator can then decide to either introduce a new monitor group at Step 880, to edit the monitor group at Step 882, or to delete the monitor group at Step 884. There is also a Step 886 which allows the operator to edit the group results. Thus, for example, if one item got included by mistake, the operator could eliminate that item at Step 886, or otherwise, to correct information which may have been erroneously introduced.

If there is an election to monitor a new group, then the algorithm will proceed to Step 888 which allows for the operator to enter the name and description, and in this example, the meter numbers of the meters involved. The same holds true if there is to be an editing of the monitor group at Step 882. In this case, the Step 890 will allow for modification of the information. Finally, with regard to deletion of the monitor group at Step 884, there is provided a decision for the operator at Step 892 to either confirm the deletion of that information or not confirm that deletion. If there is a decision to continue with a deletion of the information, that information is deleted at Step 894.

If there is a decision to enter monitor group information, such as new monitor group information, or to either modify that monitor group information, the operator can then decide at Step 896 whether or not to save the information. If the information is saved, then the routine will automatically return to the beginning of the monitor group Routine 340.

If there is an election to delete any information, as for example, at Step 894, the operator is also given the prerogative to delete certain monitor group information, and not all of the information at Step 894. The operator can then change the grouping of the items at Step 898. If there is a changing of the group items at Step 898, this routine will then allow a listing of all of the monitor group items which may be changed at Step 890. Thereafter, the operator can select the monitor group item to be modified or changed at Step 892. At this same step, the operator can add items to the group or delete items to the group. The operator can then create a new item at Step 894, add one or more items to a group at Step 896, remove an item from the group at Step 898, or to perform no operation at Step 900. If there is to be a creation of a new item, then that information can be introduced at Step 902. The operator can then decide whether or not to save that information at Step 904. If the operator elects to save that information, the values thereof will be stored in the database at Step 906. The algorithm will then allow return to a listing of all of the group monitor items at Step 890.

If the operator elects to edit the monitor group at Step 882, the algorithm allows for the operator to select a date for editing at Step 908, and with the results thereafter being displayed at Step 910. After this, the group results are modified at Step 912. The operator again makes a decision as to whether or not to save this modified result at Step 914, and if there is an election to save, then the values are stored at the database at Step 916. The algorithm then returns to Step 918 (see FIG. 36A), and hence, to the beginning of this Routine 340.

It should be recognized that it is possible to include that Routine 342 in essentially the same format as the monitor groups of FIGS. 36A and 36B. In essence, the steps would be the same, although information introduced or displayed might very slightly.

FIG. 37 illustrates that Routine 344 illustrated in FIG. 8A of the drawings dealing with dose calibrators. The dose calibrator constitutes a way of indirectly determining the amount of radiation which is introduced into a patient, by measuring the amount of millicuries which were injected into the patient. However, this particular examination is more specifically concerned with the calibrator per se. In this case, the information which is generated in this subroutine 344 is concerned with the actual calibrator per se, as opposed to the dosage which was injected into the patient.

The dose calibrator subroutine very closely parallels that routine dealing with task information in FIG. 30. Again, like reference numerals will be used to represent like steps appearing in FIG. 30. However, in Steps 734, 748, 750 and 758 of FIG. 37, the information listed for the dose calibrator would be the name and description of a calibrator, the model number, the manufacturer, and serial number. Again, some of this information could be deleted and other information could be added, if desired.

The dose calibrator constancy Step 346, identified as "DC constancy setup" in FIG. 8A, is more fully illustrated in FIG. 38 of the drawings. In this case, the constancy of the calibrator is measured. In other words, the calibrator should render the same reading day after day. The calibrator may be measured with a radioactive source such as, for example, cesium, which has a thirty year half life. Consequently, the radioactivity measured the calibrator does not change. However, if the calibrator is measured against the cesium and a different reading is obtained then, by definition, the problem lies with the calibrator.

The constancy Routine 346 allows the operator to either continue with this constancy calibration at Step 920, and if the operator elects to cease this constancy calibration, the routine will return to the software administrator at Step 922. If the operator elects to continue with this constancy evacuation, then the operator must identify himself or herself by their initials, and the date and time at Step 924. At this point, the operator then selects a particular calibrator for which to determine constancy at Step 926.

The operator then can determine if a calibration constancy determination has already been made at Step 928. As an example, the operator can determine if that calibrator was already evaluated for that particular day. If the calibration has already been performed, then the algorithm will generate a display to the effect that the display has already been performed for this meter at Step 930. The operator can then elect either to edit this routine at Step 932 and return to the software administrator or, otherwise, to continue with the calibration at Step 934. The calibration is essentially the same as that calibration performed in Step 604 of FIG. 16, dealing with the daily constancy. Consequently, the actual calibration steps are not described in any further detail herein. However, this routine at Step 346 does allow the operator to either accept the values determined at Step 936 and return to the software administrator at Step 922 or, otherwise, save the constancy as a default at Step 938 and also return to the software administrator Step 922.

The dose calibrator constancy edit Routine 358, as shown in FIG. 8A of the drawings, is more fully set forth in FIG. 39. In this case, the constancy edit allows for any change in the calibrator constancy determination. Moreover, the calibrator constancy edit essentially includes those same steps performed for the dose calibrator constancy determination at Step 346. Consequently, the dose calibrator constancy edit flowchart 358 of FIG. 39, is not described in detail. In effect, the same steps which took place in FIG. 38 also take place in the Routine 358 of FIG. 39. Consequently, like reference numerals are used. However, it is to be noted at Step 934 in FIG. 38, which deals with dose calibrator measurements, Step 934 in FIG. 93 allows for modification of those dose calibrator values.

FIG. 40 illustrates the details of a dose accuracy edit Routine 362, shown in FIG. 8A. In essence, this dose accuracy edit routine allows for a correction of the dose accuracy routine, which was shown and described in connection with FIG. 17 of the drawings. Thus, and in this case, the dose accuracy edit routine includes the same steps which were set forth in connection with dose accuracy measurement of FIG. 17 and are, therefore, given like reference numerals.

The edit input sleeves Routine 356, as shown in FIG. 8A of the drawings, is more fully set forth in FIG. 41. As indicated previously, the sleeves are typically formed of an effective radioactive insulative material, and a dose or an item can be inserted in the sleeve in order to measure decay on a rapid basis, which might otherwise take many hours, if not days, to measure. Inasmuch as each sleeve is different from one another, the radioactivity insulation characteristics are different. Consequently, it is necessary to know those characteristics of each individual sleeve, and to be able to calibrate these sleeves from time to time.

The routine for inputting sleeves is essentially identical to that Routine 322 for inserting and dealing with task information, as shown in FIG. 30. Consequently, and here again, like reference numerals will be used for like activities, as set forth in FIG. 30.

With regard to listing of sleeve information, the name, description, model number, manufacturer and serial number, for example, could be identified. In the select Step 736 of FIG. 41, a particular sleeve is selected. In each of Steps 740, 74 and 744, again, this routine is concerned with the inputting of sleeves. That same information introduced into Step 734 of FIG. 41 is also introduced into Steps 748, 750, 758 and 754 of FIG. 41. In this way, all of the sleeves which are used in any measurement activities are then incorporated in the system of the invention.

The step of sleeve calibration 360, included in the menu of FIG. 8A, is also more fully set forth in FIG. 42 of the drawings. The actual inputting of the linearity sleeves was more fully set forth in FIG. 18 of the drawings. This routine, therefore, closely follows the routine on FIG. 18. As a result, the same activities which occurred with regard to the introduction of the linear sleeves of FIG. 18, will use the same reference numerals in this FIG. 42, dealing with calibration. In effect, this calibration involves a determination of the calibration of the linear decay of the sleeves. In substance, Routine 360 of FIG. 42 closely parallels FIG. 18, in that this routine permits the calibration of the same sleeves which were introduced in the routine of FIG. 18. Consequently, like reference numerals used in FIG. 18 will also be used to represent like activities in FIG. 42.

It is to be noted that with regard to the fill calibration factors, when calibrating these sleeves, the same color combinations are used. Thus, where there was a fill calibration factor 648 dealing with black/black+red/black+orange and black+yellow/black+green/black+blue/black+purple, the same color patterns are used in FIG. 42. With regard to input assayed activity in the measured values, again, the same color combinations are used that were used in Step 652 of FIG. 18. Finally, the program values which were determined at Step 654 in FIG. 18 are also determined at Step 654 in FIG. 42.

The primary difference between the Routine 360 of FIG. 42 and that of FIG. 18, is the fact that Step 644 in FIG. 18 provided for a display error message. Rather, in Step 644 of FIG. 42, and edits the information regarding the editing of the sleeves is set forth.

The Routine 364 of FIG. 8A, dealing with the editing of the linear sleeves, is set forth in FIG. 43 of the drawings. In this case, the sleeves were introduced by the Routine 634, as set forth in FIG. 18 of the drawings. Inasmuch as the Routine 364 of FIG. 43 is merely designed to correct or eliminate information introduced with regard to introduction of the linear sleeves in FIG. 18, the routine closely parallels that of FIG. 18. Again, reference numerals used in connection with FIG. 18 will also be used for like activities in FIG. 43.

In substance, the editing of the linearity sleeves in FIG. 43 essentially repeats the actual operation of FIG. 18. In this case, there is merely an editing, as indicated. The one major distinction which exists between the editing in FIG. 43 and the inputting in FIG. 18, is the fact that in FIG. 43 there is no display error message Step 644. Beyond this, the routine is essentially identical. However, the other major distinction is the fact that in FIG. 43 after editing, the routine will allow for return to the software administrator, whereas in FIG. 18, the routine allowed for return to a hot labs.

The dose calibrator geometry subroutine 366, as shown in FIG. 8A, is more fully set forth in detail in FIG. 44 of the drawings. In this case, the dose calibrator geometry is a quality control procedure dealing with the accuracy of the equipment, and not with regard to accuracy of doses per se, of a radioactive pharmaceutical. In substance, this is actually a determination of constancy. In accordance with this procedure, a number of values are measured and the average of those values is taken, as a measure of decay.

When measuring a geometry, there is a determination, effectively, of geometric accuracy. Again, as an example, if a vial contains a radioactive substance of, e.g., 5 millicuries, and that vial is diluted ten fold, the amount of radioactivity should still read 5 millicuries. Nevertheless, in some cases, the same measurement is not obtained. Thus, a plurality of measurements are made, as for example, three measurements, and they should be at least within a specified percentage, e.g., 5% of an accuracy reading. In this way, theoretically, the same constancy will be obtained each day.

In accordance with the dose calibrator geometry routine of Step 366, as shown in FIG. 8A, the details of this subroutine are more fully set forth in FIG. 44 of the drawings. In this case, the operator can elect to either proceed or not proceed with a determination at Step 940. If there is a determination not to proceed with this geometric determination, then the subroutine will automatically return to the software administrator at Step 942. On the other hand, if there is an election to proceed, the algorithm will prompt the user to select a particular calibrator at Step 944. After the operator has selected a particular calibrator, the dates of previous determination of the calibrator geometry is set forth at Step 946. From that, the operator can then select a particular date in which a calibration was performed at Step 948.

At this point in the subroutine, the operator can select a particular option at Step 950 of either deleting the results at Step 952, viewing the results at Step 954, or performing no operation at Step 956. If the operator deletes the results at Step 952, there will be a confirmation asking the operator, again, if this information is to be deleted at Step 958. If there is a decision to delete that particular record at Step 960, the subroutine will return to the beginning of this subroutine 366. On the other hand, if the operator elects to view the results, the values thereof will be displayed on a display screen of a monitor at Step 962. In this case, some of the information which is to be displayed includes the volume, such as the milliliter volume, the assayed time with respect to the assayed activity, the decay correction, and a correction factor.

FIG. 45 shows in detail the routine for editing of manual linearity 368. Linearity, by the manual method 670, was more fully shown in FIG. 19 of the drawings. In this case, the subroutine linear manual 368 enables a modification of any information introduced in the subroutine 670. This subroutine provides for an operator to either abandon this subroutine at Step 964 and return to the hot labs routine at Step 960. Otherwise, the operator can elect to proceed and the algorithm calls for the operator to enter initials and time at Step 968. Thereafter, the operator selects a date at Step 970. The operator can then introduce a date range applicable for the fill calibrators at Step 972. From that, the operator can select a particular calibrator for evaluation at Step 974.

After a calibrator has been selected at Step 974, the linearity calibration information is then introduced at Step 976. This would include, for example, the source, the calibration date, the calibration time, calibration activity, and the base hours. In this case, the base hours refers to the amount of time for a decay in the amount of radioactivity over a given time period. In the manual method, there is an attempt to determine whether the decay of a source is linear over a given time period. This editing procedure allows for correction of any error. After calibration information is introduced, the fill linearity manual information can be introduced at Step 978. At this point, the operator can select the values involved or the measurement limits at Step 980. The manual information can be modified at Step 982. If there is an election to modify this information, it can be saved at Step 984 and where the values are then saved to the database at Step 986. If desired, the operator can elect to print a plot at Step 988.

A decay in storage subroutine 370 is more fully illustrated in FIGS. 46A and 462 of the drawings. In essence, this is a routine for tracking of and maintaining of an inventory of items in storage. The display presented by this subroutine allows for management of all of the radioactive items which are stored, and thereby provides for management on a long term basis. The decay in storage subroutine is a fairly important subroutine, in that it manages the need for retention of items which have been brought into contact with, and contain some degree of, radioactivity. These items typically cannot be discarded until such time as the radioactivity has completely decayed. In short, this subroutine provides information as to source of a radioactive item, how it was used and, essentially, what happened to that item after this was finished. In substance, there are essentially only two effective ways to deal with an item containing some radioactivity, and that is to either put the item back into a container and ship the item to the source from which it was received. The second technique is to put the item into a container and allow the radiation to decay in storage for its half life.

The items which are introduced into a container for storage so that they may decay, are recorded into the database and displayed on the screen of a monitor in this subroutine. The user can carefully select a particular container for storage of an item based on the half life or the decay of radiation in that item. In substance, the user would attempt to locate a container in which there is no item having a longer half life than the item to be introduced. As a simple example, one would not insert an item which has a half life of one day into a container in which the containing cesium having a half life of 300 years. In so doing, the items in that container would have to be maintained for the life of the longest decaying item, and in this example, that would be 300 years. Consequently, the user would attempt to find a container in which the other items in that container had a decay life of about one day.

The decay in storage subroutine allows for the operator to either continue with the subroutine or to abandon the subroutine at a decision Step 990. If there is a decision to stop this subroutine, it will automatically return to the software administrator at Step 992. If there is a decision to continue this subroutine, then the operator is prompted list the type of storage containers at Step 994. In this case, the operator will list the type of storage container and whether it has been opened. More specifically, the operator can identify the date the container was opened, the description and the status of the container, the operator's initials, and the date of disposal. The operator can also be prompted to list the current maximum activity, the container/survey results, wipe results, and the time the container was closed.

Following the type of storage container, it is then possible for the operator to select a particular container at Step 996. It is also possible for the operator to select a new container at Step 998. If the operator selects a particular container at Step 996, then in Step 1000 the operator can list any needed or desired information. As a simple example, the operator can introduce the product name, the current activity, the calibration date, the calibration time, the prescription number, the product type and an expiration date, if the item is a pharmaceutical. The operator can also introduce or cause to be generated initials of the recipient of this material, the date received, the time received, the radiation level, the condition of the container, the delivery number, the cold dose. Further, information such as a survey meter, background meter, surface meter, placement of packages, vendor status, residual activity, and last number disposal time. Thereafter, the operator can then select a particular operation at Step 1002. When selecting an operation, the operator can select containers at Step 1004, closing a container at Step 1006, opening of a container at Step 1008, leading a container at Step 1010, and editing a container at Step 1012. Furthermore, there is an option for the operator to print a container and the items contained therein at Step 1014. If there is no operation at Step 1016, the subroutine will automatically return to the beginning.

If there was an election to delete a container, there is a prompt and the operator must make a decision at Step 1018, and the operator then can either delete or not delete that container and items therein from the storage display at Step 1020. At that point, the subroutine can return to the dose management Routine 328 at Step 1022. If there was an election to provide for a new container, container information is then entered at Step 1024. This would include, for example, a description of the item, the date and the date it was opened. If there is a decision to edit a container at Step 1012, then the container information which is modified can be introduced at Step 1026. This may include, for example, the description, the date that the container was opened, the status, and the date the container was closed. If a new container or an edit container step is elected, the subroutine will automatically move to Step 1028, where the operator has the option of either saving the end information or discarding that information. If it is elected to save the information, the subroutine will proceed to Step 1030 in which case, again, the description, the date that it was opened, the status, and the date closed information is then presented.

If there was an election to open a container at Step 1008, that is, a container already in the inventory, a warning message would be presented to the operator to the effect, "are you certain that you want to return this container to inventory?" Finally, if there is a decision to close the container at Step 1006, information is presented as to any modification of that container. Thus, information may include such items as returning to the manufacturer, disposal at medical garbage, or another reason. The date and initials of the operator can then also be introduced at Step 1032.

If there is a decision to open a container or a decision to close a container, the operator is then given the option to either determine whether or not to save the status of that information at Step 1034. If there is an election to save that information, the information regarding modification of a container in that database is then presented at Step 1036, and from there the information is saved in the database at Step 1030. If there is no election to save the information, then the subroutine will automatically move to return to Step 1022 where this subroutine is can be started again or terminated.

The subroutine dose patient options 380 is shown in FIG. 47, and the schedule patient option 380, as shown in FIG. 48, are actually options which can be introduced into the algorithm. In essence, these are only two of the options which can be introduced into the algorithm. The dose patient option 380 in FIG. 47 also provides for the operator to either proceed, or quit this particular administration option at Step 1038. If there is an election to cease this option, the algorithm will return to the main loop at Step 1040. If there is an election to display this option, the subroutine proceeds to Step 1042. In this case, the options are displayed. As an example, in the dose patient option, the residual amount of the dose is displayed, and this may link to additional doses after injection. There may even be a note to remember the last test on the re-dose and the percent allowance on an injection. Other information could also be introduced. At this point, the operator can modify the options at Step 1044 and save the dose patient option to the registry at Step 1046.

The schedule patient options 384 in FIG. 48 has essentially the same steps as the dose patient options in FIG. 47. Consequently, and here again, the common reference numerals will be used to represent like activities. However, in the option of scheduling the patient, at Step 1042, the sex of the patient, the insurance information, the birth date, weight, street address, and like information may be introduced. In addition, information can be introduced regarding the last test made, the last scheduler who introduced information, diagnosis and like information can also be presented at Step 1042.

The subroutines of FIGS. 47 and 48 are identified as options, inasmuch as this information may be required by some states, but not by others. Consequently, the user has the option of either not dealing with this subroutine, or otherwise, to deal with the subroutine. In each of these options, it is possible for the user to turn on and off the entire field. In this way, the user does not even have to bother with those particular fields. For this matter, other options can equally be built into or removed from the algorithm.

An inter-date range Routine 1048, as shown in FIG. 49 of the drawings, is an effective subroutine in allowing information to be gathered in accordance with particular dates, such as starting and ending dates.

This routine is quite important in that it can allow for almost any type of information introduced with respect to this algorithm to be presented on a particular date range. Thus, for example, if the user of the algorithm desired to determine the quantity of a particular radioactive pharmaceutical order in a particular time period, that information could be easily and readily established by use of the date range and the particular pharmaceutical for which information was sought. If cost information were desired, that information could similarly be gathered for a particular date range.

The date range subroutine is quite important for preparation of governmental reports. Typically, various governmental agencies will require information for a given date range, as for example, a period of one month. Moreover, that month may not necessarily start at the beginning of the month, such as at the first of the month and end at the $30^{th}$ or $31^{st}$ of the month, but rather, could have intermediate starting and ending dates in between. This subroutine, therefor, is highly effective in allowing the gathering of that necessary information and generation of reports, as may be required.

The enter-date range subroutine 1048 is effective in that it can be easily and conveniently used by the operator to obtain information for a selected date range. Thus, if the operator was required to produce three reports, the operator could obtain the date range from this subroutine 1048, and then immediately generate a report for that desired date range. The operator could follow the same steps and obtain that same date range for another report.

In accordance with the routine of FIG. 49, after the operator elects to enter a date range at Step 1048, the routine will display that date range at Step 1050. Otherwise, the operator can enter a new date range at Step 1052. At this point, the operator then can either elect to close or open the date range window at Step 1054. If the operator elects to close that date range, that closes subroutine, the operator will then return to a reports routine at Step 1056. Otherwise, the operator can then make a decision for the date range for each selected report.

At Step 1058 the operator makes a decision to either void a start date at Step 1060 and allow all data from the beginning of time to be entered into the report or otherwise starts a new date with a "so called" filter Step 1062. The operator can perform the same decision of whether or not to enter a date range at Step 1064. Again, the operator can enter a no beginning date or no ending date, thereby acquiring all data for a particular report to a present date. This would occur at Step 1066. Otherwise, the operator can enter an end date at Step 1068. After Steps 1066 and 1068, the routine would automatically return to the calling program, that is, the data which is to be introduced in to that report with the starting and ending filters at Step 1070. A simple example, a dose shipment report can be made for a certain beginning date and a certain ending date in accordance with this retained period.

FIG. 50 is specifically designed to provide for a dose shipment report on all Step 1072. This dose shipment report in FIG. 50 and several of the following reports are all based on a very similar routine. The algorithm is designed to generate this report this Dose Shipment Report 1072, as well as the following described reports since they are quite common and usually must be generated. Consequently, for the convenience of the user of the algorithm, these routines are provided for generating these separate reports. It should be understood, however, that some of the could be deleted as may be required and other reports could be added. Further, the reports would similarly have the same routine and steps.

Returning to the Dose Shipment Report 1072, it can be seen when the operator enters date ranges for this report at Step 1074. Otherwise, the operator could literally use that Routine 1048 as shown in FIG. 49. At this point, the operator applies a filter to a data cable at Step 10476. Again, this filter is essentially the same starting and ending filter dates obtained with the date range routine 1048 as shown in FIG. 49. Thereafter, the report information can be either introduced or presented at Step 1078. The report will typically include a report header date, and the product involved, the date, the calibration time, the calibration activity, volume, and the prescription number. This data can, of course, change as may be required.

After the report information is generated it can then be displayed on a screen at Step 1080. Thereafter, the operator can either elect to print or to not print the report at Step 1082. If the operator elects to print the report it will be sent to the printer at Step 1084 or otherwise, abandon this routine. In either case, if the report is printed or not printed, the routine then automatically tells the operator to quit this report at Step 1086 and, thereafter, return to the reports routine which is essentially back to the main screen at Step 1088.

FIG. 53 provides for another important report, namely a disposal report, 1090. This report essentially provides the same function as the test performed test Report 1072 in FIG. 51. Consequently, those referenced numerals used for the test performed report will also be used in connection with this Disposal Report 1090 to identify like functions.

Inasmuch as the Disposal Report essentially has the same function and follows the routine of the test performed report, it is not described in any further detail herein. However, the report information may be different. In this case, the report information at Step 1087, at FIG. 52, would provide for report header information, a delivery number for a particular item or material to be disposed, the radioactive pharmaceutical involved, the disposal activity, how the item is to be disposed, the units of that pharmaceutical, the prescription number, the disposal date, the initials of the operator and where the material is shipped to. Obviously, this information can be altered at the option of the user. Beyond this, the Steps performed in the Disposal Reports of Routine 1090 is the same as that in the Test Performed Report 1072.

FIG. 53 illustrates a Container Return Report 1092. Again, since the functions performed in this container report are the same as that in the Test Performed Report 1072, the same like referenced numerals will be used.

The only difference between these two reports, 1072 and 1092 in FIGS. 51 and 53 is the fact that the report information will be different. In the case of the Container Return Report, the report information at Step 1078 at FIG. 53 will include report header information, perhaps a container number, a survey amount, and the date returned. In addition, such other information such as a wipe amount could be included. This would include, the amount of radiation contained in each wipe implement such as a cotton swap or the like. In addition, the information would include the time for the return of each contained and perhaps a prescription number if a radioactive pharmaceutical or remaining portion thereof is included in the contained, the date received, the description, and the disposal activity. This would include the manner in which the material is disposed. Finally, the initials of the operator may also be included.

FIG. 54 through FIG. 68 all represent additional reports which may be generated by these particular routines. FIG. 54 shows the generation of the residual inventory report, FIG. 55 shows the generation of a patient status report 1096, FIG. 56 shows the generation of a patient information report 1098, and FIG. 57 shows a patient lookup report 1100. The additional reports which are produced are the dose calibrator report 1102, a sealed source inventory report, 1104, an area monitor report, 1106, dose calibrator consistency report 1108, a check in meter information report 1110, a wipe monitor report, 1112, linearity sleeve method report, 1114, a linearity report, 1116, a geometry report, 1118, a cost report, 1120, and a referral source report, 1122.

These reports of FIGS. 54 through 68, are fairly self-explanatory and therefor, are neither illustrated or described in any further detail herein. Moreover, since each of these identified reports are based on exactly the same routine for the test performed report of FIG. 51 and the dose shipment report of FIG. 50, the same referenced numerals used will also be employed in these additional reports.

The only information or material that was different in these additional reports of 1073 starting with FIG. 51 through Search Report 1122 of FIG. 68 is the fact that the information which is introduced or represented is different. The information for each of these subsequent reports will also include a report header information. For the test performed report, information such as the number of tests, the name of the tests, the description of the test, the name of the product used and the identification number of the test may all be reported. For the disposal report, the delivery number, the radio pharmaceutical involved, the disposal date, and the initials of the operator may all be presented. Moreover, this report may contain information as to how the material was disposed and/or where it may have been delivered.

The container return report are 1092 of FIG. 53 would typically include the following information such as the container number, a survey amount, the amount of the radiation, the date returned, the wipe amount, the time of return of the container, the prescription number of each item in the container, that date that it was received, the description, the disposal activity, and the initials of the operator therefor.

The residual inventory report relates to those items which were contacted with radiation but which are being held by the user until the radiation has completely decayed. This would include product involved, the current activity, the prescription number, the date received, the time received, and the initials of the operator. The patient status report would provide such information as date, the total number of patients, the unique patients, that is patients which have special information situations, the total patients which are finished, the total which have been canceled, the total which have been rescheduled and the total which have been refused of this service.

The patient information report 1098 of FIG. 56 would normally provide information such as the name of the patient, the date the patient was dosed, the time of dosing, the exam, the amount of disposed units, the prescription number, and like information. The patient look-up report would include the patient name, the date, time, test to be examined, the status, and the physician room notes.

The dose calibrator report 1102 of FIG. 58 would include information such as the dose calibrator source, including the first, second, and third source. This information would include the date and time, the calculated decay for each of the three sources and the deviation. The sealed source inventory report, 1104 of FIG. 59 would include information such as the product description, the date received, the model and serial numbers, the location, the original activity, and whether or not it has all been accounted for.

The area monitor report of 1106 of FIG. 60 would include information such as the group information, the name and description of the group, the meter information, including, for example, date, time, initials of the operator, the meter examined, the name of the meter, the calibration date, and even the probe involved. If there were any repeats of the monitoring, that information may also be included in the display of 1078.

The dose calibrator consistency report of 1108 of FIG. 61 will include information such as the calibrator information which may be the dose calibrator involved, the serial number, the percent deviation, and a model description. The check in meter information report 1110 of FIG. 62 would include set items such as the delivery number, the date, the time, the survey instrument involved, the wipe instrument involved, the serial number of each, and other information such as the source, background, radioactivity level and package conditions. The Wipe Meter Report 1112 of FIG. 63 may include information such as the name and description of each of the meters involved, the date, time, and initials of the operator monitoring, the meter name, the meter calibration date and even the probe, therefor.

A linearity sleeve method report 1114 of FIG. 64 would include such items as the dose calibrator and date of starting and the time for any calibration. This report would also include information about the sleeves which were used, calibration factors, the assayed activity, the assayed time, decay, and, any corrected calculated percent deviation. The linearity manual method report 1116 of FIG. 65 would include the information about the dose calibrator, the dates calibration started, the number of hours and the source. This may include manual information such as assayed activity, predicted activity, control factors, and a percent deviation.

The geometry report 1118 of FIG. 66 would normally include information about the dose calibrator, including the date started, the time, the normalization, and the activity. This would further include the initials of the user. The report would preferably include geometric geometry information which would possibly represent the volume, the assay time, the assay activity decay, correction, and the correction factor.

The cost report would normally include items such as the total product, the total cost, the number of products with the price set, the product name for each product, the product description, the cost per unit, and the number of units. The total cost for the product and the percent of total units, as well as the percent of total cost may also be presented. The referral source report 1122 of FIG. 68 would include the referral source, the name of the referral source, identification number, if possible, the number of referrals and the percent of appointments.

There may also be a formula report routine 1124 as shown in FIG. 69. In this report, the operator merely either inputs or displays information such as information about the formulas involved. Such information may include, for example, Adenosine 6, Adenosine 5, pediatric dose, Dipyridamole, CPM to DPM and any decay formula therefor. This report does not require the entry of date ranges and also does not require any selected operation such as an operation identified as 1076 in the test performed report and 1076 in the dose shipment report of FIG. 50. Beyond this, the routine would be the same as those previously described routines and particularly the routine for the dose shipment report 1072 of FIG. 50.

A sealed source inventory report 1104 is similar to the dose shipment report 1072 of FIG. 50 except that the operator has an initial decision to make after a selected date at Step 1126. The operator can either quit this report and return to the reports routine or otherwise proceed to the information to the report. The information would include, in addition to the report header, a product description, the date of receipt, the model and serial number, the location, and the original activity.

The area monitor report has a routine essentially identically to the dose shipment report routine 1072 of FIG. 50. Again, like reference numerals will refer to like activity. This report does not include a special decision making step which was included in the sealed source inventory report. That information which may be reported may include for example, group information, the name and description of that group information, meter information, such as the date, time, initials of the operator, the meter involved, the name of the meter, the calibration date, and even the probe. The dose calibrator consistency report, 1108 and the remaining reports from the area monitor report, 1106 at FIG. 62 and the formula for the referral service report, 1122 at FIG. 68 all have essentially the same routine activity. As a result those reference numerals in FIG. 50 will be applied to these following reports at FIGS. 60 through 68.

That information which would be presented with the area monitor report include dose calibrator consistency report would include the calibrator information, the dose calibrator involved, the serial number of that calibrator, the present deviation, possibly calibrator results and the actual calibration of each item.

The check in meter information Report, 1110, would then include that information such as the delivery number, the date and time, the survey instrument or wipe instrument involved, the serial numbers of such instruments, the source and background the surface activity, including radioactivity on that surface and the like.

The wipe monitor report, 1112 at FIG. 63 would essentially include information such as the group information, the name and description of the items in the group, the particular meter information, the date, the time, initials of the operator, the meter name, the meter calibration date and even the probe. The linearity sleeve method report, 1114 at FIG. 64 would include the dose calibrator factor, the assay activity, the assay time, the decay correction factor, and the calculated percent of deviation.

The linearity sleeve method report would also include that Step 1126 for the sealed method inventory report, 1104 at FIG. 59. On this activities in the algorithm are essentially the same. The linearity manual method report, 1116 also included that decision making Step 1126. Beyond this the algorithm is the same as that of the routine dose shipment report, 1072, at FIG. 50. In this case, the information for the report would include the dose calibrator, the date started, the base hours, and the source. The information may further include assay activity, predicated activity, a control factor, and percent deviation.

A geometry report, 1118 at FIG. 66, would also include that decision Step 1126, previously described. In addition, the information to be presented would be essentially that information in the linearity manual Method report except that the geometry information including the volume assay time, assay activity, decay correction, and correction factor.

The cost report, 1120, as shown in FIG. 67 is another report of substantial value to management. In this case, information at Step 1078 at FIG. 67 would include the total product involved, the total cost, the number of products without a price set, a product name, a product description, cost per unit, number of units, total cost for product, and like information. The referral source report, 1122 at FIG. 68 would normally include just a referral source by name and perhaps an identification number, the number of referrals and the percent of appointments. The formula report, 1124 of FIG. 69 is a fairly simple routine which only includes a report of information at Step 1130, such as, for example, dose formulas, e.g., Adenosine 6 minute, Adenosine 5 minute, etc. The remaining portion of the routine for the Formula Report would involve those same activities as set forth in the Dose Shipment Report 1072, at FIG. 50. To that extent, like reference numerals are used.

There is also a daily report routine, 1132 as shown in FIG. 70 of the drawings. This daily report, 1132, can be a fairly important report for management and also for information reporting purposes. In the daily report, such information which may be displayed at Step 1134 includes certain reports to either view or print, a dose shipment, patient information, disposal, check in meter information, residual inventory, area monitor, and area wipe. Other information could also be provided as may be desired.

After the information is viewed, the operator can then provide for a selected report to generate. The information which would be used is at step 1136 includes, for example, dose shipment, patient information, disposal, check in meter information, residual inventory, and area monitoring and area wipe information.

Thereafter, the routine proceeds to Step 1138, which will display the next report screen. The operator then makes a decision at Step 1140 as to whether or not to print the report. If the report is to be printed, it will be sent to the printer at Step 1142. In each case, the operator will have a decision at Step 1144 to determine whether or not to complete all reports. If the operator elects to quit the report at Step 1146, the routine will return to the reports routine at Step 1148.

FIG. 71 illustrates the formation of data tables in the algorithm about the present invention and which also shows a significant feature of the invention. In this case, data is broken down into segments so that there is not a redundancy in information recordation. When the operator introduces information, the data processing system, namely the computer, assigns a computer code number to each of the segments of the data. Those segments of the data can then be correlated. Thus, when the operator introduces information regarding a patient and the radioactive pharmaceutical which may be administered to that patient and the amounts, the amounts may be categorized in one data table, the pharmaceutical in another data table and the patient's name in a third data table.

If age information is to be introduced with respect to a patient, that information may be introduced into a fourth table. In this way, if the operator wishes to recall data for a given patient, the computer will automatically locate the internal computer numbers given to that patient's name and locate the radioactive pharmaceutical and the amount and the age of that patient. In the case of another patient, the same radioactive pharmaceutical may be administered to that other patient in perhaps different amounts. Consequently, at very least the name of the radioactive pharmaceutical is not duplicated in the data system.

As a simple example of the foregoing, if a particular radioactive pharmaceutical Myocene was introduce into the computer it might be arbitrary assigned a code of 001 and Myoview would be given an arbitrary code of 002. If it was desired to determine the amount of these compounds in the inventory of the facility, the operator can merely introduce the compound from 001 and determine that e.g., 50 mg was available. In addition, if the scheduler's name was required to be entered, it would not be necessary for the schedule to introduce that information again creating a redundancy, but rather the scheduler's name would be available under Code 010. The dose amounts may available in another table and again the patients name is in another table.

When it is desired to accumulate this data to determine, for example, the amount of a product given to a patient, that data may be present in the bottom chart of FIG. 72. Thus, in this case, the radioactive pharmaceutical Myoview with an inventory amount of 50 ml., is to be administered to a patient by the name of Jones, in a dose amount of 10 ml. The scheduler who arranged for that information is identified as Smith. Thus, all information is easily and quickly gathered and generated on a displayed screen without necessarily causing the operator to again introduce redundant information and without causing the need for storage of redundant information.

Another one of the important aspects of the present invention, as briefly described above, is the fact that a complete screen showing a routine, for example, may be presented on the monitor. In this way, the viewer can examine all subroutines which must be required, otherwise, the steps which must be performed. When the viewer then accesses any particular subroutine, the subroutine will automatically present those steps necessary for the operator to accomplish that subroutine. The operator performs those steps and upon execution of a return or other keyboard push button switch on the computer keyboard the algorithm will automatically return to the that subroutine or to the main menu.

If the operator forgets that a certain subroutine had been performed, that subroutine will immediately inform the operator that the activity has been performed on that particular day. Thus, the algorithm is essentially fool-proof in that it literally carries the operator through every step that must be performed and almost forces the operator to perform each such activity.

As an example of the foregoing, if the operator was to schedule a group of patients for receiving a radioactive pharmaceutical, the subroutine would present a screen for scheduling the patients. Each of the patients thereafter would be scheduled by the operator. A second screen would provide those radioactive pharmaceuticals which might be administered. The third screen would allow the operator to pick a particular patient who is to receive a pharmaceutical. In the fourth screen the operator would select the pharmaceutical for that patient. In the fifth screen the operator may select the amount which is to be administered and, in the sixth screen the operator would then be required to introduce information about the pharmaceutical after administration.

Thus, there has been illustrated and described a unique and novel algorithm and program for performing method steps in the handling and administration of radioactive pharmaceuticals and which thereby fulfills all of the objects and advantages which have been sought. It should be understood that many changes, modifications, variations, and other uses and applications which will become apparent to those skilled in the art after considering the specification and the accompanying drawings. Therefore, any and all such changes, modifications, variations, and other uses and applications, which do not depart from the spirit and scope of the invention are deemed to be covered by the invention.

Having thus described the invention, what we desire to claim and secure by letters patent is:

1. A computer-implemented process for generating presentations on a display screen of an electronic data processing system for controlling administration of radioactive pharmaceuticals to patients comprising steps of:

scheduling administration of at least one required radioactive pharmaceutical to at least one selected patient;

determining availability of the type of radioactive pharmaceutical in an inventory;

receiving, into the electronic data processing system, information regarding prior administrations to the patient of the type of radioactive pharmaceutical, to determine desired activity of the radioactive pharmaceutical at the time of administration to the patient;

displaying, at the electronic data processing system, a plurality of radioactive pharmaceuticals having the desired radioactive activity;

receiving, at the electronic data processing system, a selection of a radioactive pharmaceutical item having the desired activity from the displayed list of the plurality of radioactive pharmaceuticals;

measuring an amount of radiation for the selected radioactive pharmaceutical item and receiving, at the electronic data processing system, the measured amount of radiation for the selected radioactive pharmaceutical item to verify the amount of radiation is within the desired radioactive activity measured for one dose of the radioactive pharmaceutical in the electronic data processing system;

receiving, at the electronic data processing system, information scanned from a label of a container holding the one dose of the radioactive pharmaceutical; and validating, at the electronic data processing system, information scanned from the label against the inventory for proper radioactive pharmaceutical type and expiration parameters.

2. A computer-implemented process for generating presentations on a display screen of an electronic data processing system for controlling administration of radioactive pharmaceuticals to patients comprising steps of:

receiving an order, at the electronic data processing system, for diagnostic imaging requiring administration of a type of radioactive pharmaceutical;

determining, via the electronic data processing system, if the type of radioactive pharmaceutical is in a hospital inventory;

receiving, into the electronic data processing system, information regarding prior administrations to the patient of the type of radioactive pharmaceutical, to determine desired activity of the radioactive pharmaceutical at a time of administration;

displaying, at the electronic data processing system, a plurality of radioactive pharmaceutical items having the desired radioactive activity;

receiving, into the electronic data processing system, a selection of a radioactive pharmaceutical item having the desired activity from the displayed list of the plurality of radioactive pharmaceuticals;

receiving, at the electronic data processing system, a measured amount of radiation for the selected radioactive pharmaceutical item to verify the amount of radiation is within the desired radioactive activity for the patient, where the measurement occurs after the radioactive pharmaceutical has been selected;

receiving, at the electronic data processing system, information scanned from a label of a container holding the one dose of the radioactive pharmaceutical;

validating, at the electronic data processing system, information scanned from the label against the inventory for proper radioactive pharmaceutical type and expiration parameters; and receiving, at the electronic data proceeding, dosage information for the selected radioactive pharmaceutical item and transmitting the dosage information to a pharmacy computer.

* * * * *